United States Patent
Jung et al.

(10) Patent No.: US 11,261,448 B2
(45) Date of Patent: Mar. 1, 2022

(54) SNAP25 ANTISENSE OLIGONUCLEOTIDES

(71) Applicant: OliPass Corporation, Yongin-si (KR)

(72) Inventors: Daram Jung, Hwaseong-Si (KR); Kangwon Jang, Yongin-Si (KR); Bongjun Cho, Yongin-Si (KR); Min Wook Shin, Yongin-Si (KR); Hyun Ju Jeon, Yongin-Si (KR); Soyoung Kim, Seoul (KR)

(73) Assignee: OliPass Corporation, Yongin-si (KR)

( * ) Notice: Subject to any disclaimer, the term of this patent is extended or adjusted under 35 U.S.C. 154(b) by 489 days.

(21) Appl. No.: 16/475,716

(22) PCT Filed: Dec. 29, 2017

(86) PCT No.: PCT/IB2017/001727
§ 371 (c)(1),
(2) Date: Jul. 3, 2019

(87) PCT Pub. No.: WO2018/127733
PCT Pub. Date: Jul. 12, 2018

(65) Prior Publication Data
US 2019/0338291 A1   Nov. 7, 2019

Related U.S. Application Data

(60) Provisional application No. 62/443,262, filed on Jan. 6, 2017.

(51) Int. Cl.
*C12N 15/11* (2006.01)
*C12N 15/113* (2010.01)
(Continued)

(52) U.S. Cl.
CPC .......... *C12N 15/1138* (2013.01); *A61K 8/606* (2013.01); *A61K 9/0014* (2013.01); *A61P 17/00* (2018.01); *C07K 7/02* (2013.01); *C07K 14/003* (2013.01); *A61K 38/00* (2013.01); *C12N 2310/11* (2013.01); *C12N 2310/3181* (2013.01); *C12N 2320/33* (2013.01)

(58) Field of Classification Search
CPC ...................................................... A61K 8/606
See application file for complete search history.

(56) References Cited

U.S. PATENT DOCUMENTS 6,617,422 B1   9/2003  Nielsen et al.

FOREIGN PATENT DOCUMENTS

| CN | 1408881 A | 4/2003 |
| WO | WO-2009113828 A2 | 9/2009 |
| WO | WO-2018/029517 A1 | 2/2018 |
| WO | WO-2018/122610 A1 | 7/2018 |

OTHER PUBLICATIONS

Extended European Search Report and Written Opinion for EP Application No. 17890613.7 dated Nov. 13, 2020.

(Continued)

*Primary Examiner* — Benjamin J Packard
(74) *Attorney, Agent, or Firm* — Foley Hoag LLP; David P. Halstead; Mi Cai

(57) ABSTRACT

Provided are peptide nucleic acid derivatives targeting a 3' splice site of the human SNAP25 pre-mRNA. The peptide nucleic acid derivatives potently induce at least a splice variant of the human SNAP25 mRNA in cells, and are useful to safely treat dermatological indications or conditions involving the expression of the human SNAP25 protein by topical administration.

10 Claims, 25 Drawing Sheets

Specification includes a Sequence Listing.

(51) Int. Cl.
*A61K 9/00* (2006.01)
*C07K 7/02* (2006.01)
*C07K 14/00* (2006.01)
*A61K 8/60* (2006.01)
*A61P 17/00* (2006.01)
*A61K 38/00* (2006.01)

(56) References Cited

OTHER PUBLICATIONS

Osen-Sand, "Inhibition of axonal growth by SNAP-25 antisense oligonucleotidse in vitro and in vivo," Nature, 364:445-448 (1993).
Antonucci et al., "SNAP-25, a Known Presynaptic Protein with Emerging Postsynaptic Functions," Frontiers in Synaptic Neuroscience, 8(7): 9 pages (2016).
Flanagan et al., "Effects of oligonucleotide length, mismatches and mRNA levels on C-5 propyne-modified antisense potency," Nucleic Acids Research, 24(15): 2936-2941 (1996).
Moccia et al., "Insights on chiral, backbone modified peptide nucleic acids: Properties and biological activity," Artificial DNA: PNA & XNA, 5(3): Article e1107176 (2014).
Swenson et al., "Peptide nucleic acids harness dual information codes in a single molecule," Chemical Communications, 13: 11 pages (2020).
Bark et al., "Developmentally Regulated Switch in Alternatively Spliced SNAP-25 Isoforms Alters Facilitation of Synaptic Transmission," Journal of Neuroscience, 24(40): 8796-8805 (2004).
International Search Report and Written Opinion for International Application No. PCT/IB2017/001727 dated May 31, 2018.
Peacey et al., "Targeting a pre-mRNA Structure with Bipartite Antisense Molecules Modulated Tau Alternative Splicing," Nucleic Acids Research, 40(19): 9836-9849 (2012).
Siwkowski et al., "Identification and Functional Validation of PNAs that Inhibit Murine CD40 Expression by Redirection of Splicing," Nucleic Acids Research, 32(9): 2695-2706 (2004).

Figure 5 (continued from previous page)
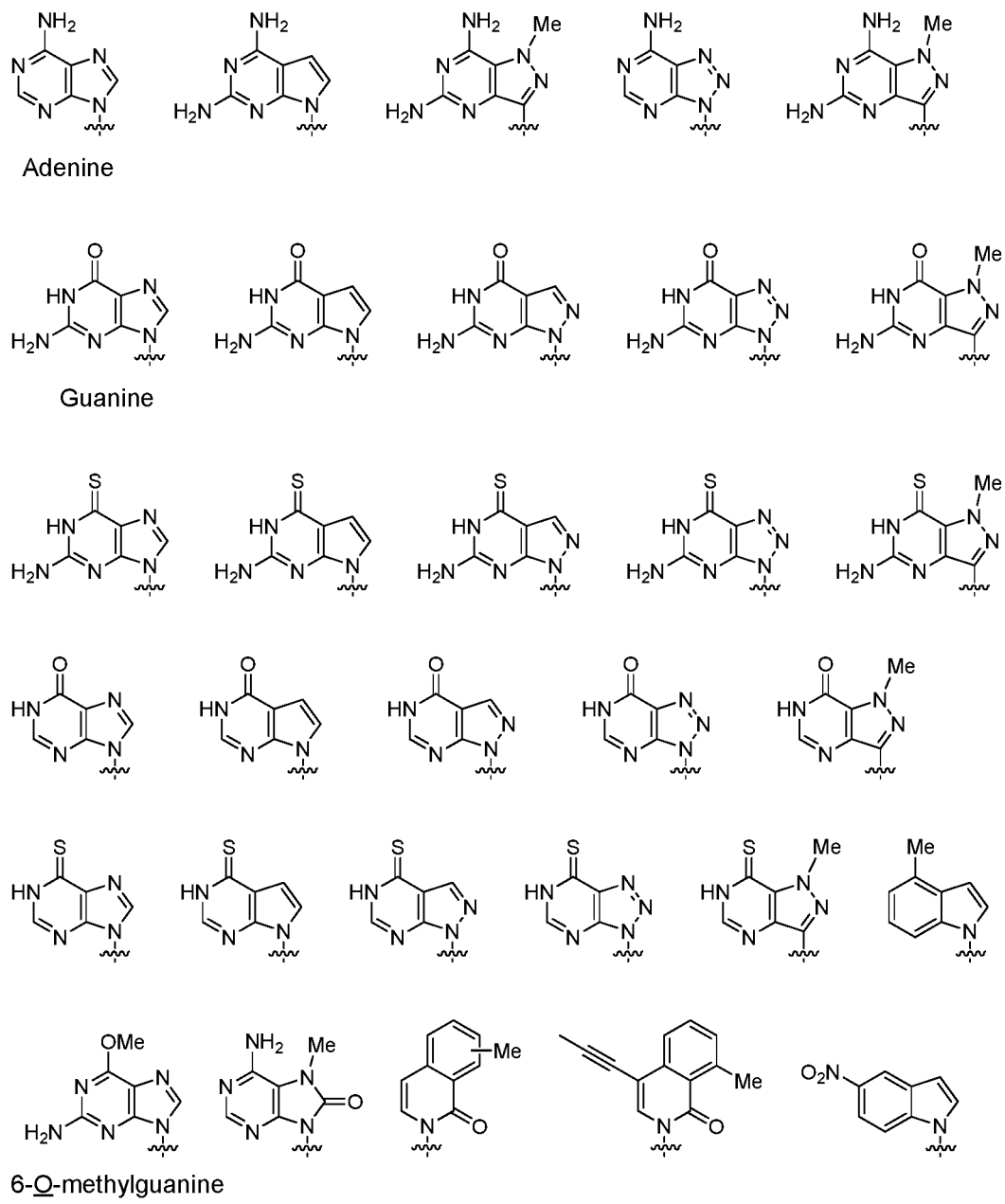

Figure 5 (continued from previous page)
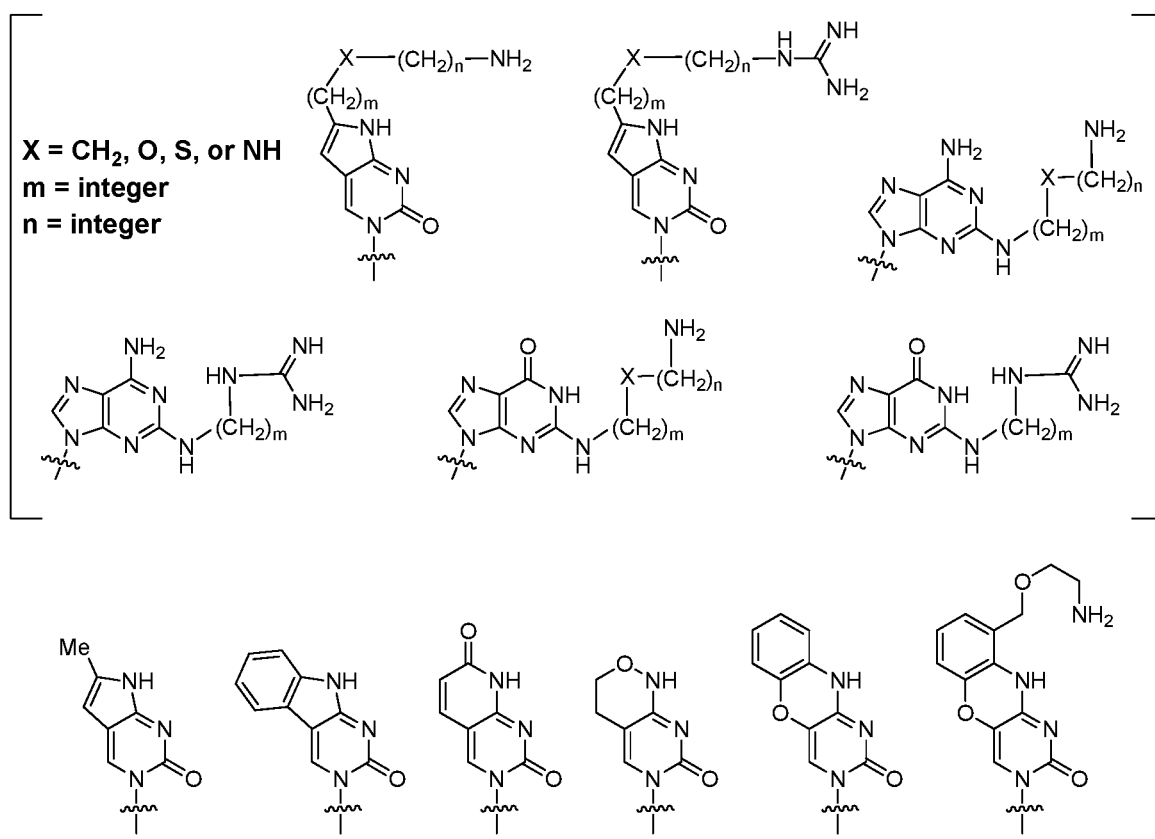

Examples of Non-substituted Alkyl Radical

Examples of Substituted Alkyl Radical

Examples of Non-substituted Alkylacyl Radical

Examples of Substituted Alkylacyl Radical

Examples of Substituted or Non-substituted Arylacyl Radical

Examples of Substituted Alkylamino or Arylamino Radical

Examples of Substituted or Non-substituted Aryl Radical

Examples of Substituted or Non-substituted Alkylsulfonyl or Arylsulfonyl Radical Examples of Substituted or Non-substituted Alkyl- or Aryl-phosphonyl Radical

Examples of Substituted or Non-substituted Alkyloxycarbonyl Radical

Examples of Substituted or Non-substituted Aryloxycarbonyl Radical

Examples of Substituted or Non-substituted Alkylaminocarbonyl Radical

Examples of Substituted or Non-substituted Arylaminocarbonyl Radical

Examples of Substituted or Non-substituted Alkyloxythiocarbonyl Radical

Examples of Substituted or Non-substituted Alkylaminothiocarbonyl Radical

Examples of Substituted or Non-substituted Arylaminothiocarbonyl Radical

Examples of Substituted or Non-substituted Aryloxythiocarbonyl Radical

PNA Monomer

B : Nucleobase
X : O (oxygen atom)
p : Integer
q : Integer

Adenine

B =

Guanine

B =

Thymine

B =

Cytosine

B =

Modified Cytosine

C(pXq) : B =

Modified Adenine

A(p) : B =

A(pXp) :

B =

Modified Guanine

G(p) : B =

G(pXq) :

B =

Fmoc-PNA Monomer

B : Nucleobase with protecting group(s)
X : methylene, oxygen, sulfur, or Boc-protected amino
m : Integer
n : Integer Boc-

Modified Cytosine

C(mXn) :  B =

Modified Adenine

A(mXn) :

B =

Modified Guanine

G(mXn) :

B =

SNAP25 ANTISENSE OLIGONUCLEOTIDES

RELATED APPLICATIONS

This application is a national-stage filing under 35 U.S.C. § 371 of International Application No. PCT/IB2017/001727, filed Dec. 29, 2017, which claims the benefit of priority to U.S. Provisional Application No. 62/443,262 filed Jan. 6, 2017, each of which is incorporated by reference herein in its entirety.

SEQUENCE LISTING

The instant application contains a Sequence Listing which has been submitted electronically in ASCII format and is hereby incorporated by reference in its entirety. Said ASCII copy, created on Jul. 1, 2019, is named OSH-00601_(32567-00601)_SL.txt and is 3,683 bytes in size.

BACKGROUND OF INVENTION

Endocytosis is a process for cells to uptake large molecules into cell. In the meantime, exocytosis is a process for cells to secrete intracellular materials or content out of cell. There are abundant types of cells smartly adopting exocytosis to secrete vesicular content or materials out of cell. Neuronal cells have evolved to secrete neurotransmitters by exocytosis for their destined physiological roles to communicate with neighboring neuronal cells or neighboring tissues. As another example for exocytosis, mast cells release histamine by exocytosis and resultantly recruit immune cells.

Secretory vesicles contain various types of vesicular materials which would vary depending on cell type. For example, presynaptic vesicles in neuronal cell are located in presynaptic neuronal terminals and contain a cocktail of neurotransmitters. The vesicular membrane fuses with the plasma membrane to release neurotransmitters into synaptic region to physiologically control or affect neighboring cells or tissues. β-cells in the pancreatic islets possess vesicles charged with insulin, and the vesicles undergo exocytosis involving membrane fusion to release insulin into the blood stream in response to blood glucose level. [*Cell Metabolism*, vol 5, 237-252 (2007)]

Exocytosis is a cellular process involving a fusion of the vesicular membrane with the plasma membrane. There are two types of exocytosis, i.e. "constitutive" and "regulated". "Constitutive" exocytosis spontaneously occurs without a stimulatory signal. In the meantime, "regulated" exocytosis is triggered by a specific stimulatory signal, for example, an increase in the intracellular calcium ion concentration in motor-neuronal cells. [*Ann. Rev. Cell Dev. Biol.* vol 16, 19-49 (2000)]

Exocytosis in Synaptic Junction: Neuronal cells communicate with each other using a machinery called "synaptic junction" specialized in neuronal cells. The exocytosis process occurring in the synaptic junction between neighboring neuronal cells is schematically illustrated in FIG. 1A. First, vesicles containing neurotransmitter particles fuse with the presynaptic plasma membrane in response to a stimulatory signal such as a change in the calcium ion concentration sensed by the neuronal axon. Upon the membrane fusion, neurotransmitter particles are released into the presynaptic junction. Then the neurotransmitter particles diffuse and bind to neurotransmitter receptors expressed on the dendritic membrane of a neighboring neuronal cell. Finally the receptors are activated upon complexation with a neurotransmitter molecule, and transduce the neuronal signal transmitted from the axon of the neighboring neuronal cell.

Exocytosis in Neuromuscular Junction: Motor neurons control the movement of muscles using the exocytosis in the neuromuscular junction. In muscles, an axon of motor neuron branches into a number of axon terminals to form junctions with the sarcolemma membrane of muscle cells, i.e., neuromuscular junctions. [*Nat. Rev. Neuroscience*, vol 2, 791-805 (2001)] The gap between the neuronal axon terminal and the muscle cell membrane is called synaptic cleft of a ca 30 nm dimension.

As a nerve pulse in the form of action potential reaches the axon terminal of a motor neuron, synaptic transmission begins at the neuromuscular junction. The motor neuron axon releases neurotransmitter molecules (i.e. acetylcholine in vertebrates) into the synaptic cleft by exocytosis, and acetylcholine receptors expressed on the muscle cell membrane are activated upon complexation with acetylcholine, which triggers the contraction of the muscle fiber. The exocytosis process occurring in the neuromuscular junction between neuronal axon and muscle cell is schematically illustrated in FIG. 1B.

SNARE Proteins and Neuronal Exocytosis: The fusion of the vesicular and the neuronal cell membrane is essential for "regulated" exocytosis. Such "regulated" exocytosis has been known to be mediated by SNARE (soluble N-ethylmaleimide-sensitive factor attachment protein receptors) proteins. [*Ann. Rev. Cell Dev. Biol.* vol 16, 19-49 (2000)]. In the neuronal exocytosis are involved three SNARE proteins, i.e., vesicle-associated membrane protein (VAMP2, also known as synaptobrevin), a single-pass transmembrane protein located in the vesicular membrane (v-SNARE); synaptosome-associated protein of 25 kDa (SNAP25); and syntaxin 1A, a single transmembrane protein that resides in the neuronal plasma membrane (t-SNARE). Syntaxin 1A and VAMP2 possess a C-terminal trans-membrane domain for anchoring into the vesicular and neuronal plasma membrane, respectively. The membrane anchoring of SNAP25 is facilitated by the palmitoyl groups covalently attached to several cysteine residues in the protein. [*Am. J. Physiol. Cell Physiol.* vol 285, C237-249 (2003)]

The neuronal axon potential activates voltage-gated calcium channels and increases the calcium ion concentration within the axon, which pulls down synaptic vesicles near the presynaptic membrane by complexation of calcium ions with synaptotagmin. Then the fusion of the synaptic vesicular membrane with the axonal plasma membrane is assisted as schematically illustrated in FIG. 2A. The formation of the ternary complex of syntaxin, SNAP25 and snaptobrevin drives the two membranes to orient in close proximity and then to undergo membrane fusion to release acetylcholine particles into the synaptic cleft. [*Toxins* vol 2, 24-53 (2010)] Thus, the ternary complex formation of the SNARE proteins is the essential element of the membrane fusion involved in the release of neurotransmitters.

Botulinum Toxin A: Botulinum toxin (BTX) is a neurotoxin produced by the bacterium *Clostridium botulinum*. The active form of toxin is a single polypeptide chains (150 kDa) consisting of the heavy (100 kDa) and light (50 kDa) chain tethered to each other with a disulfide bond. BTX is known to be readily be taken up into neuronal cell, cleaves SNARE proteins, block the release of acetylcholine, and resultantly deprive the neuronal cell of the very essential character as neuronal cell. Neuronal cells exposed to BTX fail to trigger the contraction of neighboring muscle fibers.

Upon entry into neuronal cell, BTX is cleaved into two parts, i.e. the light and heavy chain. The light chain is a zinc metalloprotease responsible for the role as neurotoxin. BTX subtypes A, C and E cleave SNAP25. In the meantime, subtypes B, D, F and G degrade VAMP, and subtype C hydrolyzes syntaxin. [*Nature*, vol 365, 160-163 (1993)].

Cosmetic Use of Botulinum Toxin A: Botulinum toxin A was originally developed by Allergan for cosmetic use mainly to treat facial wrinkles. Botox® is a famous brand name registered by Allergan, and is often taken as synonymous to BTX in public communities.

Given with its physiological activity, BTX A can be used in principle to treat a number of disorders involving overactive muscle contractions or spasms of the head and neck, eyelid, limbs, jaw, and vocal cords. Additionally, BTX may be used to treat hypersecretive disorders including hypersalivation and hyperhidrosis. [*Indian J. Dermatol.* vol 55, 8-14 (2010)]

Botox® injection was approved by the US FDA in 2002 for the treatment of facial wrinkles, and is regarded as safe if properly practiced by skilled dermatologists. However BTX is notorious for its toxicity. BTX type A and B, for example, are estimated to be lethal to humans if intravenously injected at 1.3~2.1 ng/kg. [*Indian J. Dermatol.* vol 55, 8-14 (2010)] There are still concerns about the safety of BTX for cosmetic use. Facial paralysis, muscle weakness, and trouble of swallowing are the most common adverse events observed in subjects administered with intramuscular BTX injection. More serious side effects are caused by systemic exposure due to overdose or poor skills of local intramuscular injection, and include headache, flu-like syndromes, and allergic reactions. Repeated BTX injections are known to induce antigenic responses, which limits the cosmetic use of BTX. Side effects from therapeutic use can be more serious than cosmetic use, and may include arrhythmia, heart attack, seizures, respiratory arrest, and death. [*J. Am. Acad. Dermatol.* vol 53, 407-415 (2005)]

In order to minimize the side effects in subjects receiving BTX injection for cosmetic use, localized or topical delivery of BTX would be very preferred in place of the conventional route of the intramuscular local injection. BTX is a macromolecule of 150K size. It is still an extreme challenge to topically deliver BTX deep into the muscle layer underneath the dermis without relying invasive formulations.

Argireline: Argireline is a synthetic hexa-peptide derived from the N-terminal of the SNAP25 protein. Argireline is marketed as cosmetic products for facial wrinkles. The hexapeptide has been claimed to antagonize the formation of the SNARE complex with the SNAP25 protein. The hexapeptide is mimicking the function of BTX, and would be useful to reduce facial wrinkles upon topical administration. Argireline was reported to reduce facial wrinkles in human subjects upon topical use. [*Am. J. Clin. Dermatol.* vol 14(2), 147-153 (2013)]

Pre-mRNA: Genetic information is carried on DNA (2-deoxyribose nucleic acid). DNA is transcribed to produce pre-mRNA (pre-messenger ribonucleic acid) in the nucleus. Mammalian pre-mRNA usually consists of exons and introns, and exon and intron are inter-connected to each other as schematically provided below. Exons and introns are numbered as schematically illustrated in FIG. 2B.

Splicing of Pre-mRNA: Pre-mRNA is processed into mRNA following deletion of introns by a series of complex reactions collectively called "splicing" as schematically summarized FIG. 3A. [*Ann. Rev. Biochem.* 72(1), 291-336 (2003); *Nature Rev. Mol. Cell Biol.* 6(5), 386-398 (2005); *Nature Rev. Mol. Cell Biol.* 15(2), 108-121 (2014)] Splicing is initiated by forming "spliceosome E complex" (i.e. early splicesome complex) between pre-mRNA and splicing adapter factors. In "spliceosome E complex", U1 binds to the junction of exon N and intron N, and U2AF$^{35}$ binds to the junction of intron N and exon (N+1). Thus the junctions of exon/intron or intron/exon are critical to the formation of the early spliceosome complex. "Spliceosome E complex" evolves into "spliceosome A complex" upon additional complexation with U2. The "spliceosome A complex" undergoes a series of complex reactions to delete or splice out the intron to adjoin the neighboring exons.

Ribosomal Protein Synthesis: Proteins are encoded by DNA (2-deoxyribose nucleic acid). In response to cellular stimulation or spontaneously, DNA is transcribed to produce pre-mRNA (pre-messenger ribonucleic acid) in the nucleus. The introns of pre-mRNA are enzymatically spliced out to yield mRNA (messenger ribonucleic acid), which is then translocated into the cytoplasm. In the cytoplasm, a complex of translational machinery called ribosome binds to mRNA and carries out the protein synthesis as it scans the genetic information encoded along the mRNA. [*Biochemistry* vol 41, 4503-4510 (2002); *Cancer Res.* vol 48, 2659-2668 (1988)]

Antisense Oligonucleotide (ASO): An oligonucleotide binding to nucleic acid including DNA, mRNA and pre-mRNA in a sequence specific manner (i.e. complementarily) is called antisense oligonucleotide (ASO).

If an ASO tightly binds to an mRNA in the cytoplasm, for example, the ASO may be able to inhibit the ribosomal protein synthesis along the mRNA. ASO needs to be present within the cytoplasm in order to inhibit the ribosomal protein synthesis of its target protein.

If an ASO tightly binds to a pre-mRNA in the nucleus, the ASO may be able to inhibit or modulate the splicing of pre-mRNA into mRNA. The ASO needs to be present within the nucleus in order to inhibit or modulate the splicing of pre-mRNA into mRNA. Such antisense inhibition of splicing produces an mRNA or mRNAs lacking the exon targeted by the ASO. Such mRNA(s) is called "splice variant(s)", and encodes protein(s) smaller than the protein encoded by the full-length mRNA.

In principle, splicing can be interrupted by inhibiting the formation of "spliceosome E complex". If an ASO tightly binds to a junction of (5'→3') exon-intron, i.e. "5' splice site", the ASO blocks the complex formation between pre-mRNA and factor U1, and therefore the formation of "spliceosome E complex" Likewise, "spliceosome E complex" cannot be formed if an ASO tightly binds to a junction of (5'→3') intron-exon, i.e. "3' splice site". 3' splice site and 5' splice site are schematically illustrated in FIG. 3B.

Unnatural Oligonucleotides: DNA or RNA oligonucleotides are susceptible to degradation by endogenous nucleases, limiting their therapeutic utility. To date, many types of unnatural (i.e., non-naturally occurring) oligonucleotides have been developed and studied intensively. [*Clin. Exp. Pharmacol. Physiol.* vol 33, 533-540 (2006)] Some of them show extended metabolic stability compared to DNA and RNA. Provided in FIG. 4A are the chemical structures for some of representative unnatural oligonucleotides. Such oligonucleotides predictably bind to complementary nucleic acid as DNA or RNA does.

Phosphorothioate Oligonucleotide: Phosphorothioate oligonucleotide (PTO) is a DNA analog with one of the backbone phosphate oxygen atoms replaced with a sulfur atom per monomer. Such a small structural change made PTO comparatively resistant to degradation by endogenous nucleases. [*Ann. Rev. Biochem.* vol 54, 367-402 (1985)]

Reflecting the structural similarity in the backbone of PTO and DNA, they both poorly penetrate the cell membrane in most mammalian cell types. For some types of cells abundantly expressing transporter(s) of DNA, however, DNA and PTO show good cell penetration. Systemically administered PTOs are known to readily distribute to the liver and kidney. [*Nucleic Acids Res*. vol 25, 3290-3296 (1997)]

In order to facilitate PTO's cell penetration in vitro, lipofection has been popularly employed. However, lipofection physically alters the cell membrane, elicits cytotoxicity, and therefore would not be ideal for long term in vivo therapeutic use.

Over the past 30 years, antisense PTOs and variants of PTOs have been clinically evaluated to treat cancers, immunological disorders, metabolic diseases, and so on. [*Biochemistry* vol 41, 4503-4510 (2002); *Clin. Exp. Pharmacol. Physiol*. vol 33, 533-540 (2006)] Many of such antisense drug candidates have not been successfully developed partly due to PTO's poor cell permeability. In order to overcome the poor cell permeability, PTO needs to be administered at high dose for therapeutic activity. However, PTOs are known to show dose-limiting toxicity including increased coagulation time, complement activation, tubular nephropathy, Kupffer cell activation, and immune stimulation including splenomegaly, lymphoid hyperplasia, mononuclear cell infiltration. [*Clin. Exp. Pharmacol. Physiol*. vol 33, 533-540 (2006)]

Many antisense PTOs have been found to show clinical activity for diseases with a significant contribution from the liver or kidney. Mipomersen is a PTO analog which inhibits the synthesis of apoB-100, a protein involved in LDL cholesterol transport. Mipomersen manifested therapeutic activity in a population of atherosclerosis patients most likely due to its preferential distribution to the liver. [*Circulation* vol 118(7), 743-753 (2008)] ISIS-113715 is a PTO antisense analog inhibiting the synthesis of protein tyrosine phosphatase 1B (PTP1B), and was found to show therapeutic activity in type II diabetes patients. [*Curr. Opin. Mol. Ther*. vol 6, 331-336 (2004)]

Locked Nucleic Acid: In locked nucleic acid (LNA), the backbone ribose ring of RNA is structurally constrained to increase the binding affinity for RNA or DNA. Thus, LNA may be regarded as a high affinity DNA or RNA analog. [*Biochemistry* vol 45, 7347-7355 (2006)]

Phosphorodiamidate Morpholino Oligonucleotide: In phosphorodiamidate morpholino oligonucleotide (PMO), the backbone phosphate and 2-deoxyribose of DNA are replaced with phosphoramidate and morpholine, respectively. [*Appl. Microbiol. Biotechnol*. vol 71, 575-586 (2006)] Whilst the DNA backbone is negatively charged, the PMO backbone is not charged. Thus the binding between PMO and RNA is free of electrostatic repulsion between the backbones, and tends to be stronger than the binding between DNA and RNA. Since PMO is structurally very different from DNA, PMO wouldn't be recognized by the hepatic transporter(s) recognizing DNA or RNA. Nevertheless, PMO doesn't readily penetrate the cell membrane.

Peptide Nucleic Acid: Peptide nucleic acid (PNA) is a polypeptide with N-(2-aminoethyl)glycine as the unit backbone, and was discovered by Dr. Nielsen and colleagues. [*Science* vol 254, 1497-1500 (1991)] The chemical structure and abbreviated nomenclature of PNA are illustrated in FIG. 4B. Like DNA and RNA, PNA also selectively binds to complementary nucleic acid. [*Nature (London)* vol 365, 566-568 (1992)] In binding to complementary nucleic acid, the N-terminus of PNA is regarded as equivalent to the "5'-end" of DNA or RNA, and the C-terminus of PNA as equivalent to the "3'-end" of DNA or RNA.

Like PMO, the PNA backbone is not charged. Thus the binding between PNA and RNA tends to be stronger than the binding between DNA and RNA. Since PNA is markedly different from DNA in the chemical structure, PNA wouldn't be recognized by the hepatic transporter(s) recognizing DNA, and would show a tissue distribution profile different from that of DNA or PTO. However, PNA also poorly penetrates the mammalian cell membrane. (*Adv. Drug Delivery Rev*. vol 55, 267-280, 2003)

Modified Nucleobases to Improve Membrane Permeability of PNA: PNA was made highly permeable to the mammalian cell membrane by introducing modified nucleobases (i.e., bases) with a cationic lipid or its equivalent covalently attached thereto as exemplified in FIG. 4C. Such modified nucleobases of cytosine, adenine, and guanine were found to predictably and complementarily hybridize with guanine, thymine, and cytosine, respectively. [PCT Appl. No. PCT/KR2009/001256; EP2268607; U.S. Pat. No. 8,680,253]

Incorporation of such modified nucleobases onto PNA simulates situations of lipofection. By lipofection, oligonucleotide molecules with phosphate backbone are wrapped with cationic lipid molecules such as lipofectamine, and such lipofectamine/oligonucleotide complex tends to penetrate the cell membrane rather easily compared to naked oligonucleotide molecule.

In addition to good membrane permeability, those PNA derivatives were found to possess ultra-strong affinity for complementary nucleic acid. For example, introduction of 4 to 5 modified nucleobases onto 11- to 13-mer PNA derivatives readily yielded a $T_m$ gain of 20° C. or higher in duplex formation with complementary DNA. Such PNA derivatives are highly sensitive to a single base mismatch. A single base mismatch resulted in a $T_m$ loss of 11 to 22° C. depending on the type of modified base as well as PNA sequence. ° C.

Small Interfering RNA (siRNA): Small interfering RNA (siRNA) refers to a double stranded RNA of 20-25 base pairs. [*Microbiol. Mol. Biol. Rev*. vol 67(4), 657-685 (2003)] The antisense strand of siRNA somehow interacts with proteins to form an "RNA-induced Silencing Complex" (RISC). Then the RISC binds to a certain portion of mRNA complementary to the antisense strand of siRNA. The mRNA complexed with the RISC undergoes cleavage to yield another copy of double stranded siRNA. Thus siRNA catalytically induces the cleavage of its target mRNA, and consequently inhibits the protein expression by the mRNA. The RISC does not always bind to the full complementary sequence within its target mRNA, which raises concerns of off-target effects in the siRNA therapy. Like other classes of oligonucleotide with DNA or RNA backbone, siRNA possesses poor cell permeability and therefore tends to show poor in vitro or in vivo therapeutic activity unless properly formulated or chemically modified to show good membrane permeability.

SNAP25 ASOs and siRNAs: SNAP25 ASOs and siRNAs were evaluated primarily as a biological tool to better understand physiological roles of the SNAP25 protein in neuronal cells. [*Nature* vol 364, 445-448 (1993); *Eur. J. Neurosci*. vol 20(6), 1593-1603 (2004); *EMBO Reports* vol 14(7) 645-651 (2013); *J. Biol. Chem*. vol 281(38), 28174-28184 (2006)] Oligonucleotides down-regulating the activity of the SNAP25 protein have yet to be investigated for a topical use to safely mimic the beneficial therapeutic activities of BTX. It should be noted that trans-dermal delivery has been a huge technical challenge in the field of oligonucleotide.

BRIEF DESCRIPTION OF FIGURES

FIG. 15B discloses from top to bottom three nucleic acid sequences which are identical and set forth in SEQ ID NO: 16.

SUMMARY OF INVENTION

Figure 1A:
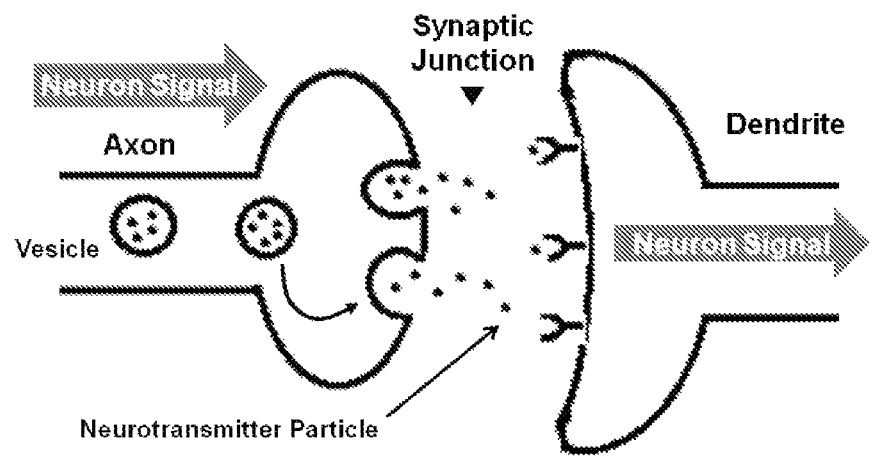
FIG. 1A. Schematic illustration of the exocytosis process occurring in the synaptic junction between two neighboring neuronal cells.
Figure 1B:
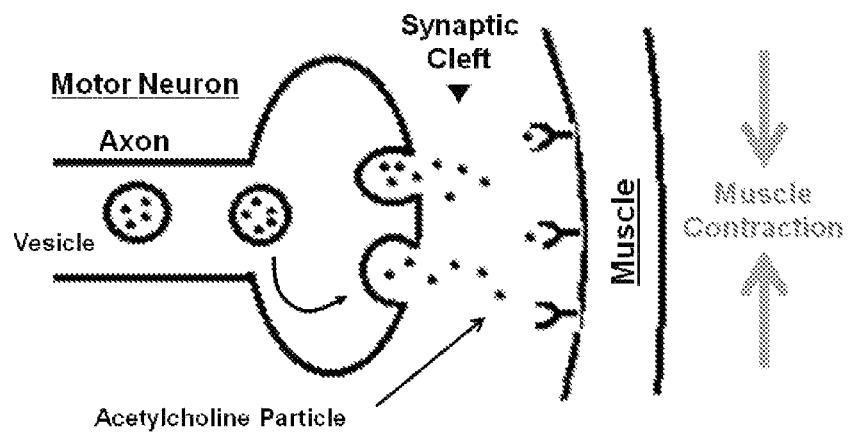
FIG. 1B. Schematic illustration of the exocytosis process occurring in the neuromuscular junction between neuronal axon and muscle cell.
Figure 2A:
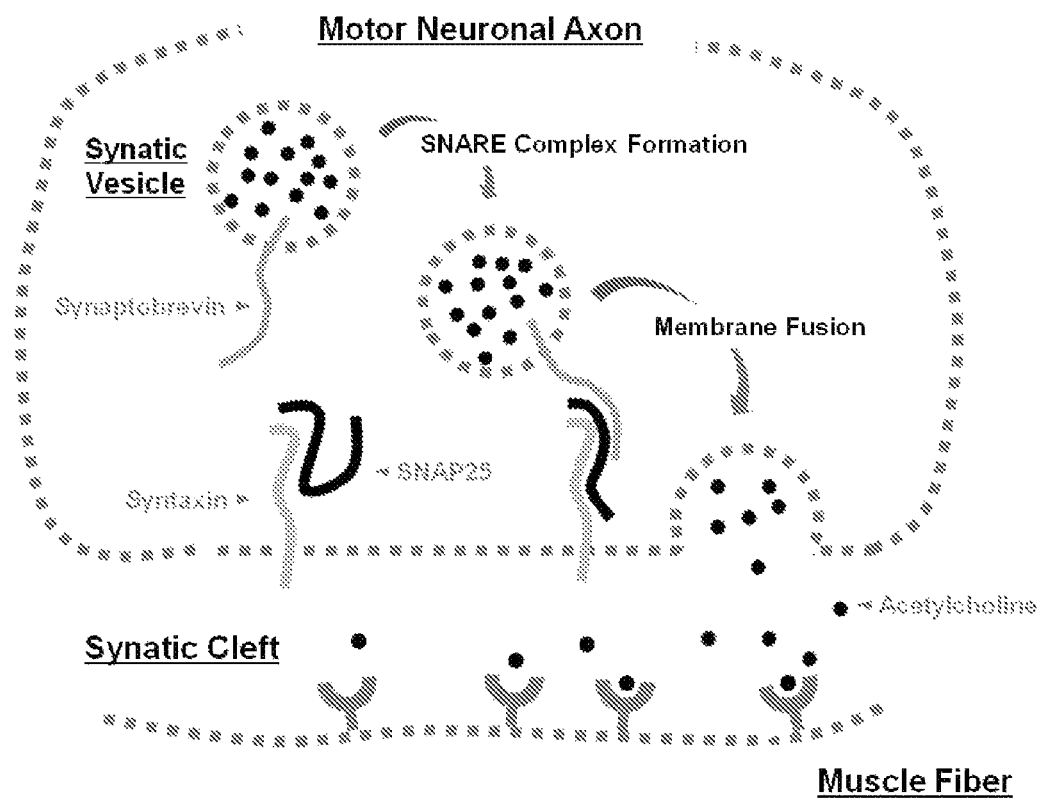
FIG. 2A. Schematic illustration of the fusion of the synaptic vesicular membrane with the axonal plasma membrane.
Figure 2B:
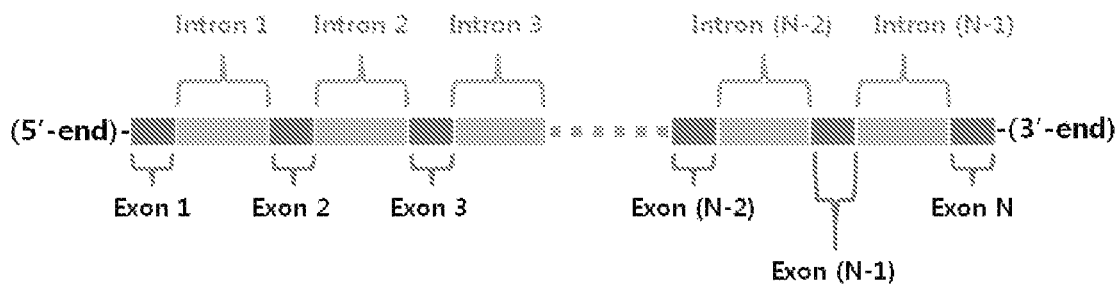
FIG. 2B. Schematic illustration of the numbering of exons and introns within a pre-mRNA.
Figure 3A:
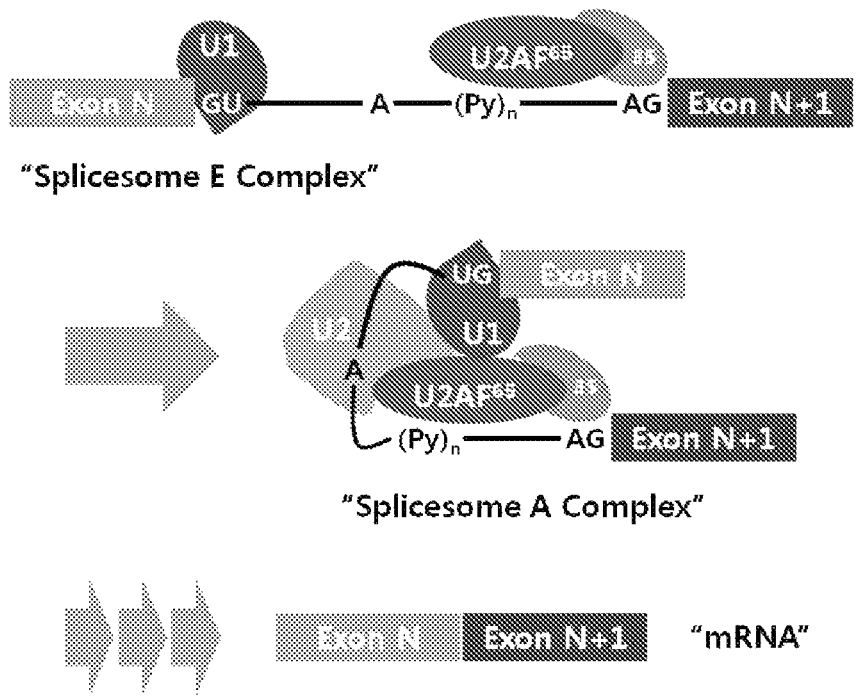
FIG. 3A. Schematic illustration of the splicing process leading to the deletion of intron N.
Figure 3B:
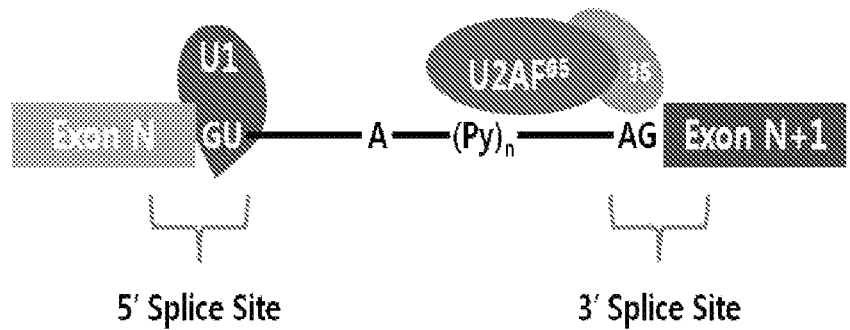
FIG. 3B. Schematic illustration of the 3' splice site and the 5' splice site in relation to splicesome E complex.
Figure 4A:
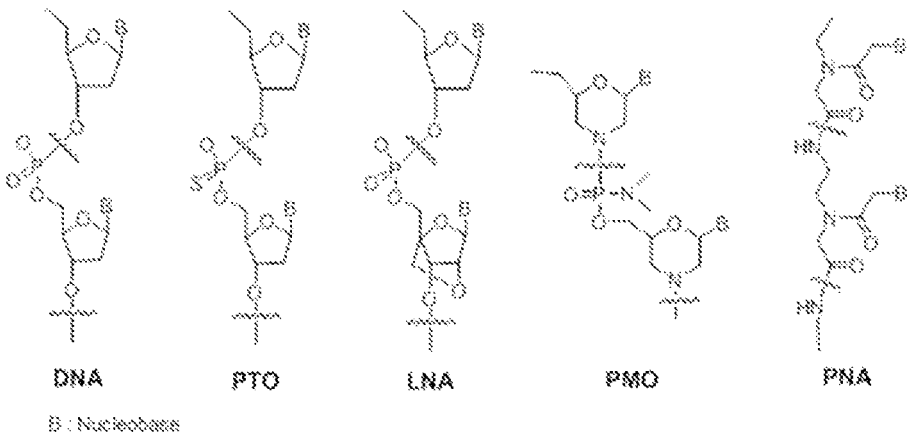
FIG. 4A. Representative chemical structures for DNA and unnatural nucleic acids.
Figure 4B:
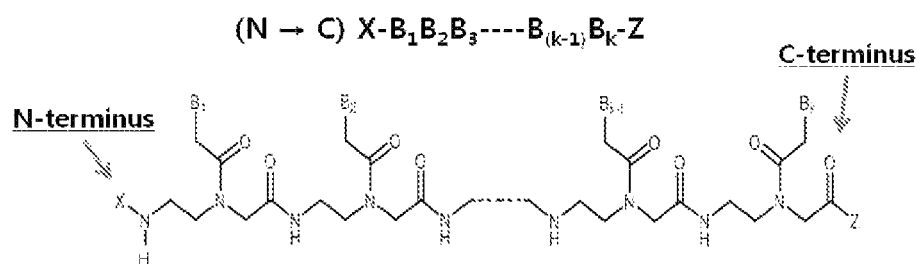
FIG. 4B. Illustration for the chemical structure and abbreviated nomenclature of PNA.
Figure 4C:
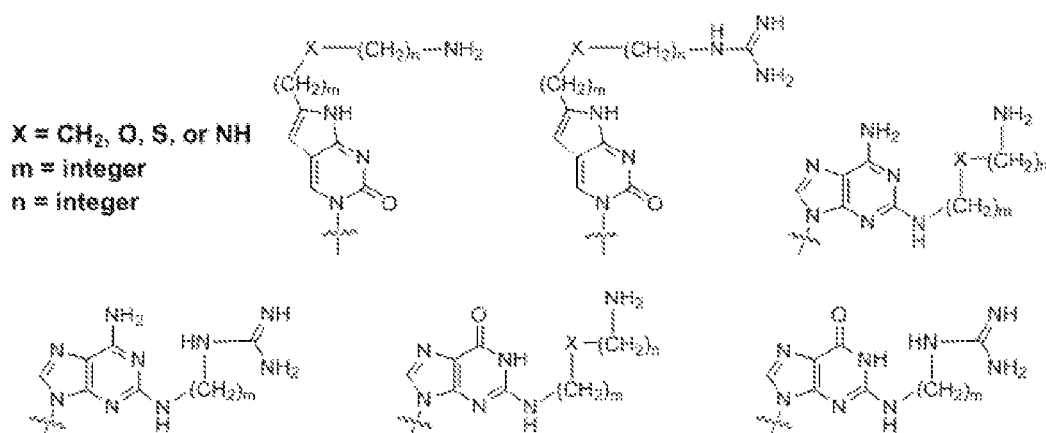
FIG. 4C. Examples of modified nucleobases employed to improve the cell permeability of peptide nucleic acid.

The present invention provides a peptide nucleic acid derivative represented by Formula I, or a pharmaceutically acceptable salt thereof:

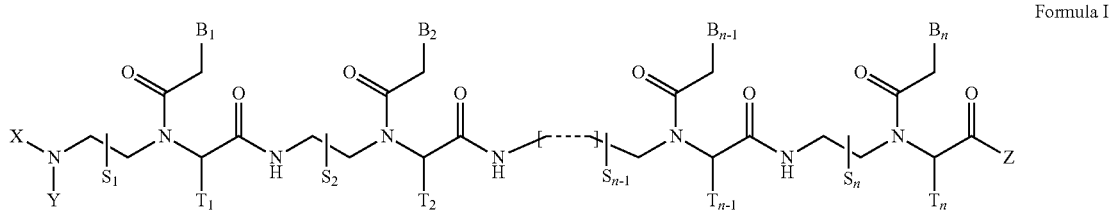

Formula I wherein, n is an integer between 10 and 25;

the compound of Formula I possesses at least a 10-mer complementary overlap with a 14-mer pre-mRNA sequence of [(5'→3') AUCCCAGGGUAACA (SEQ ID NO: 1)] in the human SNAP25 pre-mRNA;

the compound of Formula I is fully complementary to the human SNAP25 pre-mRNA, or partially complementary to the human SNAP25 pre-mRNA with one or two mismatches;

$S_1, S_2, \ldots, S_{n-1}, S_n, T_1, T_2, \ldots, T_{n-1}$, and $T_n$ independently represent deuterido [D], hydrido [H], substituted or non-substituted alkyl, or substituted or non-substituted aryl radical;

X and Y independently represent hydrido, formyl [H—C(=O)—], aminocarbonyl [NH$_2$—C(=O)—], aminothiocarbonyl [NH$_2$—C(=S)—], substituted or non-substituted alkyl, substituted or non-substituted aryl, substituted or non-substituted alkylacyl, substituted or non-substituted arylacyl, substituted or non-substituted alkyloxycarbonyl, substituted or non-substituted aryloxycarbonyl, substituted or non-substituted alkylaminocarbonyl, substituted or non-substituted arylaminocarbonyl, substituted or non-substituted alkylaminothiocarbonyl, substituted or non-substituted arylaminothiocarbonyl, substituted or non-substituted alkyloxythiocarbonyl, substituted or non-substituted aryloxythiocarbonyl, substituted or non-substituted alkylsulfonyl, substituted or non-substituted arylsulfonyl, substituted or non-substituted alkylphosphonyl radical, or substituted or non-substituted arylphosphonyl radical;

Z represents hydrido, hydroxy, substituted or non-substituted alkyloxy, substituted or non-substituted aryloxy, substituted or non-substituted amino, substituted or non-substituted alkyl, or substituted or non-substituted aryl radical;

$B_1, B_2, \ldots, B_{n-1}$, and $B_n$ are independently selected from natural nucleobases including adenine, thymine, guanine, cytosine and uracil, and unnatural nucleobases; and, at least four of $B_1, B_2, \ldots, B_{n-1}$, and $B_n$ are independently selected from unnatural nucleobases with a substituted or non-substituted amino radical covalently linked to the nucleobase moiety.

The compound of Formula I induces the skipping of "exon 7" in the human SNAP25 pre-mRNA, yields the human SNAP25 mRNA splice variant(s) lacking "exon 7", and therefore is useful to inhibit the functional activity of the gene transcribing the human SNAP25 pre-mRNA.

DESCRIPTION OF INVENTION

The present invention provides a peptide nucleic acid derivative represented by Formula I, or a pharmaceutically acceptable salt thereof:

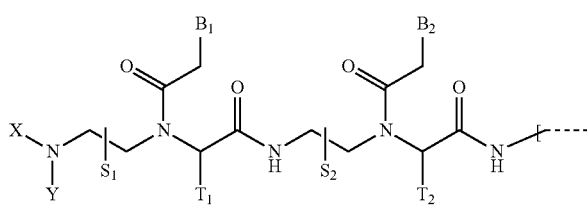
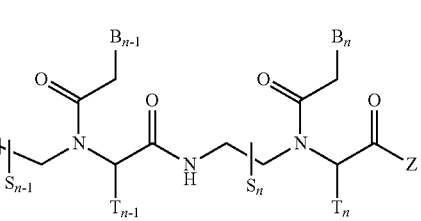

Formula I wherein, n is an integer between 10 and 25;

the compound of Formula I possesses at least a 10-mer complementary overlap with a 14-mer pre-mRNA sequence of [(5'→3') AUCCCAGGGUAACA (SEQ ID NO: 1)] in the human SNAP25 pre-mRNA;

the compound of Formula I is fully complementary to the human SNAP25 pre-mRNA, or partially complementary to the human SNAP25 pre-mRNA with one or two mismatches;

$S_1, S_2, \ldots, S_{n-1}, S_n, T_1, T_2, \ldots, T_{n-1}$, and $T_n$ independently represent deuterido [D], hydrido [H], substituted or non-substituted alkyl, or substituted or non-substituted aryl radical;

X and Y independently represent hydrido, formyl [H—C(=O)—], aminocarbonyl [NH$_2$—C(=O)—], aminothiocarbonyl [NH$_2$—C(=S)—], substituted or non-substituted alkyl, substituted or non-substituted aryl, substituted or non-substituted alkylacyl, substituted or non-substituted arylacyl, substituted or non-substituted alkyloxycarbonyl, substituted or non-substituted aryloxycarbonyl, substituted or non-substituted alkylaminocarbonyl, substituted or non-substituted arylaminocarbonyl, substituted or non-substituted alkylaminothiocarbonyl, substituted or non-substituted arylaminothiocarbonyl, substituted or non-substituted alkyloxythiocarbonyl, substituted or non-substituted aryloxythiocarbonyl, substituted or non-substituted alkylsulfonyl, substituted or non-substituted arylsulfonyl, substituted or non-substituted alkylphosphonyl radical, or substituted or non-substituted arylphosphonyl radical;

Z represents hydrido, hydroxy, substituted or non-substituted alkyloxy, substituted or non-substituted aryloxy, substituted or non-substituted amino, substituted or non-substituted alkyl, or substituted or non-substituted aryl radical;

$B_1, B_2, \ldots, B_{n-1}$, and $B_n$ are independently selected from natural nucleobases including adenine, thymine, guanine, cytosine and uracil, and unnatural nucleobases; and, at least four of $B_1, B_2, \ldots, B_{n-1}$, and $B_n$ are independently selected from unnatural nucleobases with a substituted or non-substituted amino radical covalently linked to the nucleobase moiety.

The compound of Formula I induces the skipping of "exon 7" in the human SNAP25 pre-mRNA, yields the human SNAP25 mRNA splice variant(s) lacking "exon 7", and therefore is useful to inhibit the functional activity of the gene transcribing the human SNAP25 pre-mRNA.

The condition adopted to describe the compound of Formula I that "n is an integer between 10 and 25" literally states that n is an integer selectable from a group of integers of 11, 12, 13, 14, 15, 16, 17, 18, 19, 20, 21, 22, 23, and 24.

The compound of Formula I complementarily binds to the 3' splice site of "exon 7" of the human SNAP25 pre-mRNA read out from the human SNAP25 gene [accessed from NCBI Reference Sequence: NG_029626.1]. The 14-mer sequence of [(5'→3') AUCCCAGGGUAACA (SEQ ID NO: 1)] spanning the junction of "intron 6" and "exon 7" in the human SNAP25 pre-mRNA is a 3' splice site consisting of 7-mer from "intron 6" and 7-mer from "exon 7". Thus the 14-mer pre-mRNA sequence may be conventionally denoted as [(5'→3') aucccag|GGUAACA (SEQ ID NO: 1)], wherein the intron and exon sequence are denoted with "small" and "capital" letters, respectively, and the intron-exon junction is marked with "|". The conventional denotation for pre-mRNA is further illustrated by a 30-mer sequence of [(5'→3') cucuuuggaucccag|GGUAACAAAUGAUGC (SEQ ID NO: 2)] spanning the junction of "intron 6" and "exon 7" in the human SNAP25 pre-mRNA. The exon numbering may vary depending on reported SNAP25 mRNA transcripts. Provision of the 30-mer SNAP25 sequence is to unequivocally identify the target splice site of the compound of Formula I regardless of the exon numbering of the SNAP25 mRNA.

Figure 5:
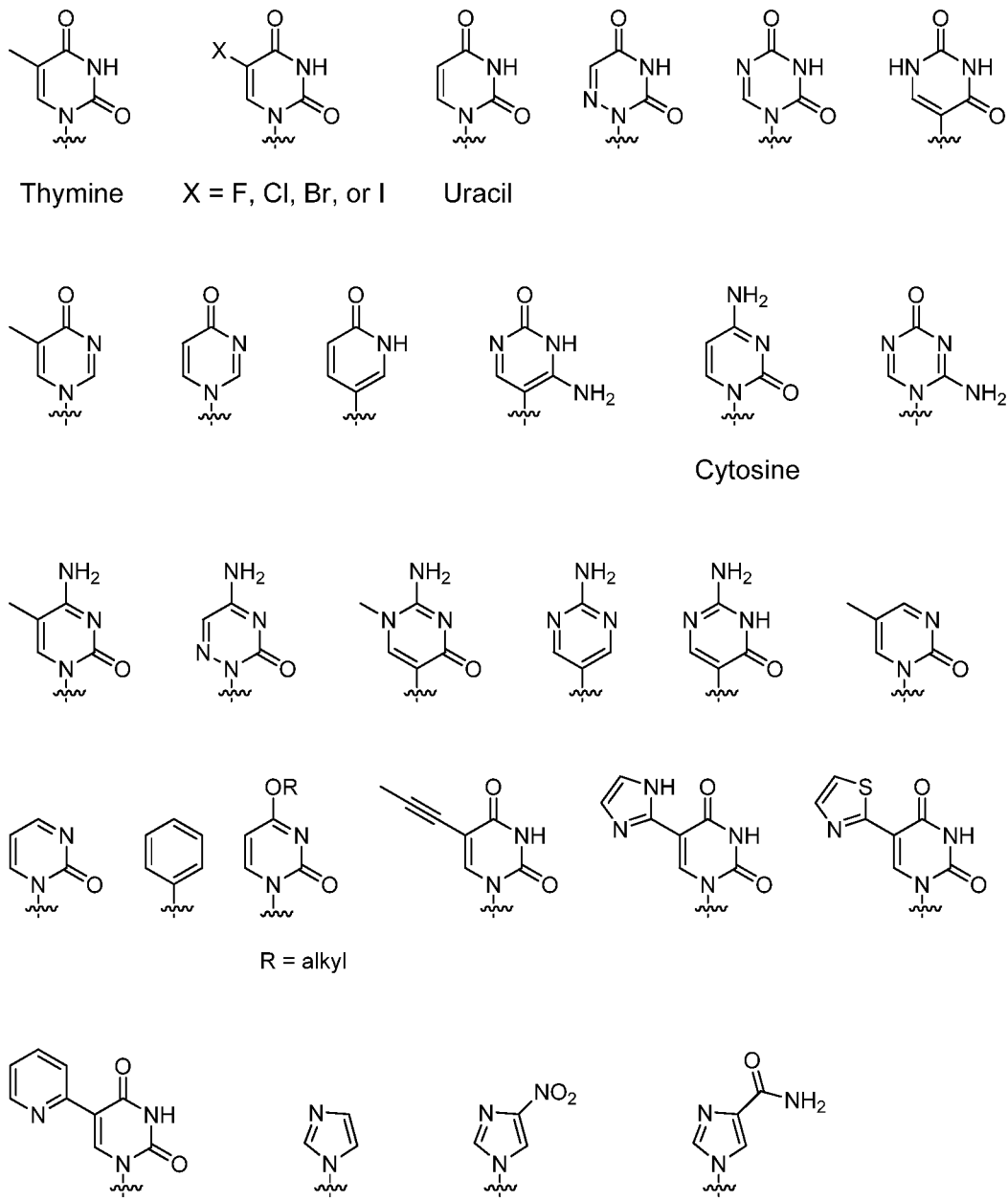
FIG. 5. Examples of natural or unnatural (modified) nucleobases selectable for the peptide nucleic acid derivative of Formula I.

The chemical structures of natural (i.e., naturally occurring) or unnatural (i.e., non-naturally occurring) nucleobases in the PNA derivative of Formula I are exemplified in FIG. 5. Natural or unnatural nucleobases of this invention comprise but are not limited to the nucleobases provided in FIG. 5. Provision of such natural and unnatural nucleobases is to illustrate the diversity of allowable nucleobases, and therefore should not be interpreted to limit the scope of the present invention.

Figure 6A:
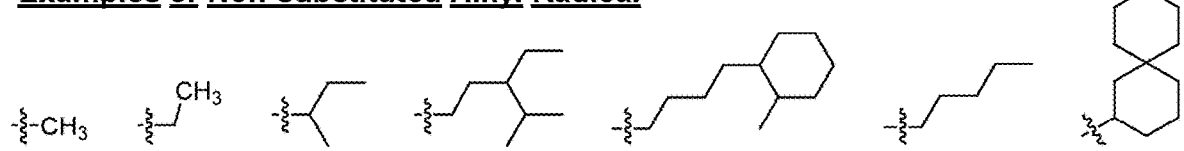
FIG. 6A. Examples for substituted or non-substituted alkyl radicals, which are selectable for the peptide nucleic acid derivative of Formula I.
Figure 6A:
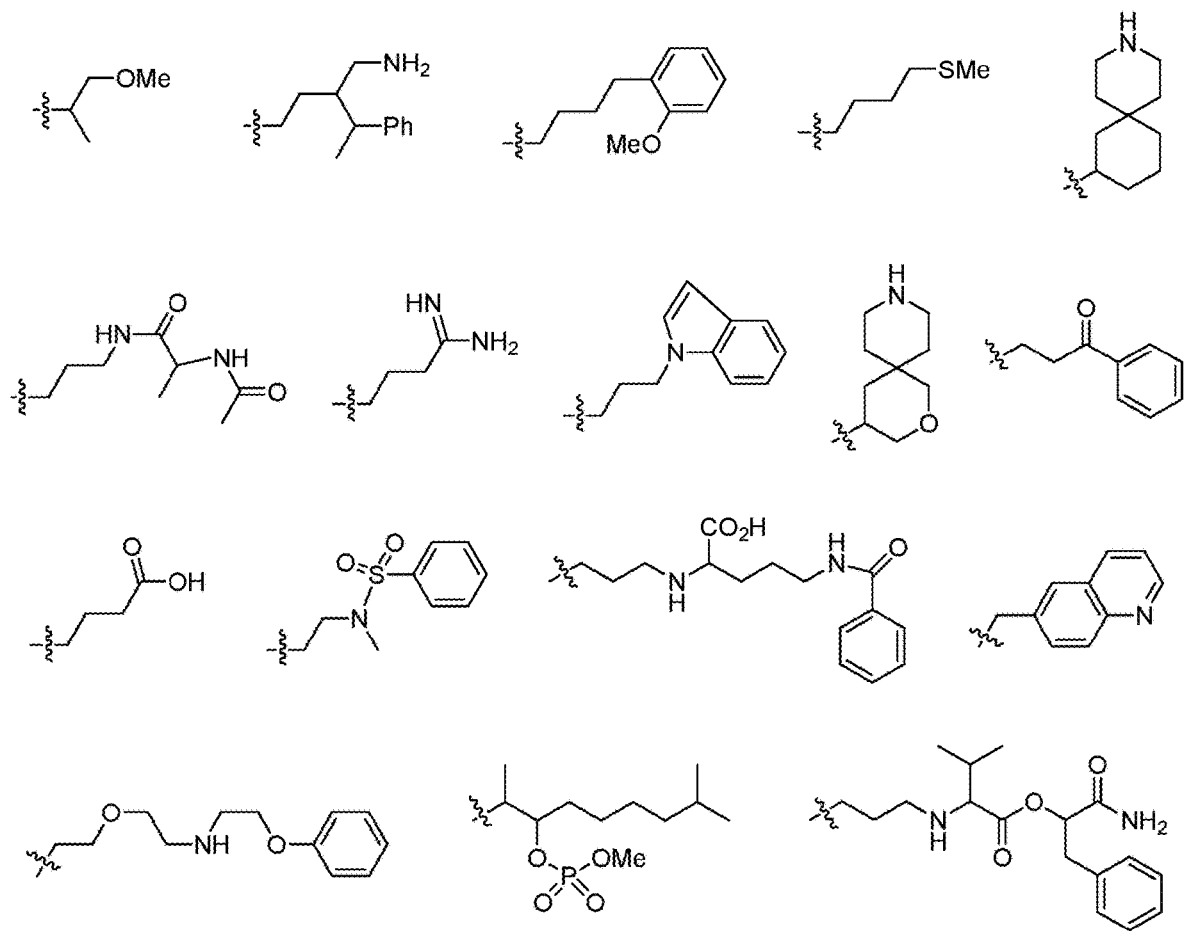
Figure 6B:
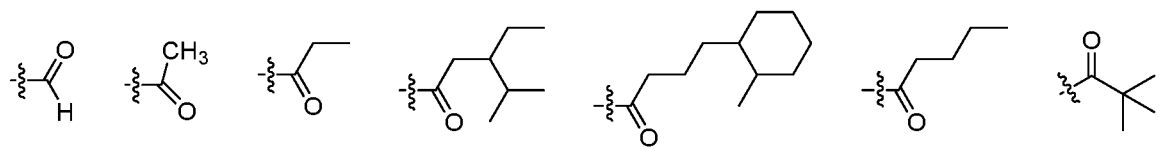
FIG. 6B. Examples for substituted or non-substituted alkylacyl, and substituted or non-substituted arylacyl radicals, which are selectable for the peptide nucleic acid derivative of Formula I.
Figure 6B:
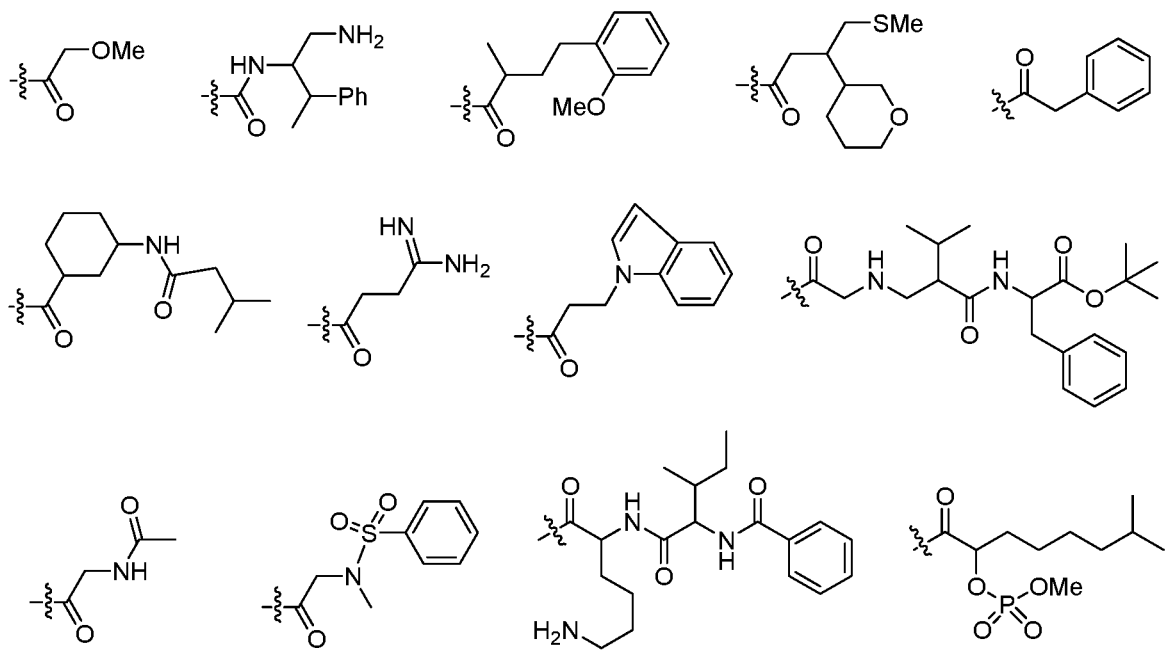
Figure 6B:
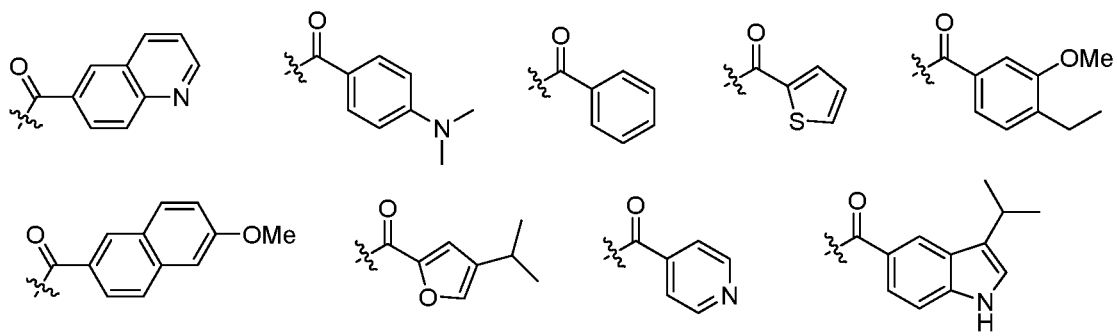
Figure 6C:
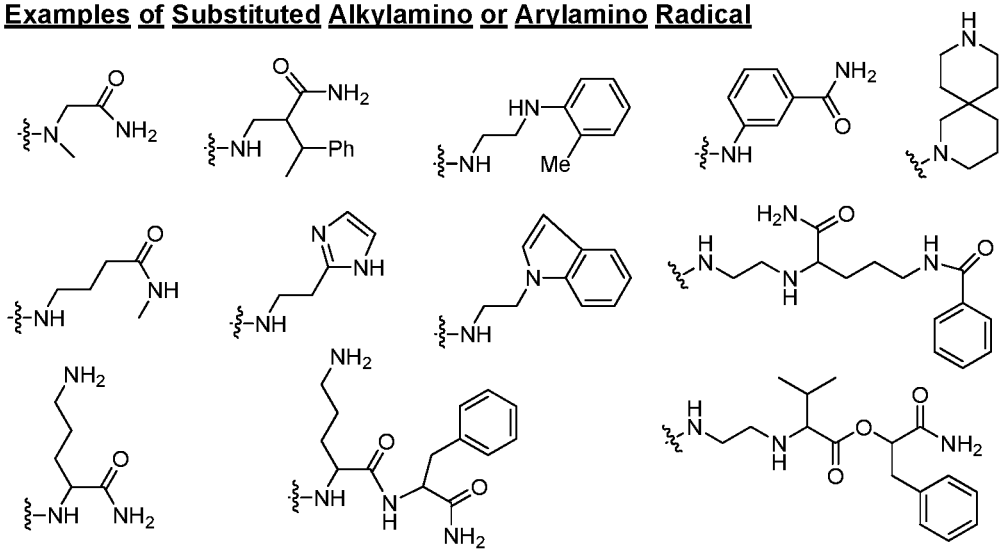
FIG. 6C. Examples for substituted alkylamino, substituted arylamino, substituted or non-substituted aryl, substituted or non-substituted alkylsulfonyl, substituted or non-substituted arylsulfonyl, substituted or non-substituted alkylphosphonyl, and substituted or non-substituted arylphosphonyl radicals, which are selectable for the peptide nucleic acid derivative of Formula I.
Figure 6C:
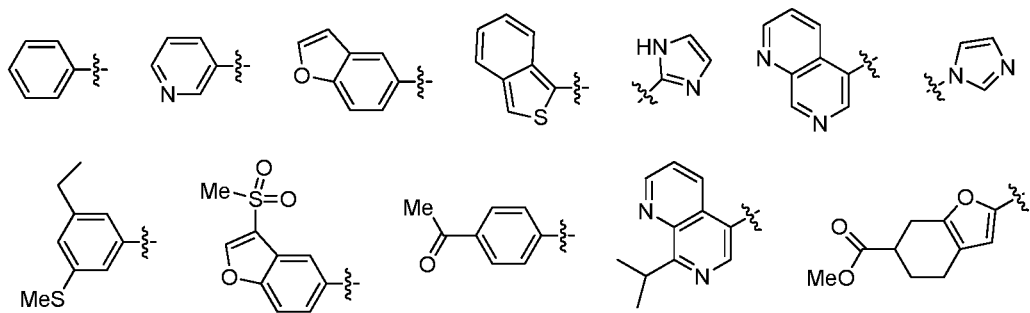
Figure 6C:
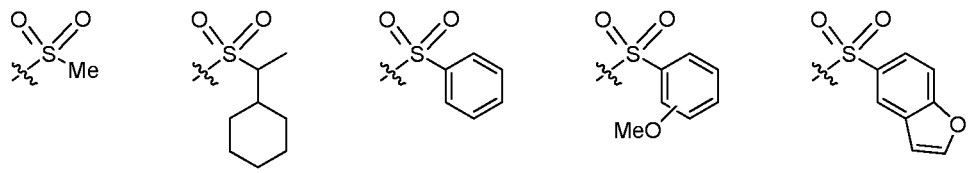
Figure 6C:
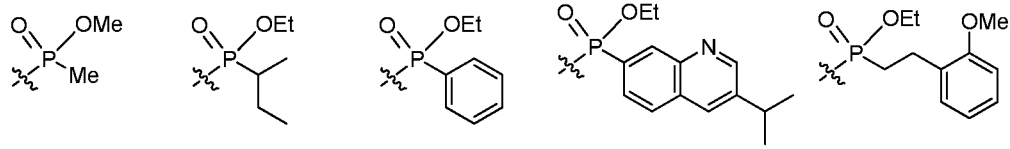
Figure 6D:
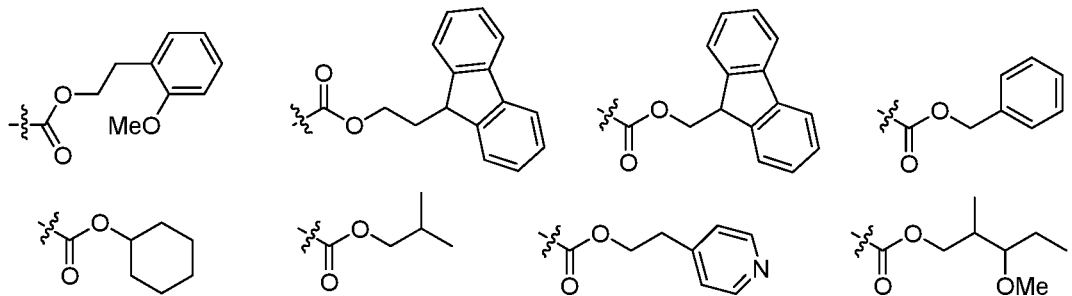
FIG. 6D. Examples for substituted or non-substituted alkyloxycarbonyl, substituted or non-substituted aryloxycarbonyl, substituted or non-substituted alkylaminocarbonyl, and substituted or non-substituted arylaminocarbonyl radicals, which are selectable for the peptide nucleic acid derivative of Formula I.
Figure 6D:
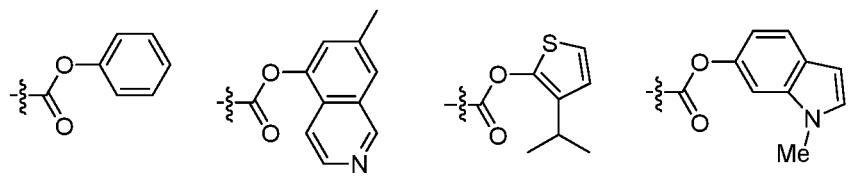
Figure 6D:
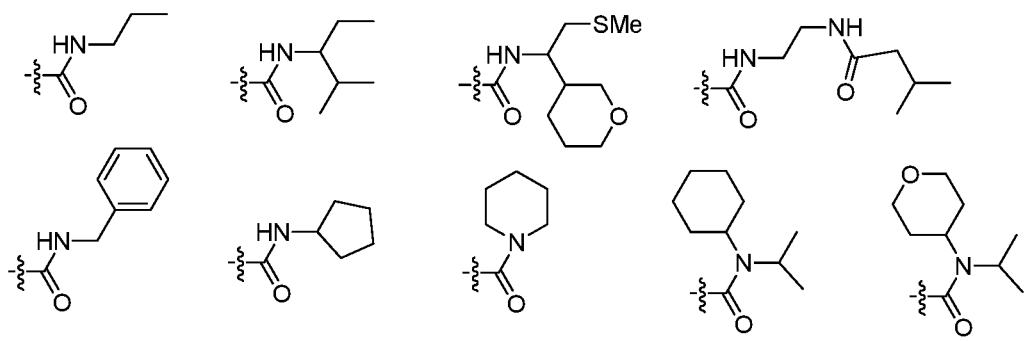
Figure 6D:
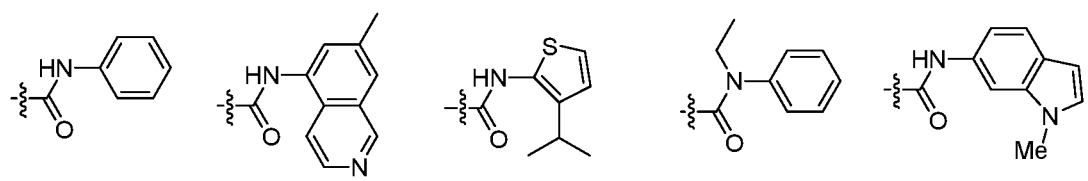
Figure 6E:
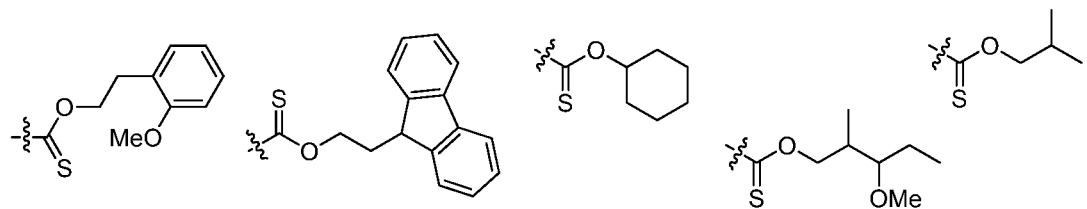
FIG. 6E. Examples for substituted or non-substituted alkyloxythiocarbonyl, substituted or non-substituted alkylaminothiocarbonyl, substituted or non-substituted arylaminothiocarbonyl, and substituted or non-substituted alkyloxythiocarbonyl radicals, which are selectable for the peptide nucleic acid derivative of Formula I.
Figure 6E:
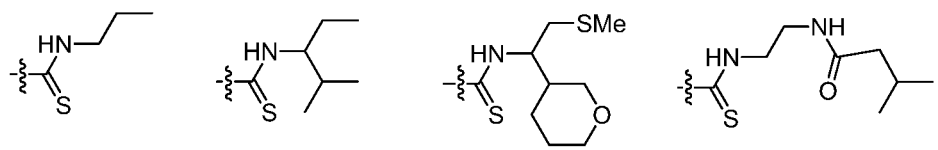
Figure 6E:
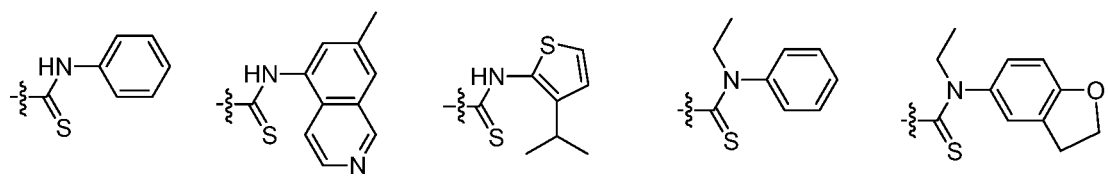
Figure 6E:
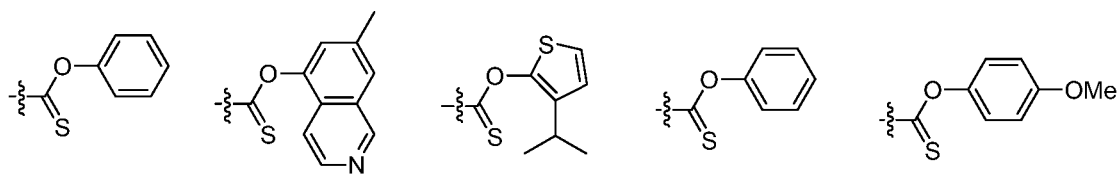

The substituents adopted to describe the PNA derivative of Formula I are exemplified in FIGS. 6A-E. FIG. 6A provides examples for substituted or non-substituted alkyl radicals. Substituted or non-substituted alkylacyl and substituted or non-substituted arylacyl radicals are exemplified in FIG. 6B. FIG. 6C illustrates examples for substituted alkylamino, substituted arylamino, substituted or non-substituted aryl, substituted or non-substituted alkylsulfonyl, substituted or non-substituted arylsulfonyl, substituted or non-substituted alkylphosphonyl, and substituted or non-substituted arylphosphonyl radicals. FIG. 6D provides examples for substituted or non-substituted alkyloxycarbonyl, substituted or non-substituted aryloxycarbonyl, substituted or non-substituted alkylaminocarbonyl, and substituted or non-substituted arylaminocarbonyl radicals. In FIG. 6E, are provided examples for substituted or non-substituted alkyloxythiocarbonyl, substituted or non-substituted alkylaminothiocarbonyl, substituted or non-substituted arylaminothiocarbonyl, and substituted or non-substituted alkyloxythiocarbonyl radicals. Provision of such substituents as examples is to illustrate the diversity of allowable substituents, and therefore should not be interpreted to limit the scope of the present invention. A skilled person in the field may readily figure out that the oligonucleotide sequence is the overriding factor for sequence specific binding of oligonucleotide to the target pre-mRNA sequence over substituents in the N-terminus or C-terminus.

The compound of Formula I tightly binds to the complementary DNA as exemplified in the prior art [PCT/KR2009/001256]. The duplex between the PNA derivative of Formula I and its full-length complementary DNA or RNA possesses a $T_m$ value too high to be reliably determined in aqueous buffer. The PNA compound of Formula I yields high $T_m$ values with complementary DNAs of shorter length.

The compound of Formula I tightly binds to the target 3' splice site of the human SNAP25 pre-mRNA transcribed from the human SNAP25 gene, and interferes with the formation of "splicesome early complex" involving the said compound's target exon. Since the compound of this invention sterically inhibits the formation of "splicesome early complex", the SNAP25 "exon 7" is spliced out to yield SNAP25 mRNA splice variant(s) lacking "exon 7". Consequently the compound of this invention induces the skipping of the SNAP25 "exon 7".

Owing to the said compound's strong affinity for the complementary pre-mRNA sequence, the compound of this invention may also tightly bind to a partially complementary pre-mRNA sequence with one or two mismatches, and induce the skipping of the target exon within the SNAP25 pre-mRNA.

The compound of Formula I possesses good cell permeability and can be readily delivered into cell as "naked" oligonucleotide as exemplified in the prior art [PCT/KR2009/001256]. Thus the compound of this invention induces the skipping of "exon 7" in the SNAP25 pre-mRNA to yield SNAP25 mRNA splice variant(s) lacking SNAP25 "exon 7" in cells treated with the compound of Formula I as "naked" oligonucleotide. The compound of Formula I does not require any means or formulations for delivery into cell to potently induce the skipping of the target exon in cells. The compound of Formula I readily induces the skipping of the SNAP25 "exon 7" in cells treated with the compound of this invention as "naked" oligonucleotide at sub-femtomolar concentration.

Owing to the good cell or membrane permeability, the PNA derivative of Formula I can be topically administered as "naked" oligonucleotide to induce the skipping of the SNAP25 "exon 7" in target skin. The said compound does not require a formulation to increase trans-dermal delivery into target tissue for the intended therapeutic or biological activity. Usually the compound of Formula I is dissolved in water and co-solvent, and topically or trans-dermally administered at subpicomolar concentration to elicit the desired therapeutic or biological activity around the dermal administration site. The compound of this invention does not need to be heavily or invasively formulated to elicit the topical therapeutic activity.

The compound of Formula I may be used as combined with a pharmaceutically acceptable acid or base including but not limited to sodium hydroxide, potassium hydroxide, hydrochloric acid, methanesulfonic acid, citric acid, trifluoroacetic acid, and so on.

The PNA derivative of Formula I or a pharmaceutically acceptable salt thereof can be administered to a subject in combination with a pharmaceutically acceptable adjuvant including but not limited to citric acid, hydrochloric acid, tartaric acid, stearic acid, polyethyleneglycol, polypropyleneglycol, ethanol, isopropanol, sodium bicarbonate, distilled water, preservative(s), and so on.

The compound of the present invention can be topically administered to a subject at a therapeutically or biologically effective concentration ranging from 1 aM (i.e., $10^{-18}$ M) to higher than 1 nM, which would vary depending on the dosing schedule, conditions or situations of the subject, and so on.

Preferred is a PNA derivative of Formula I, or a pharmaceutically acceptable salt thereof:
wherein,
n is an integer between 10 and 25;
the compound of Formula I possesses at least a 10-mer complementary overlap with a 14-mer pre-mRNA sequence of [(5'→3') AUCCCAGGGUAACA (SEQ ID NO: 1)] in the human SNAP25 pre-mRNA;
the compound of Formula I is fully complementary to the human SNAP25 pre-mRNA, or partially complementary to the human SNAP25 pre-mRNA with one or two mismatches;
$S_1$, $S_2$, . . . , $S_{n-1}$, $S_n$, $T_1$, $T_2$, . . . , $T_{n-1}$, and $T_n$ independently represent deuterido, hydrido, substituted or non-substituted alkyl, or substituted or non-substituted aryl radical;

X and Y independently represent hydrido, formyl, aminocarbonyl, aminothiocarbonyl, substituted or non-substituted alkyl, substituted or non-substituted aryl, substituted or non-substituted alkylacyl, substituted or non-substituted arylacyl, substituted or non-substituted alkyloxycarbonyl, substituted or non-substituted aryloxycarbonyl, substituted or non-substituted alkylaminocarbonyl, substituted or non-substituted arylaminocarbonyl, substituted or non-substituted alkylaminothiocarbonyl, substituted or non-substituted arylaminothiocarbonyl, substituted or non-substituted alkyloxythiocarbonyl, substituted or non-substituted aryloxythiocarbonyl, substituted or non-substituted alkylsulfonyl, substituted or non-substituted arylsulfonyl, substituted or non-substituted alkylphosphonyl radical, or substituted or non-substituted arylphosphonyl radical;

Z represents hydrido, hydroxy, substituted or non-substituted alkyloxy, substituted or non-substituted aryloxy, substituted or non-substituted amino, substituted or non-substituted alkyl, or substituted or non-substituted aryl radical;

$B_1, B_2, \ldots, B_{n-1}$, and $B_n$ are independently selected from natural nucleobases including adenine, thymine, guanine, cytosine and uracil, and unnatural nucleobases; and, at least four of $B_1, B_2, \ldots, B_{n-1}$, and $B_n$ are independently selected from unnatural nucleobases represented by Formula II, Formula III, or Formula IV:

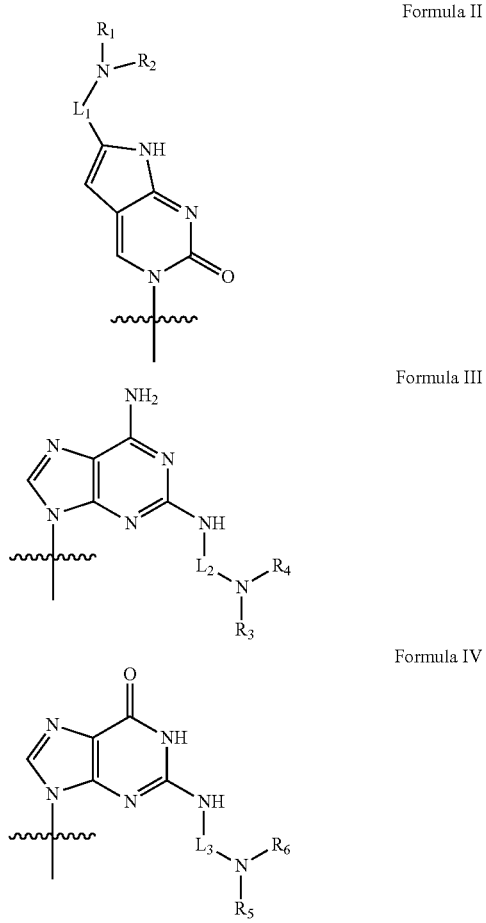

wherein, $R_1, R_2, R_3, R_4, R_5$ and $R_6$ are independently selected from hydrido, and substituted or non-substituted alkyl radical;

$L_1, L_2$ and $L_3$ are a covalent linker represented by Formula V covalently linking the basic amino group to the nucleobase moiety:

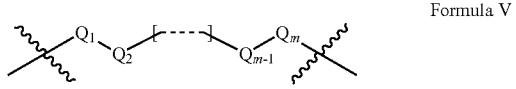

Formula V wherein, $Q_1$ and $Q_m$ are substituted or non-substituted methylene (—$CH_2$—) radical, and $Q_m$ is directly linked to the basic amino group;

$Q_2, Q_3, \ldots$, and $Q_{m-1}$ are independently selected from substituted or non-substituted methylene, oxygen (—O—), sulfur (—S—), and substituted or non-substituted amino radical [—N(H)—, or —N(substituent)-]; and, m is an integer between 1 and 15.

The condition adopted to describe Formula V that "m is an integer between 1 and 15" literally states that m is an integer selectable from a group of integers of 2, 3, 4, 5, 6, 7, 8, 9, 10, 11, 12, 13, and 14.

Of interest is a PNA oligomer of Formula I, or a pharmaceutically acceptable salt thereof:

wherein, n is an integer between 11 and 21;

the compound of Formula I possesses at least a 10-mer complementary overlap with a 14-mer pre-mRNA sequence of [(5'→3') AUCCCAGGGUAACA (SEQ ID NO: 1)] in the human SNAP25 pre-mRNA;

the compound of Formula I is fully complementary to the human SNAP25 pre-mRNA, or partially complementary to the human SNAP25 pre-mRNA with one or two mismatches;

$S_1, S_2, \ldots, S_{n-1}, S_n, T_1, T_2, \ldots, T_{n-1}$, and $T_n$ are hydrido radical;

X and Y independently represent hydrido, substituted or non-substituted alkyl, substituted or non-substituted aryl, substituted or non-substituted alkylacyl, substituted or non-substituted arylacyl, substituted or non-substituted alkyloxycarbonyl, substituted or non-substituted aryloxycarbonyl, substituted or non-substituted alkylaminocarbonyl, substituted or non-substituted arylaminocarbonyl, substituted or non-substituted alkylsulfonyl, or substituted or non-substituted arylsulfonyl radical;

Z represents substituted or non-substituted amino radical;

$B_1, B_2, \ldots, B_{n-1}$, and $B_n$ are independently selected from natural nucleobases including adenine, thymine, guanine, cytosine and uracil, and unnatural nucleobases;

at least four of $B_1, B_2, \ldots, B_{n-1}$, and $B_n$ are independently selected from unnatural nucleobases represented by Formula II, Formula III, or Formula IV;

$R_1, R_2, R_3, R_4, R_5$ and $R_6$ are independently selected from hydrido, and substituted or non-substituted alkyl radical;

$Q_1$ and $Q_m$ are substituted or non-substituted methylene radical, and $Q_m$ is directly linked to the basic amino group;

$Q_2, Q_3, \ldots$, and $Q_{m-1}$ are independently selected from substituted or non-substituted methylene, oxygen, and amino radical; and, m is an integer between 1 and 11.

Of particular interest is a PNA derivative of Formula I, or a pharmaceutically acceptable salt thereof:

wherein, n is an integer between 11 and 19;

the compound of Formula I possesses at least a 10-mer complementary overlap with a 14-mer pre-mRNA sequence of [(5'→3') AUCCCAGGGUAACA (SEQ ID NO: 1)] in the human SNAP25 pre-mRNA;

the compound of Formula I is fully complementary to the human SNAP25 pre-mRNA;

$S_1, S_2, \ldots, S_{n-1}, S_n, T_1, T_2, \ldots, T_{n-1}$, and $T_n$ are hydrido radical;

X and Y independently represent hydrido, substituted or non-substituted alkyl, substituted or non-substituted aryl, substituted or non-substituted alkylacyl, substituted or non-substituted arylacyl, substituted or non-substituted alkyloxycarbonyl, substituted or non-substituted alkylaminocarbonyl, substituted or non-substituted alkylsulfonyl, or substituted or non-substituted arylsulfonyl radical;

Z represents substituted or non-substituted amino radical;

$B_1, B_2, \ldots, B_{n-1}$, and $B_n$ are independently selected from natural nucleobases including adenine, thymine, guanine, cytosine and uracil, and unnatural nucleobases;

at least four of $B_1, B_2, \ldots, B_{n-1}$, and $B_n$ are independently selected from unnatural nucleobases represented by Formula II, Formula III, or Formula IV;

$R_1, R_2, R_3, R_4, R_5$ and $R_6$ are independently selected from hydrido, and substituted or non-substituted alkyl radical;

$Q_1$ and $Q_m$ are methylene radical, and $Q_m$ is directly linked to the basic amino group;

$Q_2, Q_3, \ldots$, and $Q_{m-1}$ are independently selected from methylene, oxygen, and amino radical; and, m is an integer between 1 and 9.

Of high interest is a PNA oligomer of Formula I, or a pharmaceutically acceptable salt thereof:

wherein, n is an integer between 11 and 19;

the compound of Formula I possesses at least a 10-mer complementary overlap with a 14-mer pre-mRNA sequence of [(5'→3') AUCCCAGGGUAACA (SEQ ID NO: 1)] in the human SNAP25 pre-mRNA;

the compound of Formula I is fully complementary to the human SNAP25 pre-mRNA;

$S_1, S_2, \ldots, S_{n-1}, S_n, T_1, T_2, \ldots, T_{n-1}$, and $T_n$ are hydrido radical;

X and Y independently represent hydrido, substituted or non-substituted alkyl, substituted or non-substituted aryl, substituted or non-substituted alkylacyl, substituted or non-substituted arylacyl, or substituted or non-substituted alkyloxycarbonyl radical;

Z represents substituted or non-substituted amino radical;

$B_1, B_2, \ldots, B_{n-1}$, and $B_n$ are independently selected from natural nucleobases including adenine, thymine, guanine, cytosine and uracil, and unnatural nucleobases;

at least four of $B_1, B_2, \ldots, B_{n-1}$, and $B_n$ are independently selected from unnatural nucleobases represented by Formula II, Formula III, or Formula IV;

$R_1, R_3$, and $R_5$ are hydrido radical, and $R_2, R_4$, and $R_6$ independently represent hydrido, or substituted or non-substituted alkyl radical;

$Q_1$ and $Q_m$ are methylene radical, and $Q_m$ is directly linked to the basic amino group;

$Q_2, Q_3, \ldots$, and $Q_{m-1}$ are independently selected from methylene, oxygen radical; and, m is an integer between 1 and 8.

Of higher interest is a PNA derivative of Formula I, or a pharmaceutically acceptable salt thereof:

wherein, n is an integer between 11 and 19;

the compound of Formula I possesses at least a 10-mer complementary overlap with a 14-mer pre-mRNA sequence of [(5'→3') AUCCCAGGGUAACA (SEQ ID NO: 1)] in the human SNAP25 pre-mRNA;

the compound of Formula I is fully complementary to the human SNAP25 pre-mRNA;

$S_1, S_2, \ldots, S_{n-1}, S_n, T_1, T_2, \ldots, T_{n-1}$, and $T_n$ are hydrido radical;

X and Y independently represent hydrido, substituted or non-substituted alkylacyl, substituted or non-substituted arylacyl, or substituted or non-substituted alkyloxycarbonyl radical;

Z represents substituted or non-substituted amino radical;

$B_1, B_2, \ldots, B_{n-1}$, and $B_n$ are independently selected from adenine, thymine, guanine, cytosine, and unnatural nucleobases;

at least five of $B_1, B_2, \ldots, B_{n-1}$, and $B_n$ are independently selected from unnatural nucleobases represented by Formula II, Formula III, or Formula IV;

$R_1, R_2, R_3, R_4, R_5$, and $R_6$ are hydrido radical;

$Q_1$ and $Q_m$ are methylene radical, and $Q_m$ is directly linked to the basic amino group;

$Q_2, Q_3, \ldots$, and $Q_{m-1}$ are independently selected from methylene, and oxygen radical; and, m is an integer between 1 and 8.

Of highest interest is a PNA derivative of Formula I, or a pharmaceutically acceptable salt thereof:

wherein, n is an integer between 11 and 19;

the compound of Formula I possesses at least a 10-mer complementary overlap with a 14-mer pre-mRNA sequence of [(5'→3') AUCCCAGGGUAACA (SEQ ID NO: 1)] in the human SNAP25 pre-mRNA;

the compound of Formula I is fully complementary to the human SNAP25 pre-mRNA;

$S_1, S_2, \ldots, S_{n-1}, S_n, T_1, T_2, \ldots, T_{n-1}$, and $T_n$ are hydrido radical;

X is hydrido radical;

Y represents substituted or non-substituted alkylacyl, substituted or non-substituted arylacyl, or substituted or non-substituted alkyloxycarbonyl radical;

Z represents substituted or non-substituted amino radical;

$B_1, B_2, \ldots, B_{n-1}$, and $B_n$ are independently selected from adenine, thymine, guanine, cytosine, and unnatural nucleobases;

at least five of $B_1, B_2, \ldots, B_{n-1}$, and $B_n$ are independently selected from unnatural nucleobases represented by Formula II, Formula III, or Formula IV;

$R_1, R_2, R_3, R_4, R_5$, and $R_6$ are hydrido radical;

$L_1$ represents —(CH$_2$)$_2$—O—(CH$_2$)$_2$—, —CH$_2$—O—(CH$_2$)$_2$—, —CH$_2$—O—(CH$_2$)$_3$—, —CH$_2$—O—(CH$_2$)$_4$—, or —CH$_2$—O—(CH$_2$)$_5$— with the right end is directly linked to the basic amino group; and, $L_2$ and $L_3$ are independently selected from —(CH$_2$)$_2$—, —(CH$_2$)$_3$—, —(CH$_2$)$_4$—, —(CH$_2$)$_5$—, —(CH$_2$)$_6$—, —(CH$_2$)$_7$—, —(CH$_2$)$_8$—, —(CH$_2$)$_2$—O—(CH$_2$)$_2$—, —(CH$_2$)$_3$—O—(CH$_2$)$_2$—, and —(CH$_2$)$_2$—O—(CH$_2$)$_3$— with the right end is directly linked to the basic amino group.

Of specific interest is a PNA derivative of Formula I which is selected from the group of compounds provided below, or a pharmaceutically acceptable salt thereof:

(N→C) Fethoc-A(6)TT-TG(6)T-TA(6)C-CC(1O2)T-GG(6)G-A(6)-NH$_2$;

(N→C) Fethoc-A(6)TC-TG(6)T-TA(6)C-CC(1O2)T-GG(6)G-A(6)-NH$_2$;

(N→C) Piv-A(6)TT-TG(6)T-TA(6)C-CC(1O2)T-GG(6)G-A(6)-NH$_2$;

(N→C) Fethoc-A(6)TT-TG(6)T-TA(2O2)C-CC(1O2)T-GG(5)G-A(5)-NH$_2$;

(N→C) Fmoc-Lys-A(6)TT-TG(6)T-TA(6)C-CC(1O2)T-GG(6)G-A(6)-NH$_2$;

(N→C) Fethoc-TG(5)T-TA(6)C-C(1O2)CT-GG(5)G-A(5)-NH$_2$;

(N→C) Fethoc-TG(5)T-TA(6)C-C(1O2)CT-GG(5)T-A(5)-NH$_2$;

(N→C) Fethoc-TG(5)T-TA(6)C-C(1O3)CT-GG(5)G-A(5)-NH₂;
(N→C) Fethoc-Lys-Leu-TG(5)T-TA(5)C-CC(1O2)T-GG(5)G-A(2O2)T-Lys-NH₂;
(N→C) H-TG(5)T-TA(5)C-CC(1O2)T-GG(3)G-A(5)T-NH₂;
(N→C) Benzoyl-TG(5)T-TA(6)C-C(1O3)CT-GG(5)G-A(5)-Val-Lys-NH₂;
(N→C) Benzoyl-TG(5)T-TA(5)C-CC(1O3)T-GG(5)G-A(5)T-NH₂;
(N→C) n-Hexanoyl-TG(5)T-TA(8)C-CC(1O2)T-GG(5)G-A(5)T-NH₂;
(N→C) n-Propyl-TG(5)T-TA(6)C-C(1O3)CT-GG(5)G-A(5)-NH₂;
(N→C) Ac-TG(5)T-TA(6)C-C(1O3)CT-GG(5)G-A(5)-NH₂;
(N→C) [N-(2-Phenylethyl)amino]carbonyl-TG(5)T-TA(4)C-CC(1O2)T-GG(5)G-A(5)T-NH₂;
(N→C) n-Propyl-TG(2O2)T-TA(5)C-CC(2O2)T-GG(5)G-A(5)T-NH₂;
(N→C) FAM-HEX-HEX-TG(2O2)T-TA(5)C-CC(2O2)T-GG(5)G-A(5)T-NH₂;
(N→C) n-Propyl-TG(2O2)T-TA(5)C-CC(2O2)T-GG(5)G-A(5)T-Arg-NH₂;
(N→C) n-Benzoyl-Gly-TG(2O2)T-TA(5)C-CC(2O2)T-GG(5)G-A(5)T-NH₂;
(N→C) N-Me-N-Phenyl-TG(5)T-TA(5)C-CC(1O5)T-GG(5)G-A(5)T-NH₂;
(N→C) p-Toluenesulfonyl-TG(2O3)T-TA(5)C-CC(1O2)T-GG(5)G-A(5)T-Lys-NH₂
(N→C) Fethoc-TG(5)T-TA(6)C-C(1O2)CT-GG(5)G-A(6)T-NH₂;
(N→C) Bezenesulfonyl-TG(5)T-TA(2O3)C-CC(1O5)T-GG(5)G-A(6)T-NH₂;
(N→C) Phenyl-TG(5)T-TA(6)C-C(1O2)CT-GG(5)G-A(6)T-NH₂;
(N→C) Fethoc-TG(5)G-TA(5)C-C(1O2)CT-TG(5)G-A(5)T-NH₂;
(N→C) Fethoc-TG(5)T-AA(5)C-CC(1O2)T-GG(5)T-A(5)T-NH₂;
(N→C) Fethoc-TG(6)T-TA(3)C-CC(1O5)T-GG(6)G-A(3)T-NH₂;
(N→C) Fethoc-G(5)TT-A(5)CC(1O2)-CTG-G(5)GA(5)-TC(1O2)-NH₂;
(N→C) Benzyl-G(5)TT-A(5)CC(1O2)-CTG-G(5)GA(5)-TC(1O2)-NH₂;
(N→C) Fethoc-GTT-A(3)CC(1O5)-CTG(6)-GGA(3)-TC(1O5)-NH₂;
(N→C) Fethoc-TA(5)C-C(1O2)CT(1O5)-GG(5)G-A(5)TC-C(1O2)A-NH₂;
(N→C) Fmoc-Leu-TA(4)C-C(1O3)CT-GG(5)G-A(4)TC-C(1O3)A-NH₂;
(N→C) Fethoc-C(1O2)AT-TTG(6)-TTA(5)-CCC(1O2)-TG(6)-NH₂;
(N→C) Fethoc-CA(6)T-TTG(5)-TTA(5)-CCC(1O2)-TG(5)-NH₂;
(N→C) Fethoc-A(6)TT-TG(5)T-TA(5)C-C(1O2)CT-G(5)-NH₂;
(N→C) Fethoc-CA(6)T-CA(6)T-TTG(5)-TTA(5)-CCC(1O2)-TG(5)-NH₂;
(N→C) Fethoc-A(5)TT-TG(5)T-TA(5)C-CC(1O2)T-GG(5)G-A(5)-NH₂;
(N→C) Fethoc-A(6)TT-TG(5)T-TA(6)C-C(1O2)CT-GG(5)G-A(5)-NH₂; and
(N→C) Fethoc-A(6)TT-TG(5)T-TA(6)C-C(1O2)CT-G(5)-NH₂:
wherein,
A, G, T, and C are PNA monomers with a natural nucleobase of adenine, guanine, thymine, and cytosine, respectively;

C(pOq), A(p), A(pOq), G(p), and G(pOq) are PNA monomers with an unnatural nucleobase represented by Formula VI, Formula VII, Formula VIII, Formula IX, and Formula X, respectively;

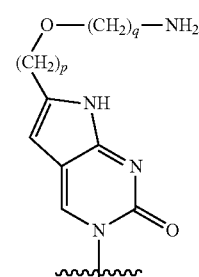

Formula VI

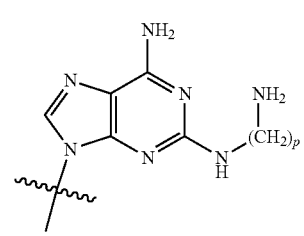

Formula VII

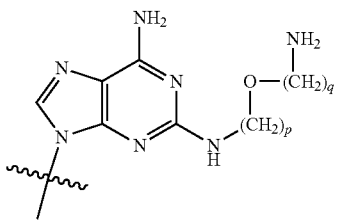

Formula VII

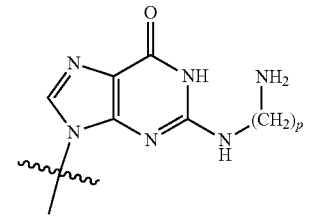

Formula IX

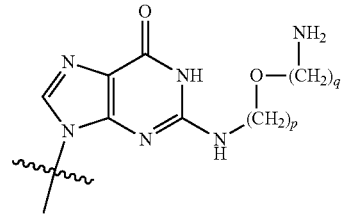

Formula X wherein,
p and q are integers; and,
the abbreviations for the N- and C-terminus substituents are specifically defined as follows: "Fmoc-" is the abbreviation for "[(9-fluorenyl)methyloxy]carbonyl-"; "Fethoc-" for "[2-(9-fluorenyl)ethyl-1-oxy]carbonyl"; "Ac-" for "acetyl-"; "Benzoyl-" for "benzenecabonyl-"; "Piv-" for "pivalyl-"; "n-Propyl-" for "1-(n-propyl)-"; "H-" for "hydrido-" group; "p-Toluenesulfonyl" for "(4-methylbenzene)-1-sulfonyl-"; "-Lys-" for amino acid residue "lysine"; "-Val-" for amino acid residue "valine"; "-Leu-" for amino acid residue "leucine"; "-Arg-" for amino acid residue "arginine"; "-Gly-" for amino acid residue "glycine"; "[N-(2-Phenylethyl)amino]carbonyl-" for "[N-1-(2-phenylethyl) amino]carbonyl-"; "Benzyl-" for "1-(phenyl)methyl-"; "Phenyl-" for "phenyl-"; "Me-" for "methyl-"; "-HEX-" for "6-amino-1-hexanoyl-", "FAM-" for "5, or 6-fluorescein-carbonyl-(isomeric mixture)", and "—$NH_2$" for non-substituted "-amino" group.

Figure 7:
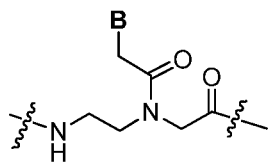
FIG. 7. Chemical structures for the PNA monomers abbreviated as A (adenine), G (guanine), T (thymine), C (cytosine), C(pOq), A(p), A(pOq), G(p), and G(pOq).
Figure 7:
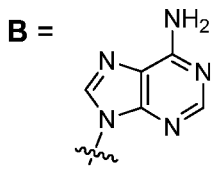
Figure 7:
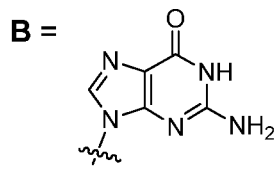
Figure 7:
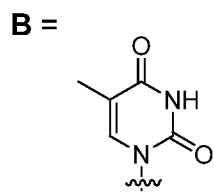
Figure 7:
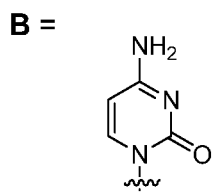
Figure 7:
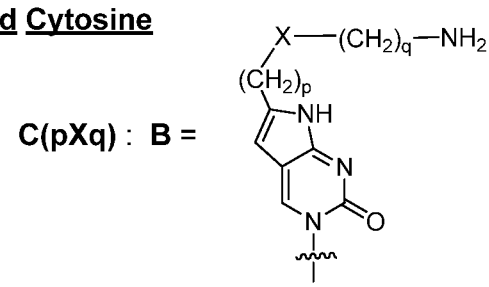
Figure 7:
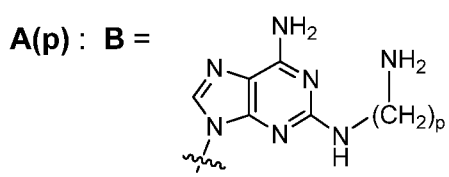
Figure 7:
Figure 7:
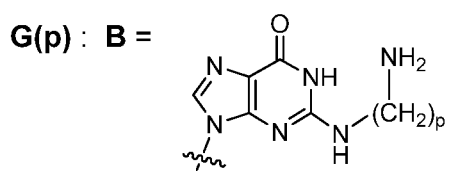
Figure 7:
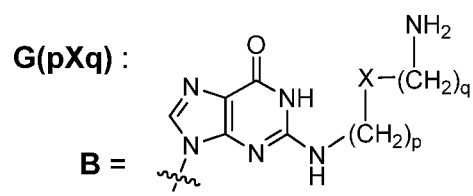

FIG. 7 collectively provides the chemical structures for the PNA monomers abbreviated as A, G, T, C, C(pOq), A(p), A(pOq), G(p), and G(pOq). As discussed in the prior art [PCT/KR2009/001256], C(pOq) is regarded as a modified PNA monomer corresponding to "cytosine" due to its preferred hybridization to "guanine". A(p) and A(pOq) are taken as modified PNA monomers acting as "adenine" for their tight affinity for "thymine". Likewise G(p) and G(pOq) are considered to be modified PNA monomers equivalent to "guanine" owing to their productive base pairing with "cytosine".

Figure 8:
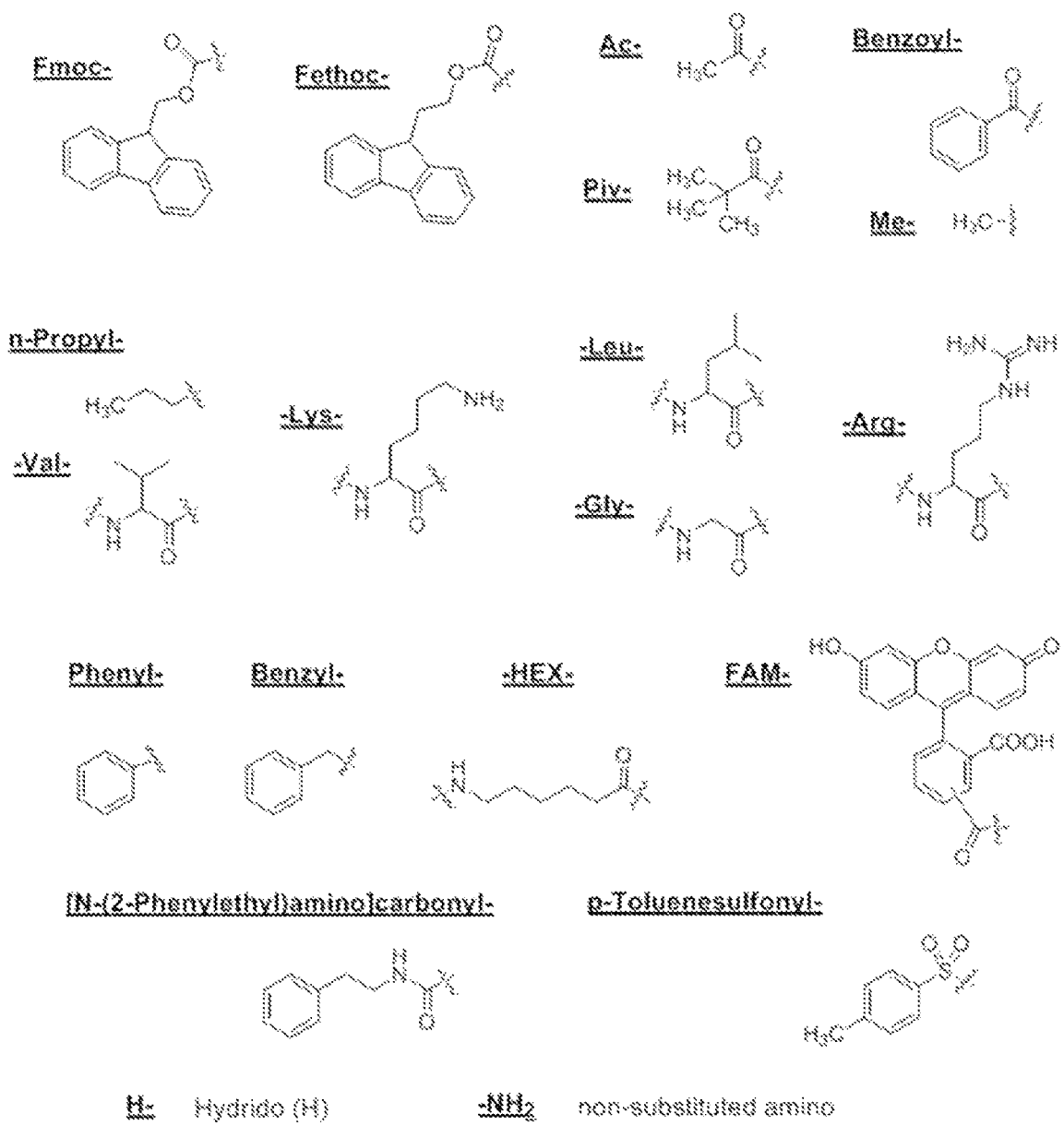
FIG. 8. Chemical structures for the abbreviations used to describe substituents for the N-terminal or C-terminal of PNA.

FIG. 8 unequivocally provides the chemical structures for a variety of abbreviations for substituents used to introduce diversities in the N-terminus or C-terminus of the PNA derivative of Formula I in this invention.

Figure 9:
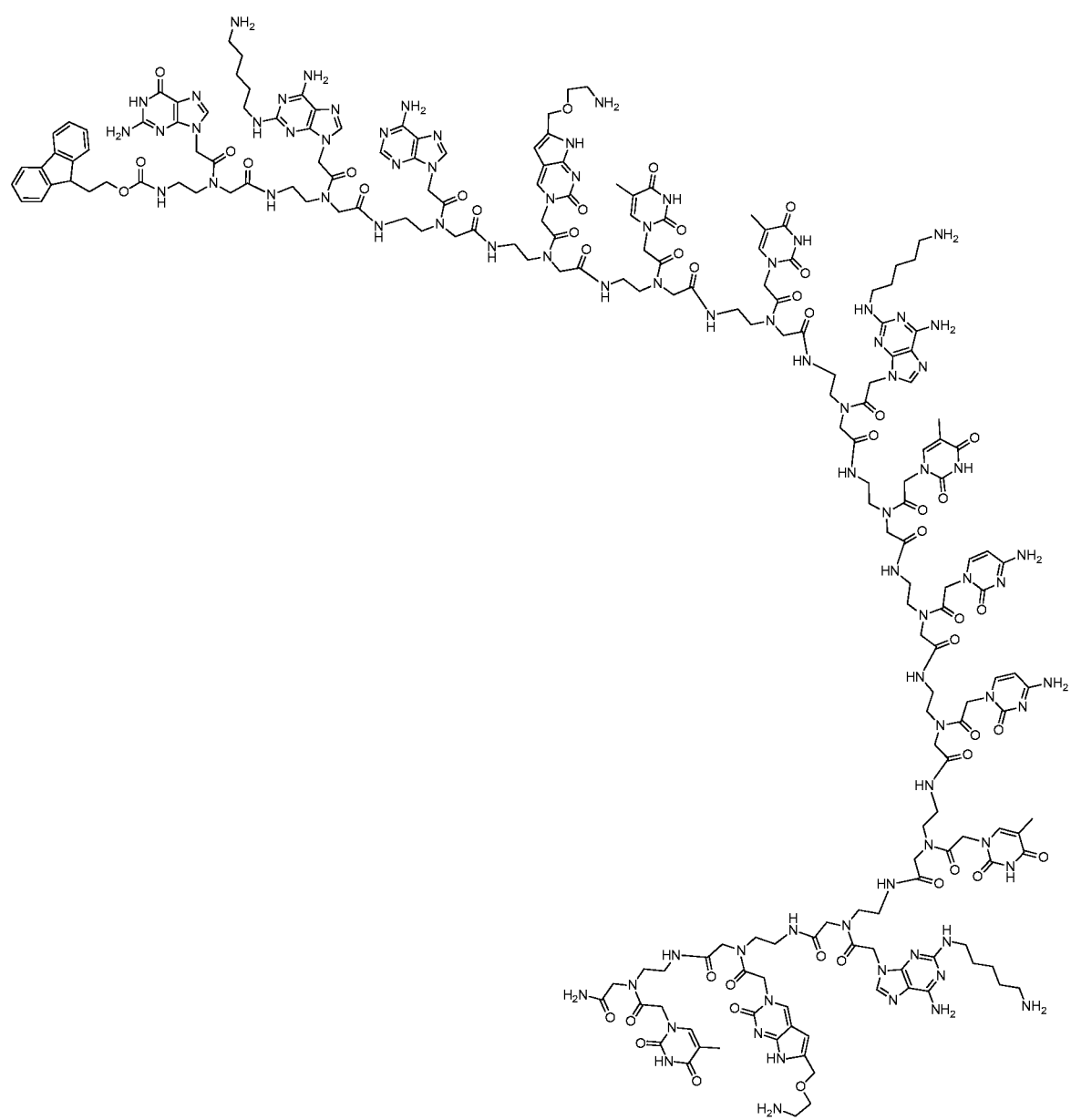
FIG. 9. Chemical structure for the 14-mer PNA derivative abbreviated as "(N→C) Fethoc-GA(5)A-C(1O2)TT-A(5)TC-CTA(5)-C(1O2)T-NH$_2$".
Figure 10:
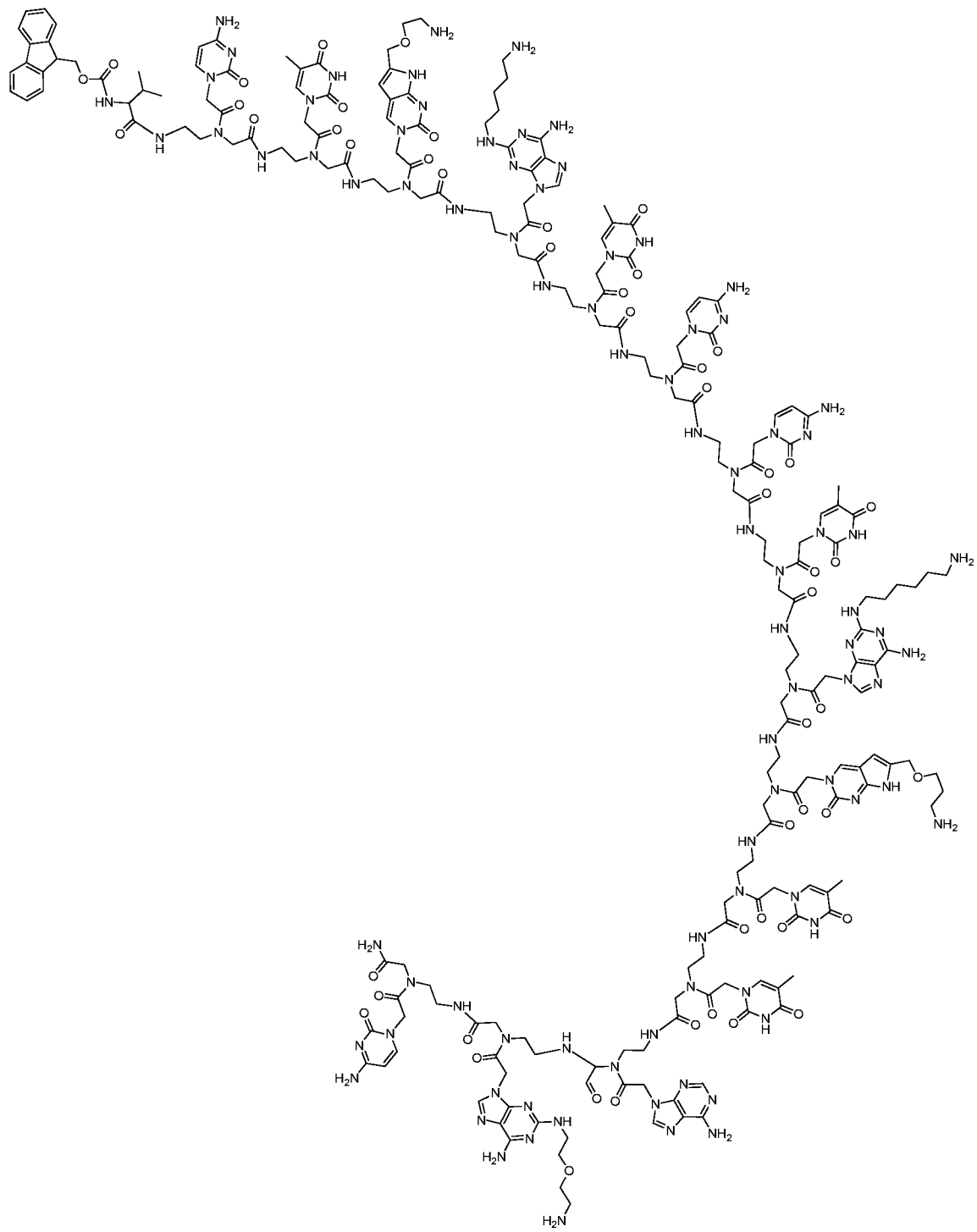
FIG. 10. Chemical structure for the 15-mer PNA derivative abbreviated as "(N→C) Fmoc-Val-CTC(1O2)-A(5)TC-CTA(6)-C(1O3)TT-AA(2O2)C—NH$_2$".

In order to illustrate the abbreviations employed for such PNA derivatives, the chemical structure for a 14-mer PNA derivative abbreviated as "(N→C) Fethoc-GA(5)A-C(1O2)TT-A(5)TC-CTA(5)-C(1O2)T-$NH_2$" is provided in FIG. 9. As another illustration, the chemical structure for a 15-mer PNA derivative abbreviated as "(N→C) Fmoc-Val-CTC(1O2)-A(5)TC-CTA(6)-C(1O3)TT-AA(2O2)C—$NH_2$" is provided in FIG. 10.

A 16-mer PNA sequence of "(N→C) Fethoc-A(6)TT-TG(6)T-TA(6)C-CC(1O2)T-GG(6)G-A(6)-$NH_2$" is equivalent to the DNA sequence of "(5'→3') ATT-TGT-TAC-CCT-GGG-A (SEQ ID NO: 3)" for complementary binding to pre-mRNA. The 16-mer PNA has a 16-mer complementary overlap with the human SNAP25 pre-mRNA as marked "bold" and "underlined" in the 30-mer pre-mRNA sequence of

[(5' → 3') cucuuugga<u>ucccag</u> | GGUAACAAAUGAUGC (SEQ ID NO: 2)]

spanning the junction of "intron 6" and "exon 7" in the human SNAP25 pre-mRNA.

A 14-mer PNA sequence of "(N→C) Fmoc-Leu-TA(4)C-C(1O3)CT-GG(5)G-A(4)TC-C(1O3)A-$NH_2$" is equivalent to the DNA sequence of "(5'→3') TAC-CCT-GGG-ATC-CA (SEQ ID NO: 4)" for complementary binding to pre-mRNA. The 14-mer PNA has a 14-mer complementary overlap with the human SNAP25 pre-mRNA as marked "bold" and "underlined" in the 30-mer pre-mRNA sequence of

[(5' → 3') cucuu<u>uggaucccag</u> | GGUAACAAAUGAUGC (SEQ ID NO: 2)].

A 16-mer PNA sequence of "(N→C) Fethoc-A(6)TC-TG(6)T-TA(6)C-CC(1O2)T-GG(6)G-A(6)-$NH_2$" is equivalent to the DNA sequence of "(5'→3') ATC-TGT-TAC-CCT-GGG-A (SEQ ID NO: 5)" for complementary binding to pre-mRNA. The 16-mer PNA has a 15-mer complementary overlap with the 16-mer sequence as marked in "bold" and "underlined" in the 30-mer pre-mRNA sequence of [(5'→3') cucuuuggaucccag|GGUAACA"A"AUGAUGC (SEQ ID NO: 2)], in which the single mismatch is marked with a quote sign (" "). The 16-mer PNA is partially complementary to the 3' splice site of the SNAP25 "exon 7" with a single mismatch with "exon 7".

DETAILED DESCRIPTION OF INVENTION

General Procedures for Preparation of PNA Oligomers

Figure 11:
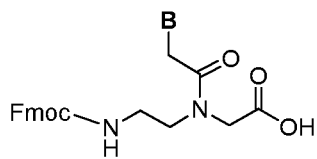
FIG. 11. Chemical structures for exemplary Fmoc-PNA monomers used to synthesize the PNA derivatives of this invention.
Figure 11:
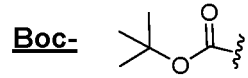
Figure 11:
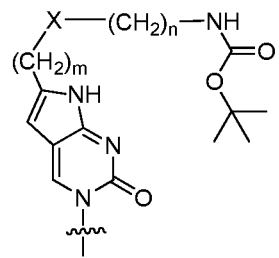
Figure 11:
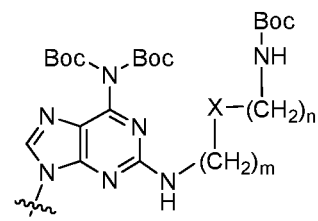
Figure 11:
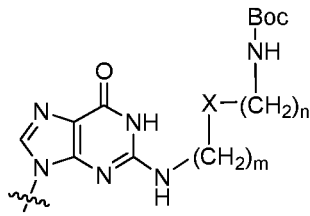

PNA oligomers were synthesized by solid phase peptide synthesis (SPPS) based on Fmoc-chemistry according to the method disclosed in the prior art [U.S. Pat. No. 6,133,444; WO 96/40685] with minor modifications if needed. The solid support employed in this study was H-Rink Amide-ChemMatrix purchased from PCAS BioMatrix Inc. (Quebec, Canada). Fmoc-PNA monomers with a modified nucleobase were synthesized as described in the prior art [PCT/KR 2009/001256] or with minor modifications. Such Fmoc-PNA monomers with a modified nucleobase and Fmoc-PNA monomers with a natural nucleobase were used to synthesize the PNA derivatives of the present invention. The Fmoc-PNA monomers with a modified nucleobase are provided in FIG. 11. To a skilled person in the field, however, there are lots of minor variations obviously possible for the protecting groups on such PNA monomers. Thus the Fmoc-PNA monomers in FIG. 11 should be taken as examples, and therefore should not be taken to limit the scope of the present invention. PNA oligomers were purified by $C_{18}$-reverse phase HPLC (water/acetonitrile or water/methanol with 0.1% TFA) and characterized by mass spectrometry including ESI/TOF/MS.

Figure 12:
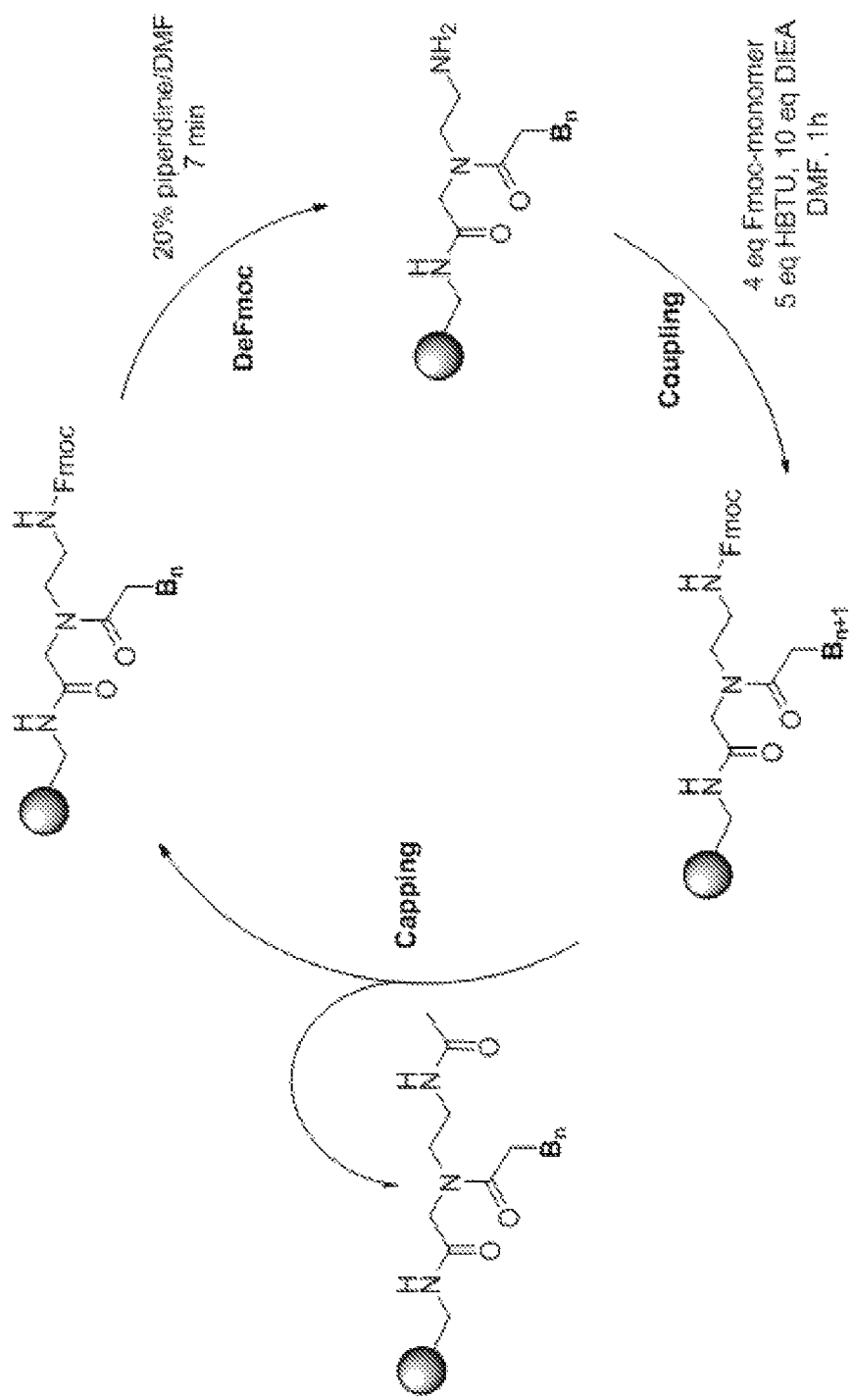
FIG. 12. Schematic illustration of a typical monomer elongation cycle adopted in SPPS of this invention.

FIG. 12 schematically illustrates a typical monomer elongation cycle adopted in the SPPS of this study, and the synthetic details are provided as below. To a skilled person in the field, however, there are lots of minor variations obviously possible in effectively running such SPPS reactions on an automatic peptide synthesizer or manual peptide synthesizer. Each reaction step is briefly provided as follows.

[Activation of H-Rink-ChemMatrix Resin] 0.01 mmol (ca 20 mg resin) of the ChemMatrix resin in 1.5 mL 20% piperidine/DMF was vortexed in a libra tube for 20 min, and the DeFmoc solution was filtered off. The resin was washed for 30 sec each in series with 1.5 mL methylene chloride (MC), 1.5 mL dimethylformamide (DMF), 1.5 mL MC, 1.5 mL DMF, and 1.5 mL MC. The resulting free amines on the solid support were subjected to coupling either with an Fmoc-PNA monomer or with an Fmoc-protected amino acid derivative.

[DeFmoc] The resin was vortexed in 1.5 mL 20% piperidine/DMF for 7 min, and the DeFmoc solution was filtered off. The resin was washed for 30 sec each in series with 1.5 mL MC, 1.5 mL DMF, 1.5 mL MC, 1.5 mL DMF, and 1.5 mL MC. The resulting free amines on the solid support were immediately subjected to coupling with an Fmoc-PNA monomer.

[Coupling with Fmoc-PNA Monomer] The free amines on the solid support were coupled with an Fmoc-PNA monomer as follows. 0.04 mmol of an Fmoc-PNA monomer, 0.05 mmol HBTU [2-(1H-benzotriazol-1-yl)-1,1,3,3-tetramethyluronium hexafluoro-phosphate], and 10 mmol DIEA (N,N-diisopropylethylamine) were incubated for 2 min in 1 mL anhydrous DMF, and added to the resin with free amines. The resin solution was vortexed for 1 hour and the reaction medium was filtered off. Then the resin was washed for 30 sec each in series with 1.5 mL MC, 1.5 mL DMF, and 1.5 mL MC.

[Capping] Following the coupling reaction, the unreacted free amines were capped by shaking for 5 min in 1.5 mL capping solution (5% acetic anhydride and 6% 2,6-leutidine in DMF). Then the capping solution was filtered off and washed for 30 sec each in series with 1.5 mL MC, 1.5 mL DMF, and 1.5 mL MC.

[Introduction of "Fethoc-" Radical in N-Terminus] "Fethoc-" radical was introduced to the N-terminus by reacting the free amines on the resin with "Fethoc-OSu" under usual basic coupling conditions. The chemical structure of "Fethoc-OSu" [CAS No. 179337-69-0, $C_{20}H_{17}NO_5$, MW 351.36] is provided as follows.

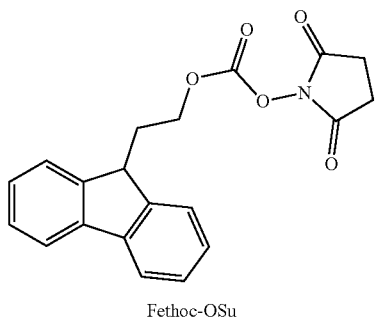 [SMILES: O=C(OCCC1c2ccccc2-c2ccccc21)ON1C(=O)CCC1=O]

Fethoc-OSu

[Cleavage from Resin] PNA oligomers bound to the resin were cleaved from the resin by shaking for 3 hours in 1.5 mL cleavage solution (2.5% tri-isopropylsilane and 2.5% water in trifluoroacetic acid). The resin was filtered off and the filtrate was concentrated under reduced pressure. The resulting residue was triturated with diethylether and the resulting precipitate was collected by filtration for purification by reverse phase HPLC.

Figure 13A:
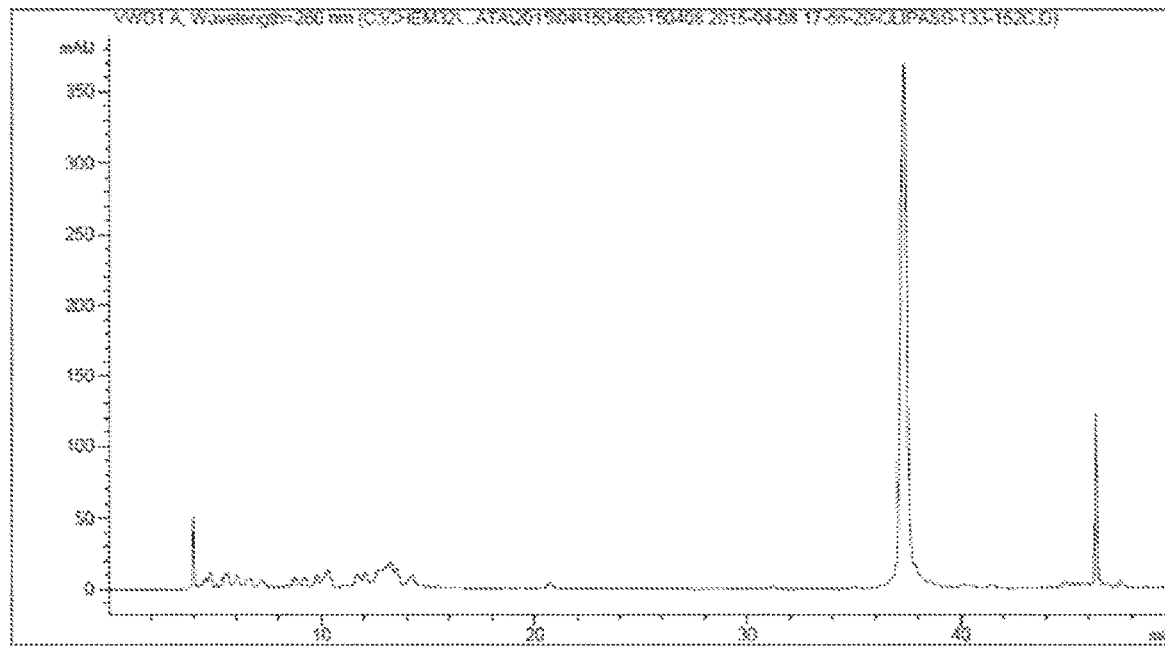
FIG. 13A. $C_{18}$-reverse phase HPLC chromatogram for "ASO 1" before HPLC purification.
Figure 13B:
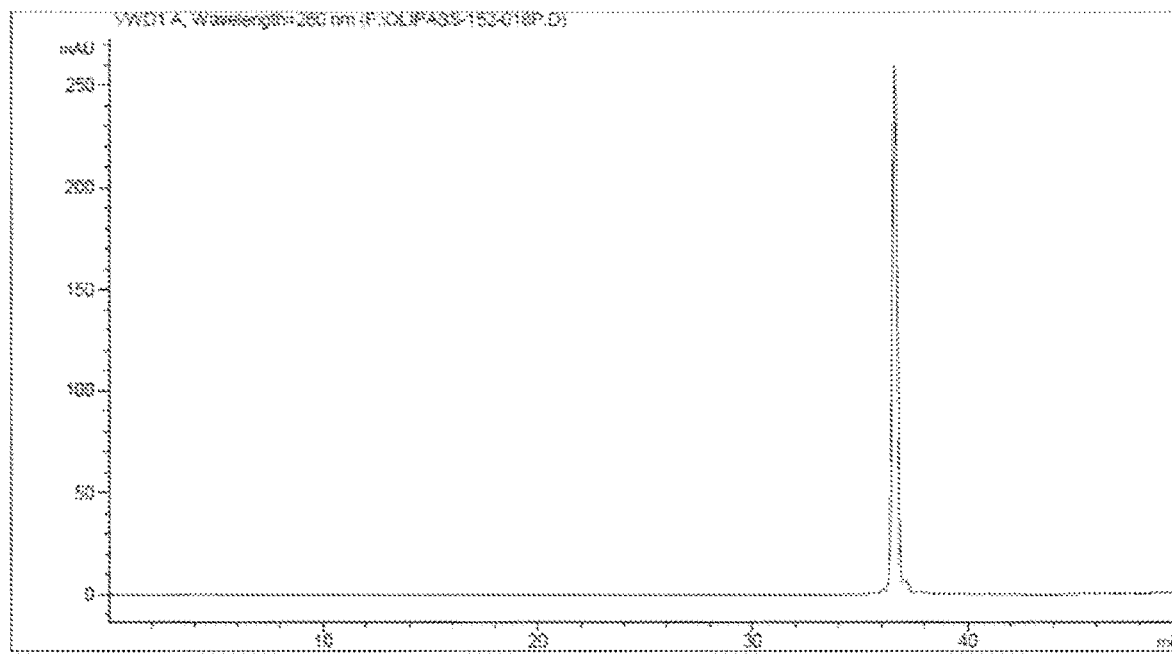
FIG. 13B. $C_{18}$-reverse phase HPLC chromatogram for "ASO 1" after HPLC purification.

[HPLC Analysis and Purification] Following a cleavage from resin, the crude product of a PNA derivative was purified by $C_{18}$-reverse phase HPLC eluting water/acetonitrile or water/methanol (gradient method) containing 0.1% TFA. FIGS. 13A and 13B are exemplary HPLC chromatograms for "ASO 1" before and after HPLC purification, respectively. The oligomer sequence of "ASO 1" is as provided in Table 1.

Synthetic Examples for PNA Derivative of Formula I

In order to complementarily target the 3' splice site of "exon 7" in the human SNAP25 pre-mRNA, PNA derivatives of this invention were prepared according to the synthetic procedures provided above or with minor modifications. Provision of such PNA derivatives targeting the human SNAP25 pre-mRNA is to exemplify the PNA derivatives of Formula I, and should not be interpreted to limit the scope of the present invention.

Table 1 provides PNA derivatives complementarily targeting the 3' splice site of "exon 7" in the human SNAP25 pre-mRNA along with structural characterization data by mass spectrometry. Provision of the SNAP25 ASOs in Table 1 is to exemplify the PNA derivatives of Formula I, and should not be interpreted to limit the scope of the present invention.

TABLE 1

PNA derivatives complementarily targeting the 3' splice site spanning the junction of "intron 6" and "exon 7" in the human SNAP25 pre-mRNA along with structural characterization data by mass spectrometry.

| PNA Example | PNA Sequence (N → C) | Exact Mass, m/z theor.[a] | obs.[b] |
|---|---|---|---|
| ASO 1 | Fethoc-A(6)TT-TG(6)T-TA(6)C-CC(1O2)T-GG(6)G-A(6)-NH$_2$ | 5190.39 | 5188.38 |
| ASO 2 | Fethoc-TG(5)T-TA(6)C-C(1O2)CT-GG(5)G-A(5)-NH$_2$ | 4266.93 | 4266.95 |
| ASO 3 | Fethoc-TG(5)T-TA(6)C-C(1O2)CT-GG(5)G-A(6)T-NH$_2$ | 4533.03 | 4533.04 |
| ASO 4 | Fethoc-TG(5)G-TA(5)C-C(1O2)CT-TG(5)G-A(5)T-NH$_2$ | 4519.01 | 4518.95 |
| ASO 5 | Fethoc-TG(6)T-TA(3)C-CC(1O5)T-GG(6)G-A(3)T-NH$_2$ | 4533.03 | 4533.04 |
| ASO 6 | Fethoc-G(5)TT-A(5)CC(1O2)-CTG-G(5)GA(5)-TC(1O2)-NH$_2$ | 4601.07 | 4601.08 |
| ASO 7 | Fethoc-C(1O2)AT-TTG(6)-TTA(5)-CCC(1O2)-TG(6)-NH$_2$ | 4478.98 | 4478.99 |
| ASO 8 | Fethoc-CA(6)T-TTG(5)-TTA(5)-CCC(1O2)-TG(5)-NH$_2$ | 4468.02 | 4468.04 |
| ASO 9 | Fethoc-A(6)TT-TG(5)T-TA(5)C-C(1O2)CT-G(5)-NH$_2$ | 4216.91 | 4216.93 |
| ASO 10 | Fethoc-CA(6)T-CA(6)T-TTG(5)-TTA(5)-CCC(1O2)-TG(5)-NH$_2$ | 5374.45 | 5374.44 |
| ASO 11 | Fethoc-A(6)TT-TG(5)T-TA(6)C-C(1O2)CT-GG(5)G-A(5)-NH$_2$ | 5188.36 | 5188.35 |
| ASO 12 | Fethoc-A(6)TT-TG(5)T-TA(6)C-C(1O2)CT-G(5)G-NH$_2$ | 4522.04 | 4522.05 |
| ASO 13 | Fethoc-A(5)TT-TG(5)T-TA(5)C-CC(1O2)T-GG(5)G-A(5)-NH$_2$ | 5160.33 | 5160.31 |
| ASO 14 | p-Toluenesulfonyl-TG(2O3)T-TA(5)C-CC(1O2)T-GG(5)G-A(5)T-Lys-NH$_2$ | 4581.03 | 4581.05 |
| ASO 15 | n-Hexanoyl-TG(5)T-TA(8)C-CC(1O2)T-GG(5)G-A(5)T-NH$_2$ | 4423.05 | 4423.03 |
| ASO 16 | Fethoc-Lys-Leu-TG(5)T-TA(5)C-CC(1O2)T-GG(5)G-A(2O2)T-Lys-NH$_2$ | 4890.27 | 4890.27 |
| ASO 17 | [N-(2-Phenylethyl)amino]carbonyl-TG(5)T-TA(4)C-CC(1O2)T-GG(5)G-A(5)T-NH$_2$ | 4415.98 | 4416.14 |
| ASO 18 | H-TG(5)T-TA(5)C-CC(1O2)T-GG(3)G-A(5)T-NH$_2$ | 4254.90 | 4254.64 |
| ASO 19 | n-Propyl-TG(2O2)T-TA(5)C-CC(2O2)T-GG(5)G-A(5)T-NH$_2$ | 4340.97 | 4341.03 |
| ASO 20 | Fethoc-TG(5)T-AA(5)C-CC(1O2)T-GG(5)T-A(5)T-NH$_2$ | 4503.02 | 4503.04 |

TABLE 1-continued

PNA derivatives complementarily targeting the 3' splice site spanning the junction of "intron 6" and "exon 7" in the human SNAP25 pre-mRNA along with structural characterization data by mass spectrometry.

| PNA Example | PNA Sequence (N → C) | Exact Mass, m/z theor.[a] | obs.[b] |
|---|---|---|---|
| ASO 21 | N-Me-N-Phenyl-TG(5)T-TA(5)C-CC(1O5)T-GG(5)G-A(5)T-NH$_2$ | 4415.03 | 4415.00 |
| ASO 22 | Benzoyl-TG(5)T-TA(5)C-CC(1O3)T-GG(5)G-A(5)T-NH$_2$ | 4400.97 | 4401.44 |

[a]theoretical exact mass,
[b]observed exact mass

Figure 14:
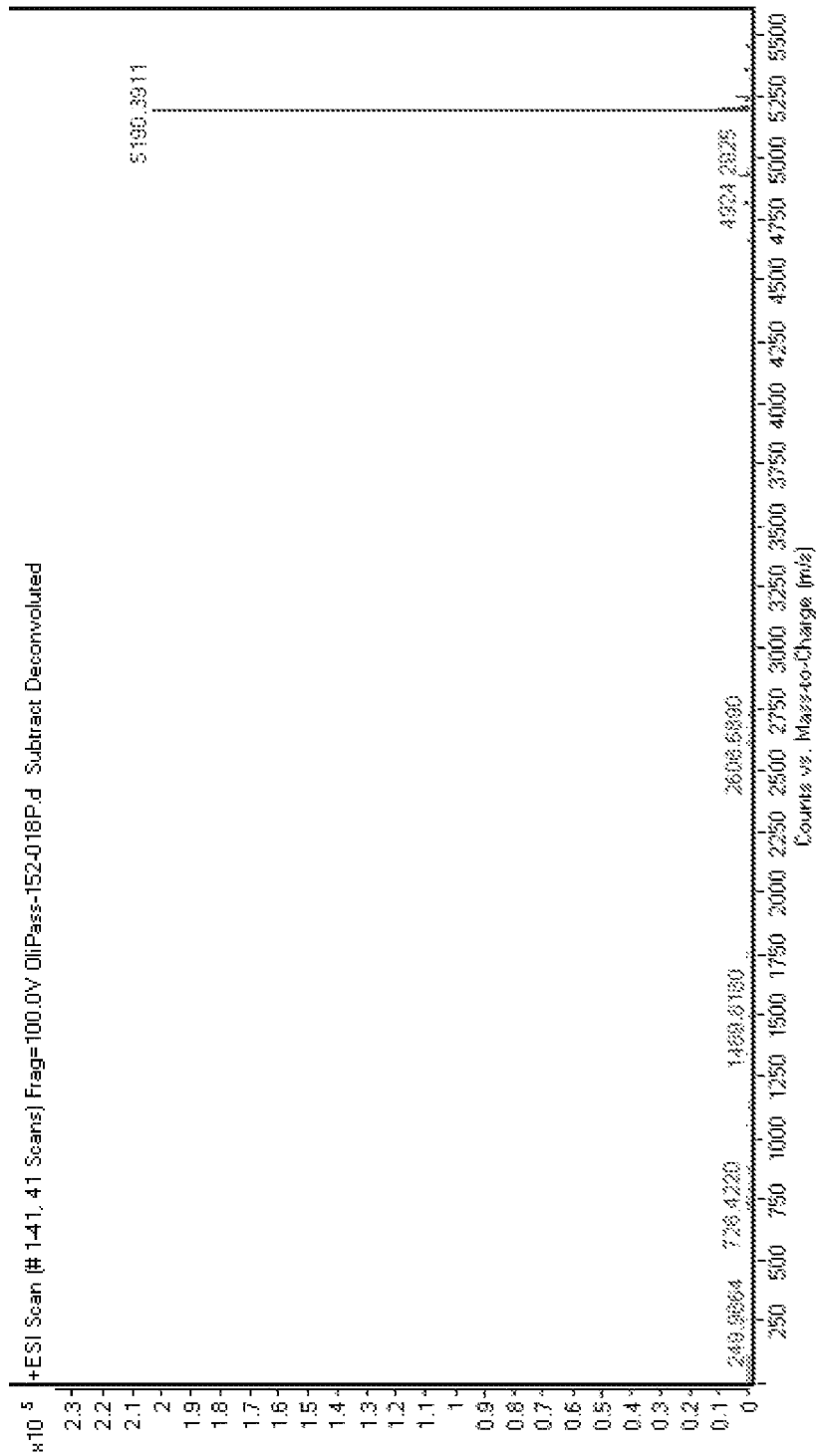
FIG. 14. ES-TOF mass spectral data obtained with "ASO 1" after HPLC purification.

FIG. 13A is a HPLC chromatogram obtained with a crude product of "ASO 1". The crude product was purified by $C_{18}$-RP preparatory HPLC. FIG. 13B is a HPLC chromatogram for a purified product of "ASO 1". The purity of "ASO 1" improved markedly following the preparatory HPLC purification. FIG. 14 provides an ESI-TOF mass spectrum obtained with the purified product of "ASO 1". Provision of the analysis data for "ASO 1" is to illustrate how the PNA derivatives of Formula I were purified and identified in the present invention, and should not be interpreted to limit the scope of this invention.

Binding Affinity of Model PNA Derivatives for Complementary DNA

The PNA derivatives in Table 1 were evaluated for their binding affinity for 10-mer DNAs complementarily targeting either the N-terminal or C-terminal. The binding affinity was assessed by $T_m$ value for the duplex between PNA and 10-mer complementary DNA. The duplex between PNA derivatives in Table 1 and fully complementary DNAs showed $T_m$ values too high to be reliably determined in aqueous buffer solution, since the buffer solution tended to boil during the $T_m$ measurement.

$T_m$ values were determined on an UV/Vis spectrometer as follows. A mixed solution of 4 µM PNA oligomer and 4 µM complementary 10-mer DNA in 4 mL aqueous buffer (pH 7.16, 10 mM sodium phosphate, 100 mM NaCl) in 15 mL polypropylene falcon tube was incubated at 90° C. for a minute and slowly cooled down to ambient temperature. Then the solution was transferred into a 3 mL quartz UV cuvette equipped with an air-tight cap, and subjected to a $T_m$ measurement at 260 nm on a UV/Visible spectrophotometer as described in the prior art [PCT/KR2009/001256] or with minor modifications. 10-mer complementary DNAs for $T_m$ measurement were purchased from Bioneer (www.bioneer.com, Dajeon, Republic of Korea) and used without further purification.

Observed $T_m$ values of the PNA derivatives of Formula I were very high for a complementary binding to 10-mer DNA, and are provided in Table 2 as uncorrected. For example, "ASO 3" showed a $T_m$ value of 77.3° C. for the duplex with the 10-mer complementary DNA targeting the N-terminal 10-mer in the PNA as marked "bold" and "underlined" in [(N→C) Fethoc-TG(5)T-TA(6)C-C(1O2)CT-GG(5)G-A(6)T-NH$_2$]. In the meantime, "ASO 3" showed a $T_m$ of 88.7° C. for the duplex with the 10-mer complementary DNA targeting the C-terminal 10-mer in the PNA as marked "bold" and "underlined" in [(N→C) Fethoc-TG(5)T-TA(6)C-C(1O2)CT-GG(5)G-A(6)T-NH$_2$].

TABLE 2

$T_m$ values between PNAs in Table and 10-mer complementary DNA targeting either the N-terminal or the C-terminal of PNA.

| | $T_m$ Value, °C. | |
|---|---|---|
| PNA | 10-mer DNA against N-Terminal | 10-mer DNA against C-Terminal |
| ASO 2 | 76.0 | 87.6 |
| ASO 3 | 77.3 | 88.7 |
| ASO 4 | 83.0 | 77.0 |
| ASO 5 | 73.0 | 85.8 |
| ASO 6 | 84.0 | 91.8 |
| ASO 8 | 58.0 | 68.0 |
| ASO 9 | 62.0 | 76.0 |
| ASO 10 | 61.0 | 68.0 |
| ASO 12 | 62.0 | 74.0 |

Examples for Biological Activities of PNA Derivatives of Formula I

PNA derivatives of Formula I specified in Table 1 were evaluated for the SNAP25 antisense activity in PC12 cells of rat origin and SiMa cells of human origin, and for their ability to inhibit the SNAP25 expression in the skin of C57BL/6 mice upon topical administration. The biological examples were provided as examples to illustrate the antisense activity of the PNA derivatives of Formula I, and therefore should not be interpreted to limit the scope of the current invention to the compounds listed in Table 1.

EXAMPLE 1

Exon Skipping Induced by "ASO 3"

"ASO 3" specified in is a 14-mer ASO fully complementary to a 14-mer sequence in the 3' splice site spanning the junction of "intron 6" and "exon 7" in the human SNAP25 pre-mRNA. "ASO 3" complementarily overlaps with the 14-mer pre-mRNA sequence as marked "bold" and "underlined" in the 30-mer pre-mRNA sequence of

[(5' → 3') cucuuuggaucccag | GGUAACAAAUGAUGC (SEQ ID NO: 2)].

"ASO 3" possesses a 7-mer overlap with "intron 6", and another 7-mer overlap with "exon 7".

In the meantime, the 14-mer ASO possesses a 13-mer complementary overlap with the rat SNAP25 pre-mRNA read out from the rat genomic DNA [accessed from NCBI Reference Sequence: NC_005012] as marked "bold" and "underlined" in the 25-mer pre-mRNA sequence of

[(5' → 3') ugg"c"ucccag | GGUAACAAACGAUGC (SEQ ID NO: 6)], in which the single mismatch marked with a quote (" ") sign.

"ASO 3" was evaluated for its ability to induce exon skipping in PC12 cells (Cat. Number CRL-1721, ATCC) as provided below.

[Cell Culture & ASO Treatment] PC12 cells were maintained in RPMI 1640 medium supplemented with 5% FBS, 10% horse serum, 1% streptomycin/penicillin, 1% L-glutamine, and 1% sodium pyruvate under 5% $CO_2$ atmosphere at 37° C. Cells grown in 60 mm culture dish containing 5 mL culture medium were treated with "ASO 3" at 0 (negative control), 10, 100 or 1,000 zM.

[RNA Extraction & cDNA Synthesis by One-step PCR] Following an incubation with "ASO 3" for 42 hours, the cells were treated with 100 µg/mL cycloheximide for another 6 hours in order to freeze the ribosomal translation. Then total RNA was extracted using "Universal RNA Extraction Kit" (Cat. Number 9767, Takara) according to the manufacturer's instructions. 200 ng of RNA template was subjected to a 25 µL reverse transcription reaction using Super Script® One-Step RT-PCR kit with Platinum® Taq polymerase (Cat. Number 10928-042, Invitrogen) against a set of exon-specific primers of [exon 1_forward: (5'→3') ATGGCCGAGGACGCAGACA (SEQ ID NO: 7); and exon 14_reverse: (5'→3') AGCATCTTTGTTGCACGTTG (SEQ ID NO: 8)] according to the following cycle conditions: 50° C. for 30 min and 94° C. for 2 min, which was followed by 40 cycles of 30 sec at 94° C., 30 sec at 50° C., and 1 min at 72° C.

[Nested PCR Amplification] 1 µL of cDNA was subjected to a 20 µL nested PCR reaction (Cat. Number K2612, Bioneer) against a set of exon specific primers of [exon 1_forward: (5'→3') ATGGCCGAGGACGCAGACA (SEQ ID NO: 7); exon 14n_reverse: (5'→3') TTGTTGGAGTCAGCGCCT (SEQ ID NO: 9)] according to the following cycle conditions: 95° C. for 2 min followed by 34 cycles of 30 sec at 95° C., 30 sec at 55° C., and 1 min at 72° C.

[Identification of Exon Skipping Products] The PCR products were subjected to electrophoretic separation on a 2% agarose gel. The bands of target size were collected and analyzed by Sanger Sequencing.

Figure 15A:
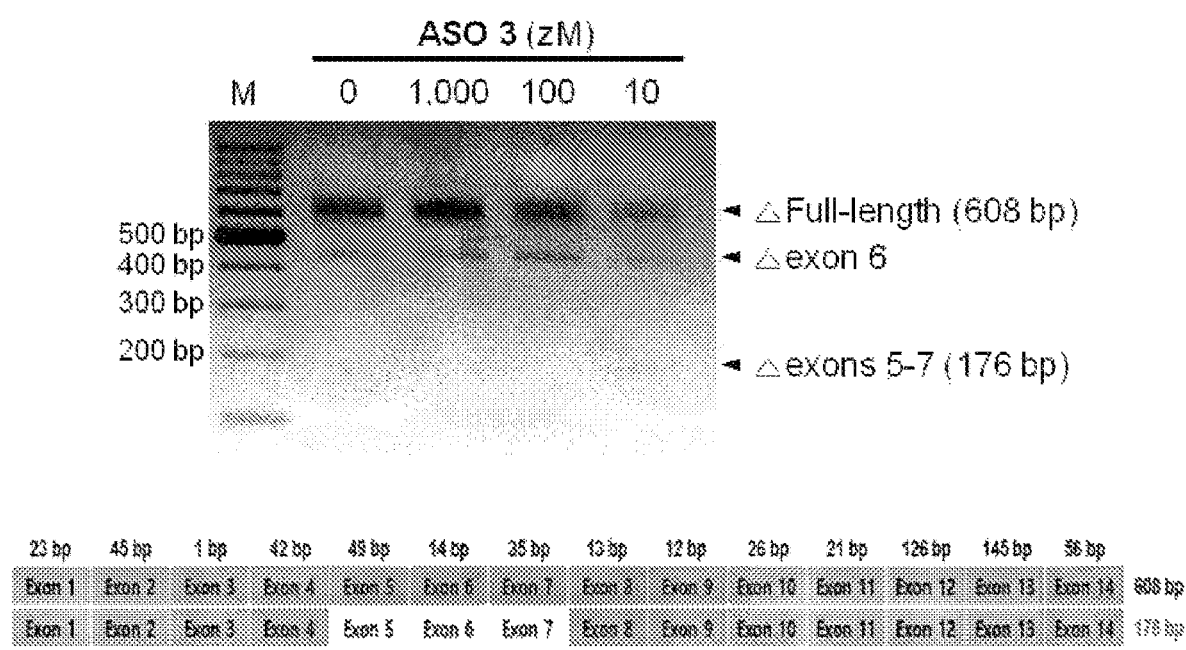
FIG. 15A. Electrophoretic analysis data for the nested PCR products in PC12 cells treated with 0 (negative control), 10, 100 or 1,000 zM "ASO 3" (top); along with a diagram illustrating the amplicon sizes of the PCR products for the full-length mRNA and the splice variant mRNAs with exon skipping (bottom).
Figure 15B:
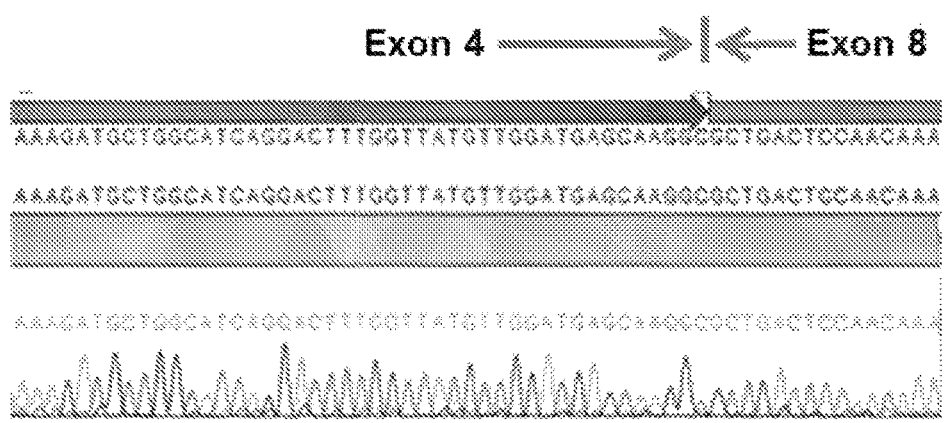
FIG. 15B. Sanger sequencing data for the PCR product assigned to the skipping of exons 5-7.

FIG. 15A provides the electrophoresis data of the PCR products, in which the 10 zM ASO treatment sample yielded a faint PCR band assignable to the skipping of exons 5-7. Even if the cells were treated with cycloheximide to destabilize the full-length mRNA by freezing the ribosomal translation, the exon skipping band was detected only faintly. Thus the SNAP25 mRNA splice variant assignable to the skipping of exons 5-7 is likely to show poor metabolic stability in cells compared to the full-length mRNA. The exon skipping PCR product was sequenced to be the skipping of exons 5-7 as shown in FIG. 15B. Since the PCR product assigned to the skipping of exon 6 was observed regardless of the ASO concentration, the skipping of exon 6 is considered to occur spontaneously.

The intensity of the full-length SNAP25 mRNA decreased most in the cells treated with 10 zM "ASO 3". The full-length mRNA intensity gradually increased to that of the negative control (i.e., without ASO treatment), as the ASO concentration was increased from 10 to 1,000 zM. The inverted dose response pattern in the nested PCR data could be due to a transcription upregulation by the "exon intron circular RNA (EIciRNA)" accumulated during the exon skipping with "ASO 3". [*Nature Struc. Mol. Biol.* vol 22(3), 256-264 (2015)]

EXAMPLE 2 qPCR for SNAP25 mRNA in PC12 Cells Treated with "ASO 3"

"ASO 3" was evaluated by SNAP25 nested qPCR for its ability to induce changes in the rat SNAP25 mRNA level in PC12 cells as follows.

[Cell Culture & ASO Treatment] PC12 cells grown in 60 mm culture dish containing 5 mL culture medium were treated with "ASO 3" at 0 (negative control), 10, 100 or 1,000 zM. (2 culture dishes per ASO concentration)

[RNA Extraction & cDNA Synthesis by One-step RT-PCR] Following an incubation with "SNAP-ASO 3" for 42 hours, the cells were treated 100 µg/mL cycloheximide for another 6 hours to freeze the ribosomal translation. Then total RNA was extracted from cells using "Universal RNA Extraction Kit" (Cat. Number 9767, Takara), and 200 ng of RNA template was subjected to a 25 µL reverse transcription reaction using One Step RT-PCR kit (Invitrogen, USA) against a set of exon-specific primers of [exon 1_forward: (5'→3') ATGGCCGAGGACGCAGACA (SEQ ID NO: 7); and exon 14_reverse: (5'→3') AGCATCTTTGTTGCACGTTG (SEQ ID NO: 8)] according to the following cycle conditions: 50° C. for 30 min and 94° C. for 2 min, which was followed by 20 cycles of 30 sec at 94° C., 30 sec at 55° C., and 1 min at 72° C.

[Nested qPCR Amplification] 1 µL of each cDNA solution diluted by 100× was subjected to a 20 µL Real-Time PCR reaction against a set of exon-specific primers of [exon 7q_forward: (5'→3') ATGGATGAAAACCTAGAGC (SEQ ID NO: 10); and exon 8q_reverse: (5'→3') CTTCCCAGCATCTTTGTT (SEQ ID NO: 11)] according to the following cycle conditions: 95° C. for 3 min followed by 40 cycles 10 sec at 95° C., and 30 sec at 60° C. The qPCR reaction was followed with a Taqman probe of [(5'→3') 5,6-FAM-CAGCCTTCT-ZEN-CCATGATCCT-3IABkFQ (SEQ ID NO: 12)] targeting the junction of exon 7 and exon 8 to quantify specifically the full-length SNAP25 mRNA.

Figure 16A:
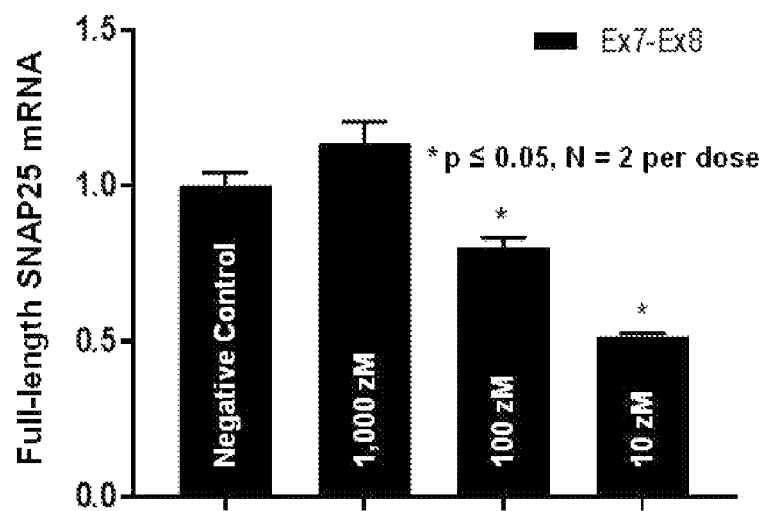
FIG. 16A. Changes in the full-length SNAP25 mRNA level in PC12 cells treated with "ASO 3" at 0 (negative control), 10, 100 or 1,000 zM. (error bar by standard error)

FIG. 16A provides the qPCR data, in which the full-length mRNA level significantly decreased (student's t-test) in the cells treated with "ASO 3" at 10 zM and 100 zM by ca 50% and 20%, respectively. However, the full-length mRNA level in the cells treated with 1,000 zM "ASO 3" was slightly higher than the level of the cells without ASO treatment (i.e., negative control). The inverted dose response pattern of the qPCR data is consistent fairly much with the dose response pattern of the full-length mRNA level observed during the exon skipping described in "Example 1", suggesting a transcription upregulation as the ASO dose was increased from 10 to 1,000 zM.

EXAMPLE 3 qPCR for SNAP25 mRNA in PC12 Cells Treated with "ASO 1"

"ASO 1" specified in Table 1 is a 16-mer ASO fully complementary to a 16-mer sequence of the 3' splice site spanning the junction of intron 6 and exon 7 in the human SNAP25 pre-mRNA. "ASO 1" complementarily overlaps with the 16-mer target sequence as marked "bold" and "underlined" in the 30-mer human pre-mRNA sequence of

[(5' → 3') cucuuuggaucccag | GGUAACAAAUGAUGC (SEQ ID NO: 2)].

"ASO 1" possesses a 6-mer overlap with intron 6 and a 10-mer overlap with exon 7. However, the ASO possesses a single mismatch with the rat SNAP25 pre-mRNA as marked "bold" and "underlined" in the 25-mer pre-MRNA sequence of

[(5' → 3') uggc<u>ucccag</u> | GGUAACAAA"C"GAUGC (SEQ ID NO: 6)], in which the single mismatch is marked with a quote (" ") sign.

"ASO 1" was evaluated by SNAP25 nested qPCR for its ability to induce changes in the rat SNAP25 mRNA level in PC12 cells as described in "Example 2", unless noted otherwise.

Figure 16B:
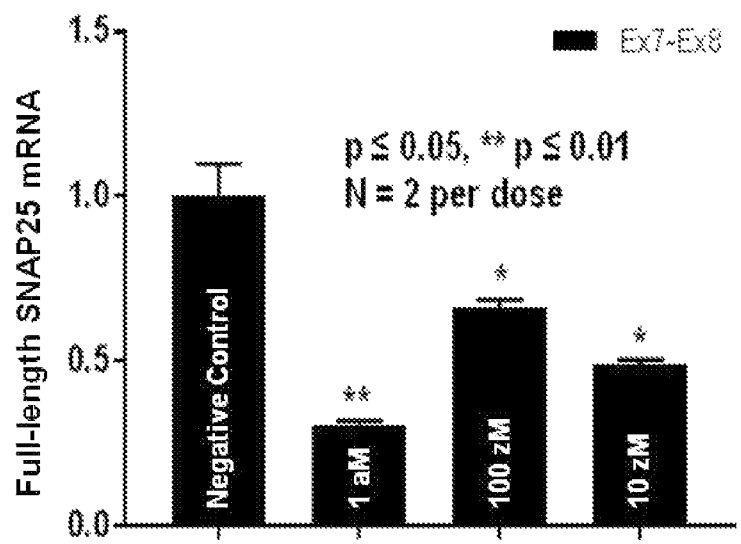
FIG. 16B. Changes in the full-length SNAP25 mRNA level in PC12 cells treated with "ASO 1" at 0 (negative control), 10, 100 or 1,000 zM. (error bar by standard error)

FIG. 16B provides the qPCR data, in which the full-length mRNA level significantly decreased (student's t-test) in the cells treated with "SNAP-ASO 1" at 10 zM, 100 zM and 1,000 zM by ca 50%, 40% and 70%, respectively. Like in the case of "ASO 3", the inverted dose response pattern was partly reproduced with "ASO 1" as the dose was increased from 10 to 100 zM. Given that the full-length mRNA level decreased further as the ASO concentration was increased to 1,000 zM, however, the exon skipping efficacy of "ASO 1" appears to be stronger than the efficacy of "ASO 3".

EXAMPLE 4

Inhibition of SNAP25 Protein Expression in PC12 Cells by "ASO 3"

"ASO 3" was evaluated for its ability to inhibit the expression of the SNAP25 protein in PC12 cells as follows.

PC12 cells were grown in 60 mm culture dish containing 5 mL culture medium, and treated with "ASO 3" at 0 zM (negative control), 1 zM, 10 zM, 30 zM, 100 zM, 300 zM, 1 aM, 3 aM or 10 aM for 48 hours. There were 4 culture dishes of the negative control to compensate for potential technical artifacts during the western blot analysis.

[Cell Lysis] Then the cells were subjected to lysis on ice with 200 μL 1× RIPA buffer (Cat. Number 9806, Cell Signaling Tech) supplemented with 1% SDS and 1× proteinase inhibitors cocktail (cOmplete Mini, Roche). The lysates were collected in 1.5 mL e-tube, mixed with 100 μL 5× sample buffer, and boiled for 5 min.

[Western Blot] The lysates were subjected to electrophoretic separation on a 4-15% TGX-PAGE gradient gel (Cat. Number 456-1086, Bio-Rad) and then transferred onto a 0.45 μm PVDF membrane. The membrane was probed with an anti-SNAP25 antibody (Cat. Number S9684, Sigma) and an anti-β-actin antibody (Cat. Number A3845, Sigma).

Figure 17A:
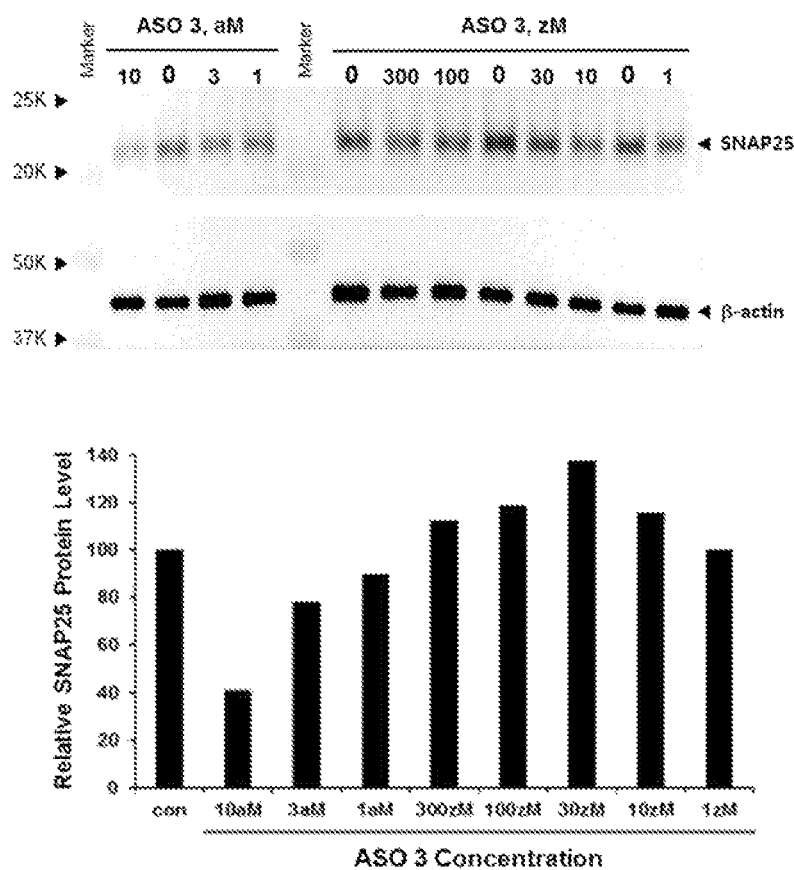
FIG. 17A. SNAP25 western blot data (top diagram) and relative SNAP25 expression levels normalized against β-actin (bottom diagram) in PC12 cells treated with "ASO 3" for 48 hours at 0 zM (negative control), 1 zM, 10 zM, 30 zM, 100 zM, 300 zM, 1 aM, 3 aM or 10 aM.

FIG. 17A provides the SNAP25 western blot data obtained with the PC12 cell lysates (top diagram) along with the relative SNAP25 expression levels normalized against (β-actin by densitometry (bottom diagram). The SNAP25 protein level decreased by 10 to 60% in the cells treated with "ASO 3". The expression level of the negative control (i.e., 0 zM "ASO 3") is the average expression level of the 4 samples.

EXAMPLE 5

Inhibition of SNAP25 Protein Expression in PC12 Cells by "ASO 1"

"ASO 1" was evaluated for its ability to inhibit the SNAP25 protein expression in PC12 cells as described in "Example 4", unless noted otherwise. PC12 cells were treated with "ASO 1" at 0 (negative control), 100 or 1,000 zM either for 48 hours or for 72 hours. (one culture dish for each ASO concentration)

Figure 17B:
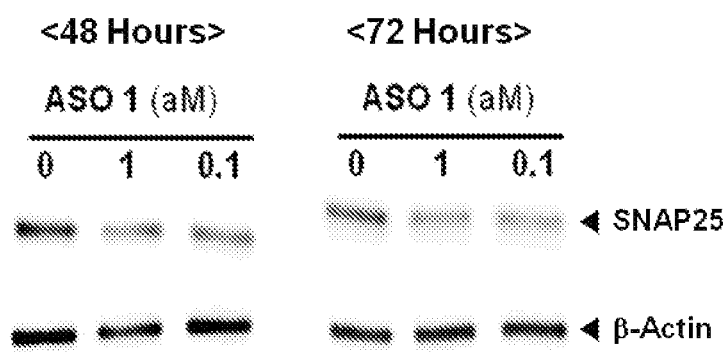
FIG. 17B. SNAP25 western blot data in PC12 cells treated with "ASO 1" at 0 (negative control), 100 or 1,000 zM either for 48 hours or for 72 hours.

FIG. 17B provides the western blot data for the ASO treatment of 48 hour (left) and 72 hours (right). "ASO 1" considerably inhibited the expression of the SNAP25 protein in PC12 cells at both time points.

EXAMPLE 6

Inhibition of SNAP25 Protein Expression in Skin Topically Administered with "ASO 1" in Mice "ASO 1" is fully complementary to the 3' splice site of "exon 7" in the mouse SNAP25 pre-mRNA. "ASO 1" was evaluated for its ability to inhibit the expression of the SNAP25 protein in the skin upon topical administration as described below.

[Hair Cut and Grouping] In Day 0, 8 female C57BL/6 mice (5 weeks old) were anesthetized with zoletil/rompun, and the hair in the back (ca 3 cm×4 cm) was cut with a clipper. Mice were randomly assigned into four groups, i.e., no ASO treatment group (negative control) and 3 treatment groups of 1 fM, 10 fM and 100 fM "ASO 1". (2 animals per group)

[Topical Administration] Topical solutions of "ASO 1" were prepared by diluting a mother aqueous stock solution in 30% (v/v) aqueous ethanol supplemented with 3% (v/v) glycerin to 0 (negative control), 1, 10 and 100 fM "ASO 1". Each animal was topically administered with ca 100 μL of a topical solution 2 times per day (morning & late in the afternoon) during Days 0 to 4 in the back skin of hair cut using a cotton ball.

[Skin Sampling] In the afternoon of Day 4, the animals were sacrificed after anesthetizing with zoletil/rompun in order to sample the portion of the skin topically treated with the ASO. The skin samples were then subjected to immunohistochemistry (IHC) analysis against the SNAP25 protein as described below.

[SNAP25 IHC] The skin samples were cryosectioned and immunostained in series with a primary anti-SNAP25 antibody (Cat. Number ab41455, Abcam) at 1:200 dilution, with a secondary anti-IgG (Cat Number BA-1100, Vector) at 1:200 dilution, and then with Dylight 594-streptavidin (Cat Number SA-5594, Vector, CA, USA) at 1:200 dilution for red fluorescence tagging. The anti-SNAP25 antibody probes the C-terminal of the SNAP25 protein. IHC images were captured on a Zeiss slide scanner to evaluate changes in the expression of the full-length SANP25 level. DAPI staining was additionally performed to localize the dermis microstructure.

Figure 18:
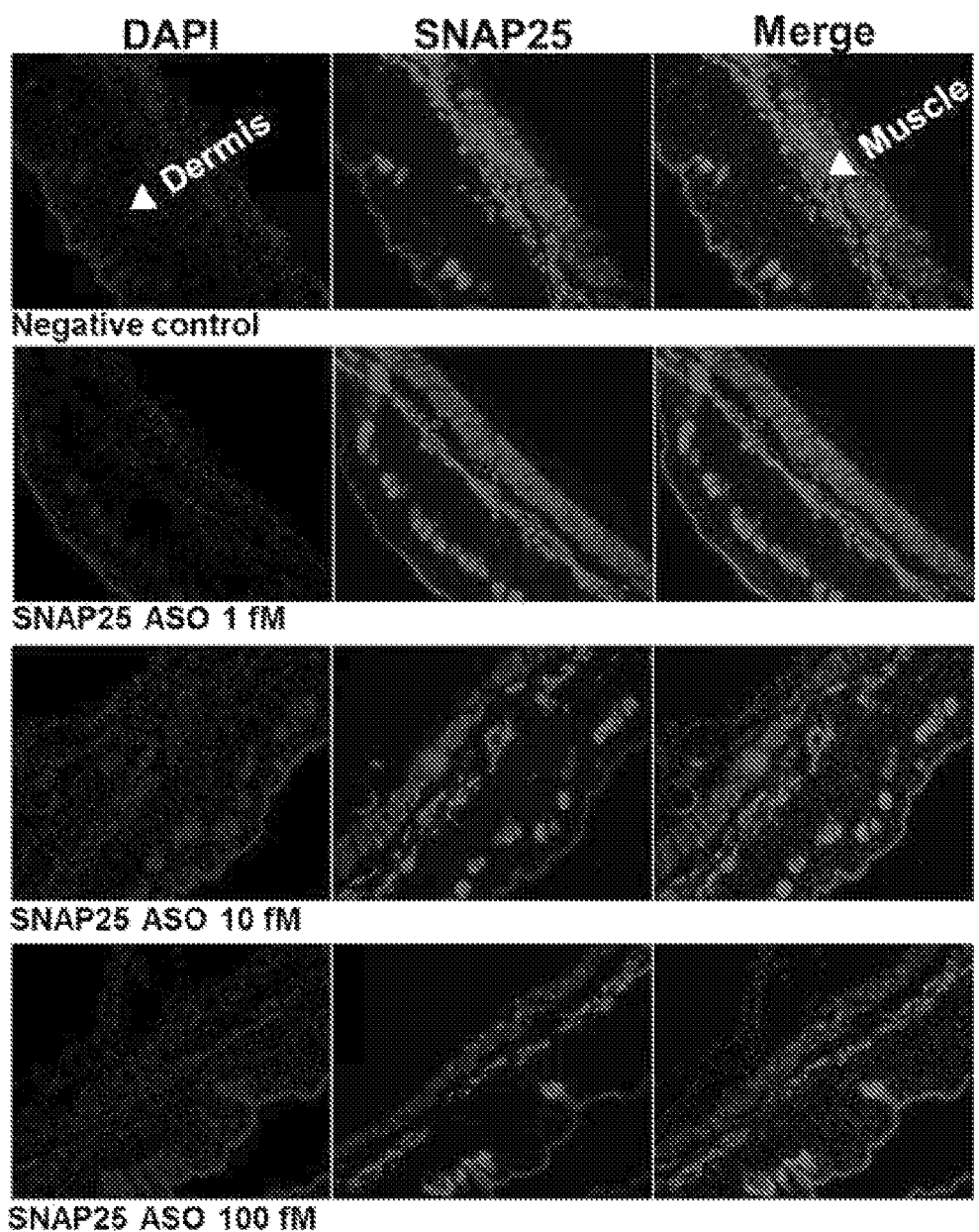
FIG. 18. SNAP25 IHC images for the skin samples of mice topically administered with "ASO 1" at 0 (negative control), 1, 10 and 100 fM, BID for four days.
Figure 19A:
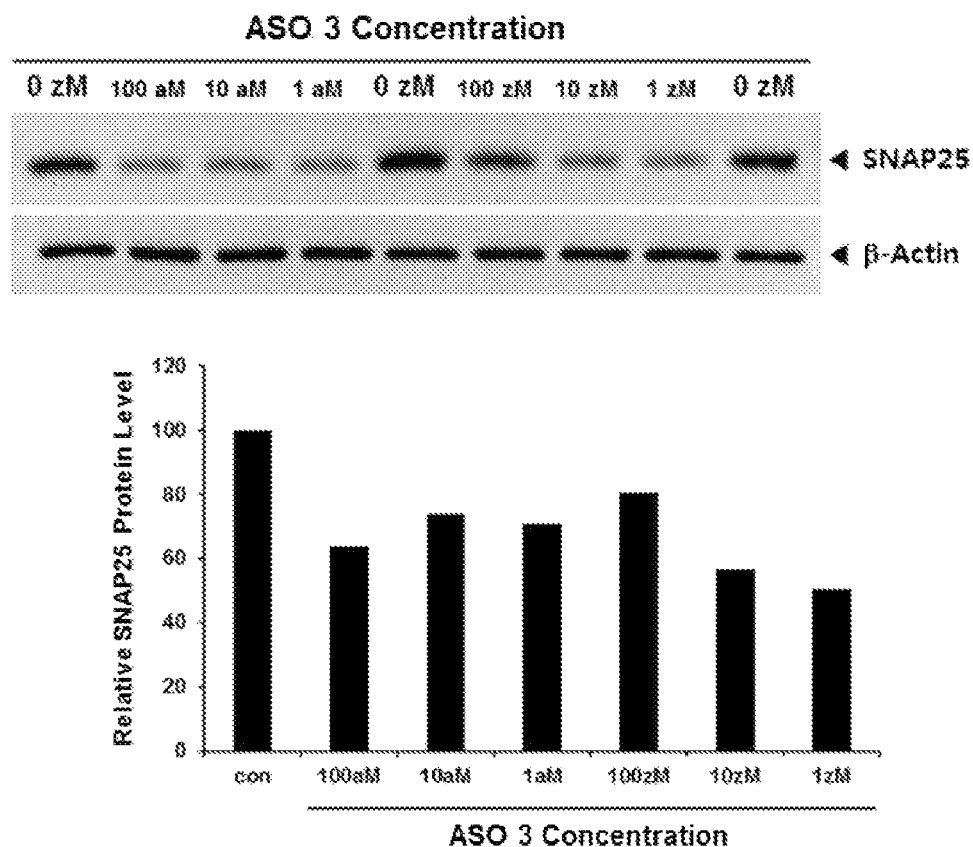
FIG. 19A. SNAP25 western blot data (top diagram) and relative SNAP25 expression levels normalized against β-actin (bottom diagram) in SiMa cells treated with "ASO 3" for 48 hours at 0 zM (negative control), 1 zM, 10 zM, 100 zM, 1 aM, 10 aM or 100 aM.
Figure 19B:
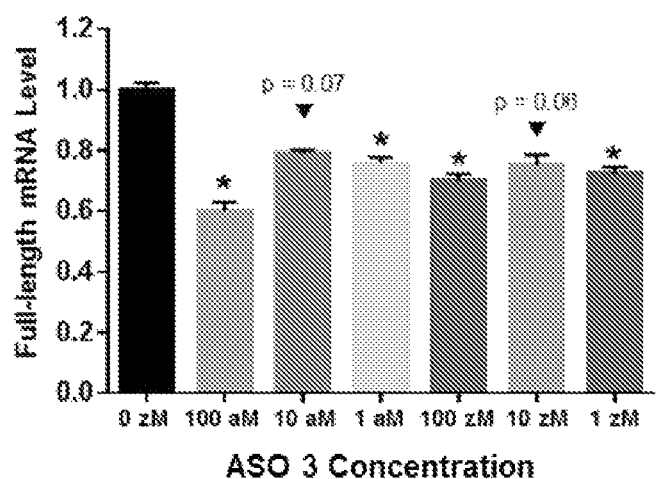
FIG. 19B. Changes in the full-length SNAP25 mRNA level in SiMa cells treated with "ASO 3" at 0 zM (negative control), 1 zM, 10 zM, 100 zM, 1 aM, 10 aM or 100 aM. (error bar by standard error).

FIG. 18 provides a representative set of the SNAP25 IHC images by group. In the negative control group, the full-length SNAP25 protein expression was high in the muscle layer underneath the dermis. The SNAP25 protein expression in the muscle layer is considered to originate from the SNAP25 protein expression in the motor-neuronal axons embedded in the muscle layer. The full-length SNAP25 protein expression in the muscle layer markedly decreased in the ASO treatment groups. The most notable decrease was observed in the 100 fM "ASO 1" treatment group. The inhibitory extent of the full-length SNAP25 protein expression in the skin was much stronger than the extent observed in PC12 cells (cf. "Example 5").

Given that BTX has been widely used to treat facial wrinkles (for anti-aging) by injection, the inhibition of the SNAP25 protein expression in the muscle layer underneath the dermis is of pharmacological and therapeutic importance. A BTX injection is associated with a risk that a certain fraction of the injection potentially distributes to muscle tissues of safety concern. If BTX distributes to pulmonary smooth muscle tissues, for example, the subject is at a high risk of pulmonary insufficiency.

The SNAP25 inhibitory activity depends on the ASO concentration in target tissue. Upon topical administration, the ASO concentration rapidly decreases in tissues distal to the dermal layer of ASO administration. It is unlikely that target tissues of safety concern are exposed to the ASO at a concentration sufficiently high enough to raise safety concern. Thus the PNA derivative of Formula I for topical use is distinctively advantageous over BTX injection for safety as well as subject compliance.

EXAMPLE 7

Inhibition of SNAP25 Protein Expression in SiMa Cells by "ASO 3"

"ASO 3" was evaluated for its ability to inhibit the expression of the SNAP25 protein in SiMa human neuroblastoma cells as follows.

[Cell Culture and ASO Treatment] SiMa cells (Cat. Number ACC164, DSMZ) were maintained in RPMI 1640 medium supplemented with 10% FBS, 1% streptomycin/penicillin, 1% L-glutamine, and 1% sodium pyruvate under 5% $CO_2$ atmosphere at 37° C. SiMa cells were grown in 60 mm culture dish containing 5 mL culture medium, and were treated for 48 hours with "ASO 3" at 0 zM (negative control), 1 zM to 100 aM. There were 3 culture dishes for the negative control to compensate for potential technical artifacts during the western blot analysis.

[Lysis] The cells were subjected to lysis on ice with 200 μL 1× RIPA buffer (Cat. Number 9806, Cell Signaling Tech) supplemented with 0.1% SDS and 1× proteinase inhibitors cocktail (cOmplete Mini, Roche). Then the lysates were collected in 1.5 mL e-tube, mixed with 100 μL 5× sample buffer, and boiled for 5 min.

[Western Blot] The lysates were subjected to electrophoretic separation on a 12% SDS-PAGE gel, and transferred onto a 0.2 μm polyvinylidene difluoride (PVDF) membrane. The membrane was probed with an anti-SNAP25 antibody (Cat. Number ab41455, Sigma) and an anti-β-actin antibody (Cat. Number A3845, Sigma).

FIG. 19A provides the SNAP25 western blot data obtained with the cell lysates (top diagram) along with the relative SNAP25 expression levels normalized against (β-actin by densitometry (bottom diagram). The expression level of the negative control (i.e., 0 zM "ASO 3") is the average expression level of the 3 samples. The SNAP25 protein level decreased by 40 to 50% in the cells treated with "ASO 3".

SNAP25 EXAMPLE 8 qPCR for SNAP25 mRNA in SiMa Cells Treated with "ASO 3"

"ASO 3" was evaluated by SNAP25 nested qPCR for its ability to induce changes in the human SNAP25 mRNA level in SiMa cells as follows.

[Cell Culture & ASO Treatment] SiMa cells were grown in 60 mm culture dish containing 5 mL culture medium, and were treated with "ASO 3" at 0 zM (negative control), 1 zM, 10 zM, 100 zM or 1 aM, 10 aM, or 100 aM. (2 culture dishes per ASO concentration)

[RNA Extraction & cDNA Synthesis] Total RNA was extracted from cells using "RNeasy Mini Kit" (Cat. Number 74106, Qiagen) according to the manufacturer's instructions. 200 ng of RNA template was subjected to a 25 μl reverse transcription reaction using PrimeScript 1$^{st}$ strand cDNA synthesis Kit (Cat. No. 6110B, Takara) against random hexamers.

[qPCR Amplification] The PCR reactions were monitored with a Taqman probe [(5'→3') 56-FAM-CGGCTTCAT-ZEN-CCGCAGGGTAACAA-3IABkFQ (SEQ ID NO: 13)] targeting the junction of exon 6 and exon 7 against a set of exon-specific primers [exon 6_forward: (5'→3') GACGAAC-GGGAGCAGATG (SEQ ID NO: 14); and exon 8_reverse(2): (5'→3') ATCTCATTGCC-CATATCCAGG (SEQ ID NO: 15)]. Cycle Conditions: 95° C. for 3 min followed by 40 cycles 15 sec at 95° C., and 30 sec at 60° C.

FIG. 19B provides the qPCR data, in which the full-length human SNAP25 mRNA level significantly decreased (student's t-test) in the cells treated with "ASO 3" at 1 zM, 100 zM, 1 aM and 100 aM by 20 to 40%. The cells treated with the ASO at 100 aM showed the strongest inhibition of 40%.

The invention claimed is:

1. A peptide nucleic acid derivative represented by Formula I, or a pharmaceutically acceptable salt thereof:

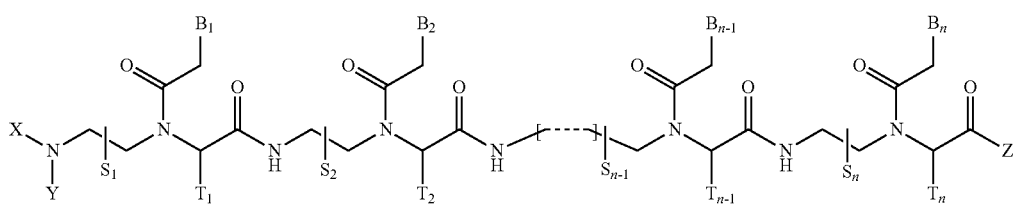

Formula I wherein, n is an integer between 10 and 25;

the compound of Formula I possesses at least a 10-mer complementary overlap with a 14-mer pre-mRNA sequence of [(5'→3') AUCCCAGGGUAACA (SEQ ID NO: 1)] in the human SNAP25 pre-mRNA;

the compound of Formula I is fully complementary to the human SNAP25 pre-mRNA, or partially complementary to the human SNAP25 pre-mRNA with one or two mismatches;

$S_1, S_2, \ldots, S_{n-1}, S_n, T_1, T_2, \ldots, T_{n-1}$, and $T_n$ independently represent deuterido [D], hydrido [H], substituted or non-substituted alkyl, or substituted or non-substituted aryl radical;

X and Y independently represent hydrido, formyl [H—C(=O)—], aminocarbonyl [NH$_2$—C(=O)—], aminothiocarbonyl [NH$_2$—C(=S)—], substituted or non-substituted alkyl, substituted or non-substituted aryl, substituted or non-substituted alkylacyl, substituted or non-substituted arylacyl, substituted or non-substituted alkyloxycarbonyl, substituted or non-substituted aryloxycarbonyl, substituted or non-substituted alkylaminocarbonyl, substituted or non-substituted arylaminocarbonyl, substituted or non-substituted alkylaminothiocarbonyl, substituted or non-substituted arylaminothiocarbonyl, substituted or non-substituted alkyloxythiocarbonyl, substituted or non-substituted aryloxythiocarbonyl, substituted or non-substituted alkylsulfonyl, substituted or non-substituted arylsulfonyl, substituted or non-substituted alkylphosphonyl radical, or substituted or non-substituted arylphosphonyl radical;

Z represents hydrido, hydroxy, substituted or non-substituted alkyloxy, substituted or non-substituted aryloxy, substituted or non-substituted amino, substituted or non-substituted alkyl, or substituted or non-substituted aryl radical;

$B_1, B_2, \ldots, B_{n-1}$, and $B_n$, are independently selected from natural nucleobases including adenine, thymine, guanine, cytosine and uracil, and unnatural nucleobases; and, at least four of $B_1, B_2, \ldots, B_{n-1}$, and $B_n$, are independently selected from unnatural nucleobases with a substituted or non-substituted amino radical covalently linked to the nucleobase moiety.

2. The peptide nucleic acid derivative according to claim 1, or a pharmaceutical salt thereof:

wherein, n is an integer between 10 and 25;

the compound of Formula I possesses at least a 10-mer complementary overlap with a 14-mer pre-mRNA sequence of [(5'→3') AUCCCAGGGUAACA (SEQ ID NO: 1)] in the human SNAP25 pre-mRNA;

the compound of Formula I is fully complementary to the human SNAP25 pre-mRNA, or partially complementary to the human SNAP25 pre-mRNA with one or two mismatches;

$S_1, S_2, \ldots, S_{n-1}, S_n, T_1, T_2, \ldots, T_{n-1}$, and $T_n$ independently represent deuterido, hydrido, substituted or non-substituted alkyl, or substituted or non-substituted aryl radical;

X and Y independently represent hydrido, formyl, aminocarbonyl, aminothiocarbonyl, substituted or non-substituted alkyl, substituted or non-substituted aryl, substituted or non-substituted alkylacyl, substituted or non-substituted arylacyl, substituted or non-substituted alkyloxycarbonyl, substituted or non-substituted aryloxycarbonyl, substituted or non-substituted alkylaminocarbonyl, substituted or non-substituted arylaminocarbonyl, substituted or non-substituted alkylaminothiocarbonyl, substituted or non-substituted arylaminothiocarbonyl, substituted or non-substituted alkyloxythiocarbonyl, substituted or non-substituted aryloxythiocarbonyl, substituted or non-substituted alkylsulfonyl, substituted or non-substituted arylsulfonyl, substituted or non-substituted alkylphosphonyl radical, or substituted or non-substituted arylphosphonyl radical;

Z represents hydrido, hydroxy, substituted or non-substituted alkyloxy, substituted or non-substituted aryloxy, substituted or non-substituted amino, substituted or non-substituted alkyl, or substituted or non-substituted aryl radical;

$B_1, B_2, \ldots, B_{n-1}$, and $B_n$, are independently selected from natural nucleobases including adenine, thymine, guanine, cytosine and uracil, and unnatural nucleobases; and, at least four of $B_1, B_2, \ldots, B_{n-1}$, and $B_n$, are independently selected from unnatural nucleobases represented by Formula II, Formula III, or Formula IV:

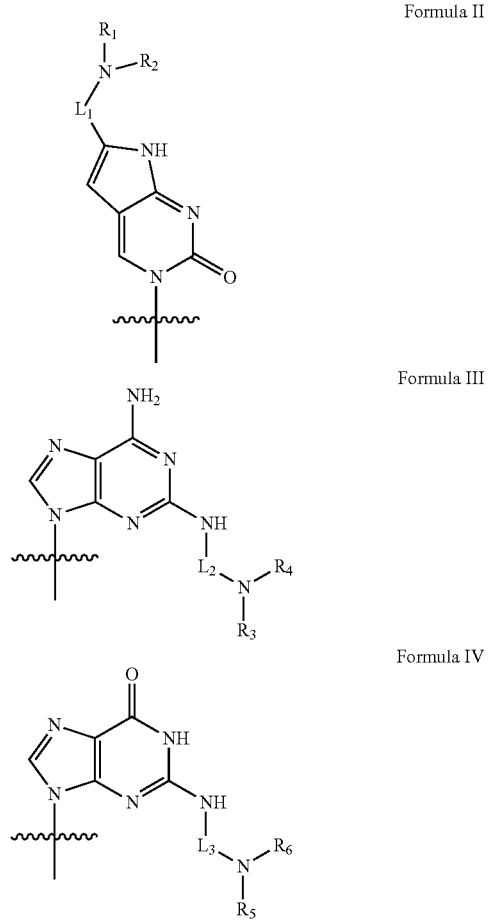

Formula II

Formula III

Formula IV wherein, $R_1, R_2, R_3, R_4, R_5$ and $R_6$ are independently selected from hydrido, and substituted or non-substituted alkyl radical;

$L_1, L_2$ and $L_3$ are a covalent linker represented by Formula V covalently linking the basic amino group to the nucleobase moiety:

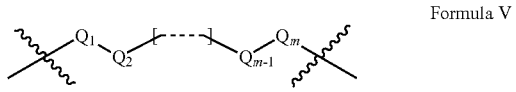

Formula V wherein, $Q_1$ and $Q_m$ are substituted or non-substituted methylene (—$CH_2$—) radical, and $Q_m$ is directly linked to the basic amino group;

$Q_2, Q_3, \ldots$, and $Q_{m-1}$ are independently selected from substituted or non-substituted methylene, oxygen (—O—), sulfur (—S—), and substituted or non-substituted amino radical [—N(H)—, or —N(substituent)-]; and, m is an integer between 1 and 15.

3. The peptide nucleic acid derivative according to claim 1, or a pharmaceutical salt thereof:
wherein,
n is an integer between 11 and 21;
the compound of Formula I possesses at least a 10-mer complementary overlap with a 14-mer pre-mRNA sequence of [(5'→3') AUCCCAGGGUAACA (SEQ ID NO: 1)] in the human SNAP25 pre-mRNA;
the compound of Formula I is fully complementary to the human SNAP25 pre-mRNA, or partially complementary to the human SNAP25 pre-mRNA with one or two mismatches;
$S_1, S_2, \ldots, S_{n-1}, S_n, T_1, T_2, \ldots, T_{n-1}$, and $T_n$ are hydrido radical;
X and Y independently represent hydrido, substituted or non-substituted alkyl, substituted or non-substituted aryl, substituted or non-substituted alkylacyl, substituted or non-substituted arylacyl, substituted or non-substituted alkyloxycarbonyl, substituted or non-substituted aryloxycarbonyl, substituted or non-substituted alkylaminocarbonyl, substituted or non-substituted arylaminocarbonyl, substituted or non-substituted alkylsulfonyl, or substituted or non-substituted arylsulfonyl radical;
Z represents substituted or non-substituted amino radical;
$B_1, B_2, \ldots, B_{n-1}$, and $B_n$, are independently selected from natural nucleobases including adenine, thymine, guanine, cytosine and uracil, and unnatural nucleobases;
at least four of $B_1, B_2, \ldots, B_{n-1}$, and $B_n$, are independently selected from unnatural nucleobases represented by Formula II, Formula III, or Formula IV;
$R_1, R_2, R_3, R_4, R_5$ and $R_6$ are independently selected from hydrido, and substituted or non-substituted alkyl radical;
$Q_1$ and $Q_m$ are substituted or non-substituted methylene radical, and $Q_m$ is directly linked to the basic amino group;
$Q_2, Q_3, \ldots$, and $Q_{m-1}$ are independently selected from substituted or non-substituted methylene, oxygen, and amino radical; and,
m is an integer between 1 and 11.

4. The peptide nucleic acid derivative according to claim 1, or a pharmaceutical salt thereof:
wherein,
n is an integer between 11 and 19;
the compound of Formula I possesses at least a 10-mer complementary overlap with a 14-mer pre-mRNA sequence of [(5'→3') AUCCCAGGGUAACA (SEQ ID NO: 1)] in the human SNAP25 pre-mRNA;
the compound of Formula I is fully complementary to the human SNAP25 pre-mRNA;
$S_1, S_2, \ldots, S_{n-1}, S_n, T_1, T_2, \ldots, T_{n-1}$, and $T_n$ are hydrido radical;
X and Y independently represent hydrido, substituted or non-substituted alkyl, substituted or non-substituted aryl, substituted or non-substituted alkylacyl, substituted or non-substituted arylacyl, substituted or non-substituted alkyloxycarbonyl, substituted or non-substituted alkylaminocarbonyl, substituted or non-substituted alkylsulfonyl, or substituted or non-substituted arylsulfonyl radical;
Z represents substituted or non-substituted amino radical;
$B_1, B_2, \ldots, B_{n-1}$, and $B_n$, are independently selected from natural nucleobases including adenine, thymine, guanine, cytosine and uracil, and unnatural nucleobases;
at least four of $B_1, B_2, \ldots, B_{n-1}$, and $B_n$, are independently selected from unnatural nucleobases represented by Formula II, Formula III, or Formula IV;
$R_1, R_2, R_3, R_4, R_5$ and $R_6$ are independently selected from hydrido, and substituted or non-substituted alkyl radical;
$Q_1$ and $Q_m$ are methylene radical, and $Q_m$ is directly linked to the basic amino group;
$Q_2, Q_3, \ldots$, and $Q_{m-1}$ are independently selected from methylene, oxygen, and amino radical; and,
m is an integer between 1 and 9.

5. The peptide nucleic acid derivative according to claim 1, or a pharmaceutical salt thereof:
wherein,
n is an integer between 11 and 19;
the compound of Formula I possesses at least a 10-mer complementary overlap with a 14-mer pre-mRNA sequence of [(5'→3') AUCCCAGGGUAACA (SEQ ID NO: 1)] in the human SNAP25 pre-mRNA;
the compound of Formula I is fully complementary to the human SNAP25 pre-mRNA;
$S_1, S_2, \ldots, S_n, T_1, T_2, \ldots, T_{n-1}$, and $T_n$ are hydrido radical;
X and Y independently represent hydrido, substituted or non-substituted alkyl, substituted or non-substituted aryl, substituted or non-substituted alkylacyl, substituted or non-substituted arylacyl, or substituted or non-substituted alkyloxycarbonyl radical;
Z represents substituted or non-substituted amino radical;
$B_1, B_2, \ldots, B_{n-1}$, and $B_n$, are independently selected from natural nucleobases including adenine, thymine, guanine, cytosine and uracil, and unnatural nucleobases;
at least four of $B_1, B_2, \ldots, B_{n-1}$, and $B_n$, are independently selected from unnatural nucleobases represented by Formula II, Formula III, or Formula IV;
$R_1, R_3$, and $R_5$ are hydrido radical, and $R_2, R_4$, and $R_6$ independently represent hydrido, or substituted or non-substituted alkyl radical;
$Q_1$ and $Q_m$ are methylene radical, and $Q_m$ is directly linked to the basic amino group;
$Q_2, Q_3, \ldots$, and $Q_{m-1}$ are independently selected from methylene, oxygen radical; and,
m is an integer between 1 and 8.

6. The peptide nucleic acid derivative according to claim 1, or a pharmaceutical salt thereof:
wherein,
n is an integer between 11 and 19;
the compound of Formula I possesses at least a 10-mer complementary overlap with a 14-mer pre-mRNA sequence of [(5'→3') AUCCCAGGGUAACA (SEQ ID NO: 1)] in the human SNAP25 pre-mRNA;
the compound of Formula I is fully complementary to the human SNAP25 pre-mRNA;
$S_1, S_2, \ldots, S_n, T_1, T_2, \ldots, T_{n-1}$, and $T_n$ are hydrido radical;
X and Y independently represent hydrido, substituted or non-substituted alkylacyl, substituted or non-substituted arylacyl, or substituted or non-substituted alkyloxycarbonyl radical;
Z represents substituted or non-substituted amino radical;
$B_1, B_2, \ldots, B_{n-1}$, and $B_n$, are independently selected from adenine, thymine, guanine, cytosine, and unnatural nucleobases;
at least five of $B_1, B_2, \ldots, B_{n-1}$, and $B_n$ are independently selected from unnatural nucleobases represented by Formula II, Formula III, or Formula IV;
$R_1, R_2, R_3, R_4, R_5$, and $R_6$ are hydrido radical;
$Q_1$ and $Q_m$ are methylene radical, and $Q_m$ is directly linked to the basic amino group;
$Q_2, Q_3, \ldots$, and $Q_{m-1}$ are independently selected from methylene, and oxygen radical; and,
m is an integer between 1 and 8.

7. The peptide nucleic acid derivative according to claim 1, or a pharmaceutical salt thereof:
wherein,
n is an integer between 11 and 19;
the compound of Formula I possesses at least a 10-mer complementary overlap with a 14-mer pre-mRNA sequence of [(5'→3') AUCCCAGGGUAACA (SEQ ID NO: 1)] in the human SNAP25 pre-mRNA;
the compound of Formula I is fully complementary to the human SNAP25 pre-mRNA;
$S_1, S_2, \ldots, S_{n-1}, S_n, T_1, T_2, \ldots, T_{n-1}$, and $T_n$ are hydrido radical;
X is hydrido radical;
Y represents substituted or non-substituted alkylacyl, substituted or non-substituted arylacyl, or substituted or non-substituted alkyloxycarbonyl radical;
Z represents substituted or non-substituted amino radical;
$B_1, B_2, \ldots, B_{n-1}$, and $B_n$, are independently selected from adenine, thymine, guanine, cytosine, and unnatural nucleobases;
at least five of $B_1, B_2, \ldots, B_{n-1}$, and $B_n$, are independently selected from unnatural nucleobases represented by Formula II, Formula III, or Formula IV;
$R_1, R_2, R_3, R_4, R_5$, and $R_6$ are hydrido radical;
$L_1$ represents —(CH$_2$)$_2$—O—(CH$_2$)$_2$—, —CH$_2$—O—(CH$_2$)$_2$—, —CH$_2$—O—(CH$_2$)$_3$—, —CH$_2$—O—(CH$_2$)$_4$—, or —CH$_2$—O—(CH$_2$)$_5$— with the right end is directly linked to the basic amino group; and,
$L_2$ and $L_3$ are independently selected from —(CH$_2$)$_2$—, —(CH$_2$)$_3$—, —(CH$_2$)$_4$—, —(CH$_2$)$_5$—, —(CH$_2$)$_6$—, —(CH$_2$)$_7$—, —(CH$_2$)$_8$—, —(CH$_2$)$_2$—O—(CH$_2$)$_2$—, —(CH$_2$)$_3$—O—(CH$_2$)$_2$—, and —(CH$_2$)$_2$—O—(CH$_2$)$_3$— with the right end is directly linked to the basic amino group.

8. The peptide nucleic acid derivative according to claim 1, which is selected from the group of peptide nucleic acid derivatives provided below, or a pharmaceutically acceptable salt thereof:
(N→C) Fethoc-A(6)TT-TG(6)T-TA(6)C-CC(1O2)T-GG(6)G-A(6)-NH$_2$;
(N→C) Fethoc-A(6)TC-TG(6)T-TA(6)C-CC(1O2)T-GG(6)G-A(6)-NH$_2$;
(N→C) Piv-A(6)TT-TG(6)T-TA(6)C-CC(1O2)T-GG(6)G-A(6)-NH$_2$;

(N→C) Fethoc-A(6)TT-TG(6)T-TA(2O2)C-CC(1O2)T-GG(5)G-A(5)-NH₂;
(N→C) Fmoc-Lys-A(6)TT-TG(6)T-TA(6)C-CC(1O2)T-GG(6)G-A(6)-NH₂;
(N→C) Fethoc-TG(5)T-TA(6)C-C(1O2)CT-GG(5)G-A(5)-NH₂;
(N→C) Fethoc-TG(5)T-TA(6)C-C(1O2)CT-GG(5)T-A(5)-NH₂;
(N→C) Fethoc-TG(5)T-TA(6)C-C(1O3)CT-GG(5)G-A(5)-NH₂;
(N→C) Fethoc-Lys-Leu-TG(5)T-TA(5)C-CC(1O2)T-GG(5)G-A(2O2)T-Lys-NH₂;
(N→C) H-TG(5)T-TA(5)C-CC(1O2)T-GG(3)G-A(5)T-NH₂;
(N→C) Benzoyl-TG(5)T-TA(6)C-C(1O3)CT-GG(5)G-A(5)-Val-Lys-NH₂;
(N→C) Benzoyl-TG(5)T-TA(5)C-CC(1O3)T-GG(5)G-A(5)T-NH₂;
(N→C) n-Hexanoyl-TG(5)T-TA(8)C-CC(1O2)T-GG(5)G-A(5)T-NH₂;
(N→C) n-Propyl-TG(5)T-TA(6)C-C(1O3)CT-GG(5)G-A(5)-NH₂;
(N→C) Ac-TG(5)T-TA(6)C-C(1O3)CT-GG(5)G-A(5)-NH₂;
(N→C) [N-(2-Phenylethyl)amino]carbonyl-TG(5)T-TA(4)C-CC(1O2)T-GG(5)G-A(5)T-NH₂;
(N→C) n-Propyl-TG(2O2)T-TA(5)C-CC(2O2)T-GG(5)G-A(5)T-NH₂;
(N→C) FAM-HEX-HEX-TG(2O2)T-TA(5)C-CC(2O2)T-GG(5)G-A(5)T-NH₂;
(N→C) n-Propyl-TG(2O2)T-TA(5)C-CC(2O2)T-GG(5)G-A(5)T-Arg-NH₂;
(N→C) n-Benzoyl-Gly-TG(2O2)T-TA(5)C-CC(2O2)T-GG(5)G-A(5)T-NH₂;
(N→C)N-Me-N-Phenyl-TG(5)T-TA(5)C-CC(1O5)T-GG(5)G-A(5)T-NH₂;
(N→C) p-Toluenesulfonyl-TG(2O3)T-TA(5)C-CC(1O2)T-GG(5)G-A(5)T-Lys-NH₂;
(N→C) Fethoc-TG(5)T-TA(6)C-C(1O2)CT-GG(5)G-A(6)T-NH₂;
(N→C) Bezenesulfonyl-TG(5)T-TA(2O3)C-CC(1O5)T-GG(5)G-A(6)T-NH₂;
(N→C) Phenyl-TG(5)T-TA(6)C-C(1O2)CT-GG(5)G-A(6)T-NH₂;
(N→C) Fethoc-TG(5)G-TA(5)C-C(1O2)CT-TG(5)G-A(5)T-NH₂;
(N→C) Fethoc-TG(5)T-AA(5)C-CC(1O2)T-GG(5)T-A(5)T-NH₂;
(N→C) Fethoc-TG(6)T-TA(3)C-CC(1O5)T-GG(6)G-A(3)T-NH₂;
(N→C) Fethoc-G(5)TT-A(5)CC(1O2)-CTG-G(5)GA(5)-TC(1O2)-NH₂;
(N→C) Benzyl-G(5)TT-A(5)CC(1O2)-CTG-G(5)GA(5)-TC(1O2)-NH₂;
(N→C) Fethoc-GTT-A(3)CC(1O5)-CTG(6)-GGA(3)-TC(1O5)-NH₂;
(N→C) Fethoc-TA(5)C-C(1O2)CT(1O5)-GG(5)G-A(5)TC-C(1O2)A-NH₂;
(N→C) Fmoc-Leu-TA(4)C-C(1O3)CT-GG(5)G-A(4)TC-C(1O3)A-NH₂;
(N→C) Fethoc-C(1O2)AT-TTG(6)-TTA(5)-CCC(1O2)-TG(6)-NH₂;
(N→C) Fethoc-CA(6)T-TTG(5)-TTA(5)-CCC(1O2)-TG(5)-NH₂;
(N→C) Fethoc-A(6)TT-TG(5)T-TA(5)C-C(1O2)CT-G(5)-NH₂;
(N→C) Fethoc-CA(6)T-CA(6)T-TTG(5)-TTA(5)-CCC(1O2)-TG(5)-NH₂;\
(N→C) Fethoc-A(5)TT-TG(5)T-TA(5)C-CC(1O2)T-GG(5)G-A(5)-NH₂;
(N→C) Fethoc-A(6)TT-TG(5)T-TA(6)C-C(1O2)CT-GG(5)G-A(5)-NH₂; and,
(N→C) Fethoc-A(6)TT-TG(5)T-TA(6)C-C(1O2)CT-G(5)G-NH₂:

wherein,

A, G, T, and C are PNA monomers with a natural nucleobase of adenine, guanine, thymine, and cytosine, respectively;

C(pOq), A(p), A(pOq), G(p), and G(pOq) are PNA monomers with an unnatural nucleobase represented by Formula VI, Formula VII, Formula VIII, Formula IX, and Formula X, respectively;

Formula VI

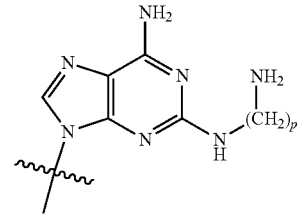

Formula VII

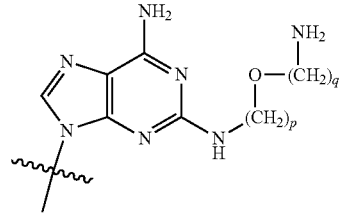

Formula VII

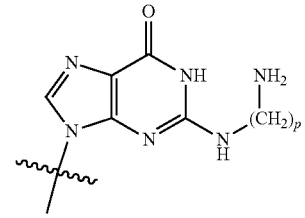

Formula IX

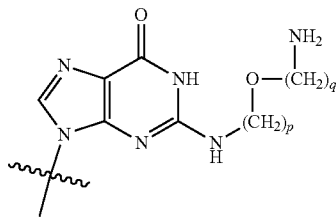

Formula X wherein, p and q are integers; and, the abbreviations for the N- and C-terminus substituents are specifically defined as follows: "Fmoc-" is the abbreviation for "[(9-fluorenyl)methyloxy]carbonyl-"; "Fethoc-" for "[2-(9-fluorenyl)ethyl-1-oxy]carbonyl"; "Ac-" for "acetyl-"; "Benzoyl-" for "benzenecabonyl-"; "Piv-" for "pivalyl-"; "n-Propyl-" for "1-(n-propyl)-"; "H-" for "hydrido-" group; "p-Toluenesulfonyl" for "(4-methylbenzene)-1-sulfonyl-"; "-Lys-" for amino acid residue "lysine"; "—Val-" for amino acid residue "valine"; "-Leu-" for amino acid residue "leucine"; "-Arg-" for amino acid residue "arginine"; "-Gly-" for amino acid residue "glycine"; "[N-(2-Phenylethyl)amino]carbonyl-" for "[N-1-(2-phenylethyl)amino]carbonyl-"; "Benzyl-" for "1-(phenyl)methyl-"; "Phenyl-" for "phenyl-"; "Me-" for "methyl-"; "—HEX-" for "6-amino-1-hexanoyl-", "FAM-" for "5, or 6-fluorescein-carbonyl-(isomeric mixture)", and "—NH$_2$" for non-substituted "-amino" group.

9. A method to treat a disease or condition involving the expression of the human SNAP25 gene comprising administering the peptide nucleic acid derivative according to claim 1 to a human subject.

10. A method to treat a disease or condition involving the expression of the human SNAP25 gene comprising topically administering the peptide nucleic acid derivative according to claim 1 to a human subject.

\* \* \* \* \*

UNITED STATES PATENT AND TRADEMARK OFFICE
CERTIFICATE OF CORRECTION

PATENT NO. : 11,261,448 B2
APPLICATION NO. : 16/475716
DATED : March 1, 2022
INVENTOR(S) : Jung et al.

It is certified that error appears in the above-identified patent and that said Letters Patent is hereby corrected as shown below:

In the Claims

At Column 40, Claim number 6, Line 5, please delete:
"$S_1, S_2, ..., S_n, T_1, T_2, ..., T_{n-1}$, and $T_n$ are hydrido radical;"

And replace with:
--$S_1, S_2, ..., S_{n-1}, S_n, T_1, T_2, ..., T_{n-1}$, and $T_n$ are hydrido radical;--

Signed and Sealed this
Thirty-first Day of May, 2022

Katherine Kelly Vidal
*Director of the United States Patent and Trademark Office*

SEQUENCE LISTING

```
<160> NUMBER OF SEQ ID NOS: 16

<210> SEQ ID NO 1
<211> LENGTH: 14
<212> TYPE: RNA
<213> ORGANISM: Homo sapiens

<400> SEQUENCE: 1
aucccagggu aaca                                                    14

<210> SEQ ID NO 2
<211> LENGTH: 30
<212> TYPE: RNA
<213> ORGANISM: Homo sapiens

<400> SEQUENCE: 2
cucuuuggau cccaggguaa caaaugaugc                                   30
```

```
<210> SEQ ID NO 3
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
atttgttacc ctggga                                                         16

<210> SEQ ID NO 4
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
taccctggga tcca                                                           14

<210> SEQ ID NO 5
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
atctgttacc ctggga                                                         16

<210> SEQ ID NO 6
<211> LENGTH: 25
<212> TYPE: RNA
<213> ORGANISM: Rattus sp.

<400> SEQUENCE: 6
uggcucccag gguaacaaac gaugc                                               25

<210> SEQ ID NO 7
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
atggccgagg acgcagaca                                                      19

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
agcatctttg ttgcacgttg                                                     20

<210> SEQ ID NO 9
<211> LENGTH: 18
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 9
ttgttggagt cagcgcct                                                       18

<210> SEQ ID NO 10
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
atggatgaaa acctagagc                                                      19

<210> SEQ ID NO 11
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
cttcccagca tctttgtt                                                       18

<210> SEQ ID NO 12
<211> LENGTH: 10
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 12
ccatgatcct                                                                10

<210> SEQ ID NO 13
<211> LENGTH: 14
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 13
ccgcagggta acaa                                                           14

<210> SEQ ID NO 14
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
gacgaacggg agcagatg                                                       18

<210> SEQ ID NO 15
<211> LENGTH: 21
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 15
atctcattgc ccatatccag g                                              21

<210> SEQ ID NO 16
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
aaagatgctg gcatcaggac tttggttatg ttggatgagc aaggcgctga ctccaacaaa    60
```